United States Patent
Okatake et al.

(10) Patent No.: US 11,927,646 B2
(45) Date of Patent: Mar. 12, 2024

(54) MAGNETIC FIELD MEASURING APPARATUS

(71) Applicant: Asahi Kasei Microdevices Corporation, Tokyo (JP)

(72) Inventors: Shigeki Okatake, Tokyo (JP); Yoshitaka Moriyasu, Tokyo (JP); Masanori Masuda, Tokyo (JP); Takenobu Nakamura, Tokyo (JP)

(73) Assignee: Asahi Kasei Microdevices Corporation, Tokyo (JP)

( * ) Notice: Subject to any disclaimer, the term of this patent is extended or adjusted under 35 U.S.C. 154(b) by 61 days.

(21) Appl. No.: 17/329,207

(22) Filed: May 25, 2021

(65) Prior Publication Data

US 2021/0286023 A1 Sep. 16, 2021

Related U.S. Application Data

(63) Continuation of application No. PCT/JP2019/050826, filed on Dec. 25, 2019.

(30) Foreign Application Priority Data

Dec. 26, 2018 (JP) .................. 2018-243253

(51) Int. Cl.
*G01R 33/00* (2006.01)
*G01R 33/09* (2006.01)

(52) U.S. Cl.
CPC ...... *G01R 33/0094* (2013.01); *G01R 33/0011* (2013.01); *G01R 33/093* (2013.01); *G01R 33/098* (2013.01)

(58) Field of Classification Search
CPC .............. G01R 33/093; G01R 33/0011; G01R 33/0035; G01R 33/098; G01R 33/0094;
(Continued)

(56) References Cited

U.S. PATENT DOCUMENTS 5,642,045 A 6/1997 Keefe
5,764,061 A 6/1998 Asakawa
(Continued)

FOREIGN PATENT DOCUMENTS

DE 102011083961 A1 4/2013
EP 1795864 A1 6/2007
(Continued)

OTHER PUBLICATIONS

Koichiro Kobayashi et al."Development of Biomagnetic Measurement System with 39ch SQUIDs Magnetometer for a Three Dimensional Magnetic Measurement"T.IEE Japan, vol. 118 Issue 11, 1998, pp. 524-531.
(Continued)

*Primary Examiner* — Alvaro E Fortich

(57) ABSTRACT

Provided is a magnetic field measuring apparatus, comprising: a magnetic sensor array including a plurality of magnetic sensor cells, which is capable of detecting an input magnetic field in three axial directions at a plurality of locations in three-dimensional space; a measurement data acquiring section for acquiring measurement data based on the input magnetic field including a to-be-measured magnetic field; and a measurement data computing section for calibrating the measurement data acquired by the measurement data acquiring section; wherein the measurement data computing section comprises: an indicator calculation section for calculating an indicator illustrating calibration accuracy of the measurement data computing section; and a failure determination section for determining a failure based on the indicator calculated by the indicator calculation section; wherein each of the plurality of magnetic sensor cells comprises: a magnetic sensor; and an output section for outputting a output signal.

20 Claims, 29 Drawing Sheets

(58) Field of Classification Search
CPC .. G01R 33/0017; G01R 33/0206; A61B 5/243
See application file for complete search history.

(56) References Cited

U.S. PATENT DOCUMENTS

| | | |
|---|---|---|
| 5,990,679 A | 11/1999 | Frommer |
| 6,376,933 B1 | 4/2002 | Goetz |
| 6,841,994 B1 | 1/2005 | Wiegert |
| 7,342,399 B1 | 3/2008 | Wiegert |
| 7,603,251 B1 | 10/2009 | Wiegert |
| 2001/0026222 A1 | 10/2001 | Canady |
| 2003/0011767 A1 | 1/2003 | Imura |
| 2003/0097056 A1 | 5/2003 | Suzuki |
| 2004/0155644 A1 | 8/2004 | Stauth |
| 2004/0207396 A1 | 10/2004 | Xiao |
| 2004/0232912 A1 | 11/2004 | Tsukamoto |
| 2004/0263162 A1 | 12/2004 | Kandori |
| 2005/0030018 A1 | 2/2005 | Shibahara |
| 2005/0212515 A1 | 9/2005 | Watanabe |
| 2006/0031038 A1* | 2/2006 | Simola ................ G01R 33/02 702/127 |
| 2006/0055402 A1 | 3/2006 | Seki |
| 2006/0066295 A1 | 3/2006 | Tamura |
| 2007/0108962 A1 | 5/2007 | Taulu |
| 2007/0108975 A1 | 5/2007 | Desplats |
| 2008/0086049 A1 | 4/2008 | Seki |
| 2008/0161714 A1 | 7/2008 | Ahonen |
| 2008/0294386 A1 | 11/2008 | Taulu |
| 2009/0069661 A1 | 3/2009 | Taulu |
| 2009/0184709 A1 | 7/2009 | Kajola |
| 2010/0277163 A1 | 11/2010 | Nakamura |
| 2010/0327862 A1 | 12/2010 | Nagasaka |
| 2011/0074406 A1 | 3/2011 | Mather |
| 2012/0298239 A1 | 11/2012 | Hodgson |
| 2013/0109954 A1 | 5/2013 | Simola |
| 2013/0150702 A1 | 6/2013 | Hokari |
| 2013/0165766 A1 | 6/2013 | Nishikawa |
| 2013/0214774 A1* | 8/2013 | Cesaretti ............ G01R 33/0023 324/252 |
| 2014/0111197 A1 | 4/2014 | Lortie |
| 2014/0257104 A1 | 9/2014 | Dunbar |
| 2014/0343882 A1 | 11/2014 | Taulu |
| 2015/0070008 A1 | 3/2015 | Motz |
| 2015/0145625 A1 | 5/2015 | Fukasawa |
| 2015/0168176 A1 | 6/2015 | Wu |
| 2015/0212166 A1 | 7/2015 | Kandori |
| 2015/0253412 A1 | 9/2015 | Jost |
| 2015/0331072 A1 | 11/2015 | Ogawa |
| 2016/0037277 A1 | 2/2016 | Matsumoto |
| 2016/0041006 A1 | 2/2016 | Ausserlechner |
| 2016/0174867 A1 | 6/2016 | Hatano |
| 2016/0338608 A1 | 11/2016 | Nagasaka |
| 2016/0360987 A1 | 12/2016 | Miyasaka |
| 2017/0090003 A1 | 3/2017 | Guo |
| 2017/0100051 A1 | 4/2017 | Honkura |
| 2017/0212188 A1 | 7/2017 | Kikitsu |
| 2017/0219661 A1 | 8/2017 | Hata |
| 2017/0299662 A1 | 10/2017 | Nagasaka |
| 2017/0299663 A1 | 10/2017 | Nagasaka |
| 2018/0014738 A1 | 1/2018 | Tanaka |
| 2018/0193728 A1 | 7/2018 | Bashkirov |
| 2018/0242865 A1 | 8/2018 | Yamagata |
| 2018/0284310 A1 | 10/2018 | Kawano |
| 2018/0292468 A1 | 10/2018 | Guo |
| 2018/0340987 A1* | 11/2018 | Latham ................ G01R 33/032 |
| 2019/0079141 A1 | 3/2019 | Marauska |
| 2019/0242956 A1 | 8/2019 | Przytarski |
| 2019/0293735 A1 | 9/2019 | Ushioda |
| 2020/0166343 A1 | 5/2020 | Vissiere |
| 2020/0326399 A1 | 10/2020 | Yoshida |
| 2021/0161420 A1 | 6/2021 | Nakamura |
| 2021/0286023 A1 | 9/2021 | Okatake |
| 2021/0345898 A1 | 11/2021 | Okatake |
| 2022/0065953 A1 | 3/2022 | Tsuji |

FOREIGN PATENT DOCUMENTS

| | | |
|---|---|---|
| JP | H01196586 A | 8/1989 |
| JP | H03200083 A | 9/1991 |
| JP | H05232202 A | 9/1993 |
| JP | H09243725 A | 9/1997 |
| JP | H10286244 A | 10/1998 |
| JP | H114815 | 1/1999 |
| JP | 2000051169 A | 2/2000 |
| JP | 2000217798 A | 8/2000 |
| JP | 2000284032 A | 10/2000 |
| JP | 2001083224 A | 3/2001 |
| JP | 2001087237 A | 4/2001 |
| JP | 2001281311 A | 10/2001 |
| JP | 2002272695 A | 9/2002 |
| JP | 2003199723 A | 7/2003 |
| JP | 2004271303 A | 9/2004 |
| JP | 2005049179 A | 2/2005 |
| JP | 2005195376 A | 7/2005 |
| JP | 2005217341 A | 8/2005 |
| JP | 2006047080 A | 2/2006 |
| JP | 2007285865 A | 11/2007 |
| JP | 2008032562 A | 2/2008 |
| JP | 2008142154 A | 6/2008 |
| JP | 2011047910 A | 3/2011 |
| JP | 2011220977 A | 11/2011 |
| JP | 2012152514 A | 8/2012 |
| JP | 2012152515 A | 8/2012 |
| JP | 2013217690 A | 10/2013 |
| JP | 2014081312 A | 5/2014 |
| JP | 2014134388 A | 7/2014 |
| JP | 2014153054 A | 8/2014 |
| JP | 2014153309 A | 8/2014 |
| JP | 2015075465 A | 4/2015 |
| JP | 2016065829 A | 4/2016 |
| JP | 2016183944 A | 10/2016 |
| JP | 2017003312 A | 1/2017 |
| JP | 2017026312 A | 2/2017 |
| JP | 2017062122 A | 3/2017 |
| JP | S153387 B2 | 6/2017 |
| JP | 2017133933 A | 8/2017 |
| JP | 2017166921 A | 9/2017 |
| JP | 2018004286 A | 1/2018 |
| JP | 2018004618 A | 1/2018 |
| JP | 2018011819 A | 1/2018 |
| JP | 2018054461 A | 4/2018 |
| JP | 2021016630 A | 2/2021 |
| NO | 2017209273 A1 | 12/2017 |
| WO | 03046587 A1 | 6/2003 |
| WO | 2005030051 A1 | 4/2005 |

OTHER PUBLICATIONS

Office Action issued for counterpart US Appl. No. 16/365,689, issued by the U.S. Patent and Trademark Office dated Sep. 29, 2022.
Office Action issued for counterpart U.S. Appl. No. 16/434,192, issued by the US Patent and Trademark Office dated Dec. 29, 2021.
Office Action issued for counterpart U.S. Appl. No. 16/434,192, issued by the US Patent and Trademark Office dated Mar. 25, 2021.
Office Action issued for counterpart U.S. Appl. No. 16/434,192, issued by the US Patent and Trademark Office dated Apr. 13, 2022.
Office Action issued for counterpart U.S. Appl. No. 16/434,192, issued by the US Patent and Trademark Office dated Sep. 27, 2022.
Office Action issued for related U.S. Appl. No. 16/809,502, issued by the US Patent and Trademark Office dated Apr. 26, 2022.
Hu Chao et al. ,"A cubic 3-axis magnetic sensor array for wirelessly tracking magnet position and orientation." IEEE SensorsJournal 10.5 (2010): 903-913. (Year: 2010).
Three-Axis Magnetic Sensor H MC 1043 Datasheet (Year: 2012), Aug. 2012.
(ISA/237) Written Opinion of the International Search Authority for International Patent Application No. PCT/JP2019/050826, issued/ mailed by the Japan Patent Office dated Mar. 17, 2020.
Koichiro Kobayashi et al.,"Development of Biomagnetic Measurement System with 39ch SQUIDs Magnetometer for a Three Dimensional Magnetic Measurement"1998vol. 118, Issue 11, pp. 524-531.

(56) References Cited

OTHER PUBLICATIONS

Kensuke Sekihara, "Signal Space Separation Method for a Biomagnetic Sensor Array Arranged on a Flat Plane for Magnetocardiographic Applications:A Computer Simulation Study" Hindawi Journal of Healthcare Engineering vol. 2018, Article ID 7689589, 19 pages.
Samu Taulu et al.,"Presentation of electromagnetic multichannel data: The signal space separation method", Journal of Applied Physics 97, 124905, (2005), PP124905-1-10.
Samu Taulu et al.,"Applications of the Signal Space Separation Method",IEEE Transactions on Signal Processing, vol. 53, No. 9, Sep. 2005,PP3359-3372.
Office Action issued for counterpart Japanese Application No. 2018-157607, issued by the Japan Patent Office dated Oct. 23, 2018 (drafted on Oct. 12, 2018).
Office Action issued for counterpart Japanese Application No. 2018-157607, issued by the Japan Patent Office dated Jan. 29, 2019 (drafted on Jan. 23, 2019).
Office Action issued for counterpart U.S. Appl. No. 16/365,689, issued by the US Patent and Trademark Office dated Mar. 7, 2022.
International Search Report and (ISA/237) Written Opinion of the International Search Authority for International Patent Application No. PCT/JP2019/032548, issued/mailed by the Japan Patent Office dated Oct. 21, 2019.
Samu Taula et al.,"Presentation of electromagnetic multichannel data: The signal space separation method", Journal of Applied Physics 97, 124905 (2005), PP124905-1-124905-10.
Kensuke Skihara,"Signal Space Separation Method for a Biomagnetic Sensor Array Arranged on a Flat Plane for Magnetocardiographic Applications: A Computer Simulation Study",Journal of Healthcare Engineering vol. 2018, Article ID 7689589, PP1-19, https://doi.org/10.1155/2018/7689589.

\* cited by examiner

MAGNETIC FIELD MEASURING APPARATUS

The contents of the following Japanese patent application are incorporated herein by reference:
NO. 2018-243253 filed in JP on Dec. 26, 2018
NO. PCT/JP2019/050826 filed in WO on Dec. 25, 2019

BACKGROUND

1. Technical Field

The present invention relates to a magnetic field measuring apparatus.

2. Related Art

Conventionally, a magnetic field measuring apparatus that measures a magnetic field emitted from the head or the chest of a subject, using a sensor platform board having a plurality of Tunnel Magneto-Resistance (TMR) elements arranged in an array form has been known (refer to, for example, Patent Document 1). Patent Document 1: Japanese Patent Application Publication No. 2012-152514.

3. Technical Problem

The conventional magnetic field measuring apparatus, with a pair of magnetic detection elements stacked in a magnetic field detection direction, has measured a to-be-measured magnetic field with a disturbance magnetic field suppressed, based on the following mechanism. Specifically, the disturbance magnetic field results in the same magnitude between the measurement results of the pair of magnetic detection elements, whereas the to-be-measured magnetic field results in different magnitudes between the measurement results of the pair of magnetic detection elements. However, it is desirable to realize a magnetic field measuring apparatus that can measure the magnetic field with higher precision, for example, measure the weak biological magnetic field generated by the electrical activity of the heart (indicated as "cardiac magnetic field") and examinate the heart condition with higher precision, or the like.

GENERAL DISCLOSURE

To solve the problem described above, a first aspect of the present invention provides a magnetic field measuring apparatus. A magnetic field measuring apparatus may include a magnetic sensor array including a plurality of magnetic sensor cells, which is capable of detecting an input magnetic field in three axial directions at a plurality of locations in three-dimensional space. The magnetic field measuring apparatus may include a measurement data acquiring section for acquiring measurement data based on the input magnetic field including a to-be-measured magnetic field. The magnetic field measuring apparatus may include a measurement data computing section for calibrating the measurement data acquired by the measurement data acquiring section. The measurement data computing section may include an indicator calculation section for calculating an indicator illustrating calibration accuracy of the measurement data computing section. The measurement data computing section may include a failure determination section for determining a failure based on the indicator calculated by the indicator calculation section. Each of the plurality of magnetic sensor cells may include a magnetic sensor. Each of the plurality of magnetic sensor cells may include an output section for outputting an output signal.

Each of the plurality of magnetic sensor cells may further include a first magnetic field generation section for generating a feedback magnetic field configured to reduce an input magnetic field detected by the magnetic sensor by a magnitude corresponding to the output signal, and the output section is configured to output the output signal corresponding to a feedback current flowing to generate the feedback magnetic field by the first magnetic field generation section.

The measurement data computing section may further include a signal space separation section for performing signal separation on the input magnetic field spatial distribution indicated by magnetic field measurement data generate from the measurement data, using, as basis vectors, signal vectors output by each of the magnetic sensor when the magnetic sensor array detects a magnetic field having a spatial distribution of orthonormal functions The indicator calculation section may be configured to calculate the indicator based on a result of a signal separation performed by the signal space separation section.

The indicator calculation section may be configured to calculate the indicator based on statistics of magnetic field measurement data in the plurality of magnetic sensor cells generated from the measurement data.

The measurement data computing section may further include an indicator output section for outputting the indicator calculated by the indicator calculation section.

The measurement data computing section may be configured to recalibrate the measurement data based on the indicator calculated by the indicator calculation section.

Each of the magnetic sensors may include a magnetoresistive element and two magnetic flux concentrators arranged on both ends of the magnetoresistive element. The magnetoresistive element may be arranged at a position sandwiched between by two of the magnetic flux concentrators.

The first magnetic field generation section may include a first coil wrapped along an axial direction of a magnetic field which is a detection target of the magnetic sensor, so as to enclose the magnetoresistive element and two of the magnetic flux concentrators.

Each of the plurality of magnetic sensor cells may further include a second magnetic field generation section for generating a cancellation magnetic field configured to reduce an environment magnetic field, which is included in an input magnetic field detected by the magnetic sensor. The second magnetic field generation section may include a second coil wrapped along an axial direction of a magnetic field which is a detection target of the magnetic sensor, so as to enclose the magnetoresistive element and two of the magnetic flux concentrators.

Each of the plurality of magnetic sensor cells may include three sensor sections, each of which may include the magnetic sensor, the first magnetic field generation section and the output section, and is capable of detecting a magnetic field in the three axial directions.

The magnetic sensor array may be arranged in a curved surface shape.

The summary clause does not necessarily describe all necessary features of the embodiments of the present invention. The present invention may also be a sub-combination of the features described above.

DESCRIPTION OF EXEMPLARY EMBODIMENTS

Hereinafter, the invention will be described through embodiments of the invention, but the following embodiments do not limit the invention according to claims. In addition, not all combinations of features described in the embodiments necessarily have to be essential to solving means of the invention.

Figure 1:
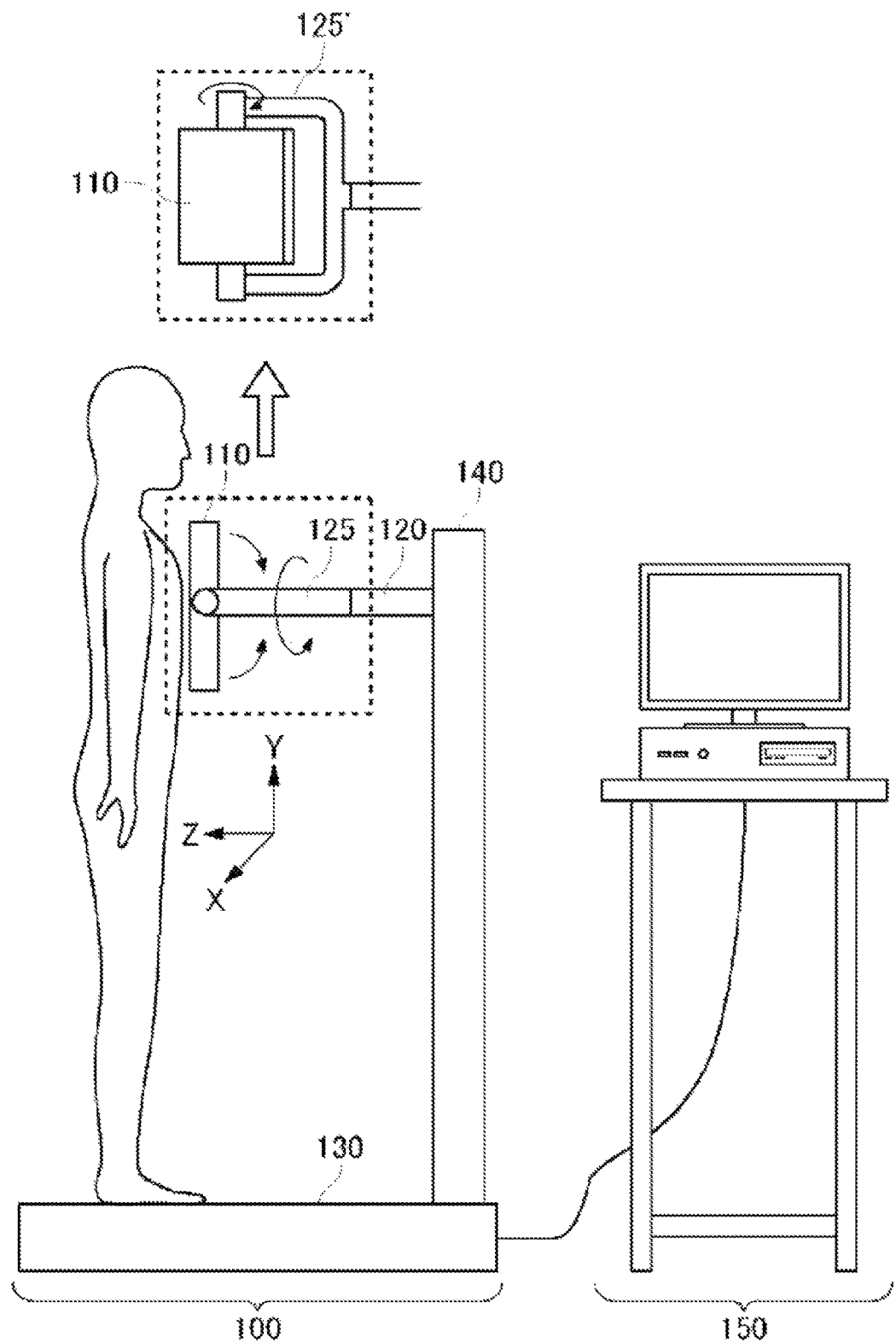
FIG. 1 illustrates a configuration of a magnetocardiographic measuring apparatus 10 according to the present embodiment.

FIG. 1 illustrates a configuration of a magnetocardiographic measuring apparatus 10 according to the present embodiment. The magnetocardiographic measuring apparatus 10, as one example of a magnetic field measuring apparatus, is configured to measure a cardiac magnetic field, which is a magnetic field generated by the electrical activity of human heart, using a magnetoresistive element. Also, the magnetocardiographic measuring apparatus 10 may be used for measuring a cardiac magnetic field of a living subject other than a human.

The magnetocardiographic measuring apparatus 10 includes a main body 100 and an information processing section 150. The main body 100 is a component for sensing the cardiac magnetic field of a subject, and includes a magnetic sensor unit 110, a head 120, a driving section 125, a base portion 130 and a pole portion 140.

The magnetic sensor unit 110 is arranged at a position facing the heart in the chest of the subject during a magnetocardiographic measurement, and senses the cardiac magnetic field of the subject. The head 120 supports the magnetic sensor unit 110, and causes the magnetic sensor unit 110 to face the subject. The driving section 125 is provided between the magnetic sensor unit 110 and the head 120, and changes the orientation of the magnetic sensor unit 110 relative to the head 120 when performing calibration. The driving section 125 according to the present embodiment includes a first actuator that can cause the magnetic sensor unit 110 to rotate 360 degrees about a Z-axis in the drawing and a second actuator that causes the magnetic sensor unit 110 to rotate about an axis perpendicular to the Z-axis (an X-axis for the state in the drawing), and changes the azimuth angle and zenith angle of the magnetic sensor unit 110 using these actuators. As illustrated by the driving section 125 in the drawing, the driving section 125 is Y-shaped when viewed from the Y-axis direction in the drawing, and the second actuator can cause the magnetic sensor unit 110 to rotate 360 degrees about the X-axis in the drawing.

The base portion 130 is a base platform that supports other components, and is a platform the subject steps on during a magnetocardiographic measurement in the present embodiment. The pole portion 140 supports the head 120 at the height of the chest of the subject. The pole portion 140 may be capable of extending and contracting in an up-down direction in order to adjust the height of the magnetic sensor unit 110 to the height of the chest of the subject.

The information processing section 150 is a component for processing the data measured by the main body 100 and outputting the data by presenting and/or printing or the like. The information processing section 150 may be a computer such as a PC (personal computer), a tablet computer, a smartphone, a workstation, a server computer, or a general-purpose computer, or may be a computer system in which a plurality of computers are connected. Alternatively, the information processing section 150 may be a dedicated computer designed for information processing for magnetocardiographic measurement, or may be dedicated hardware implemented by a dedicated line.

Figure 2:
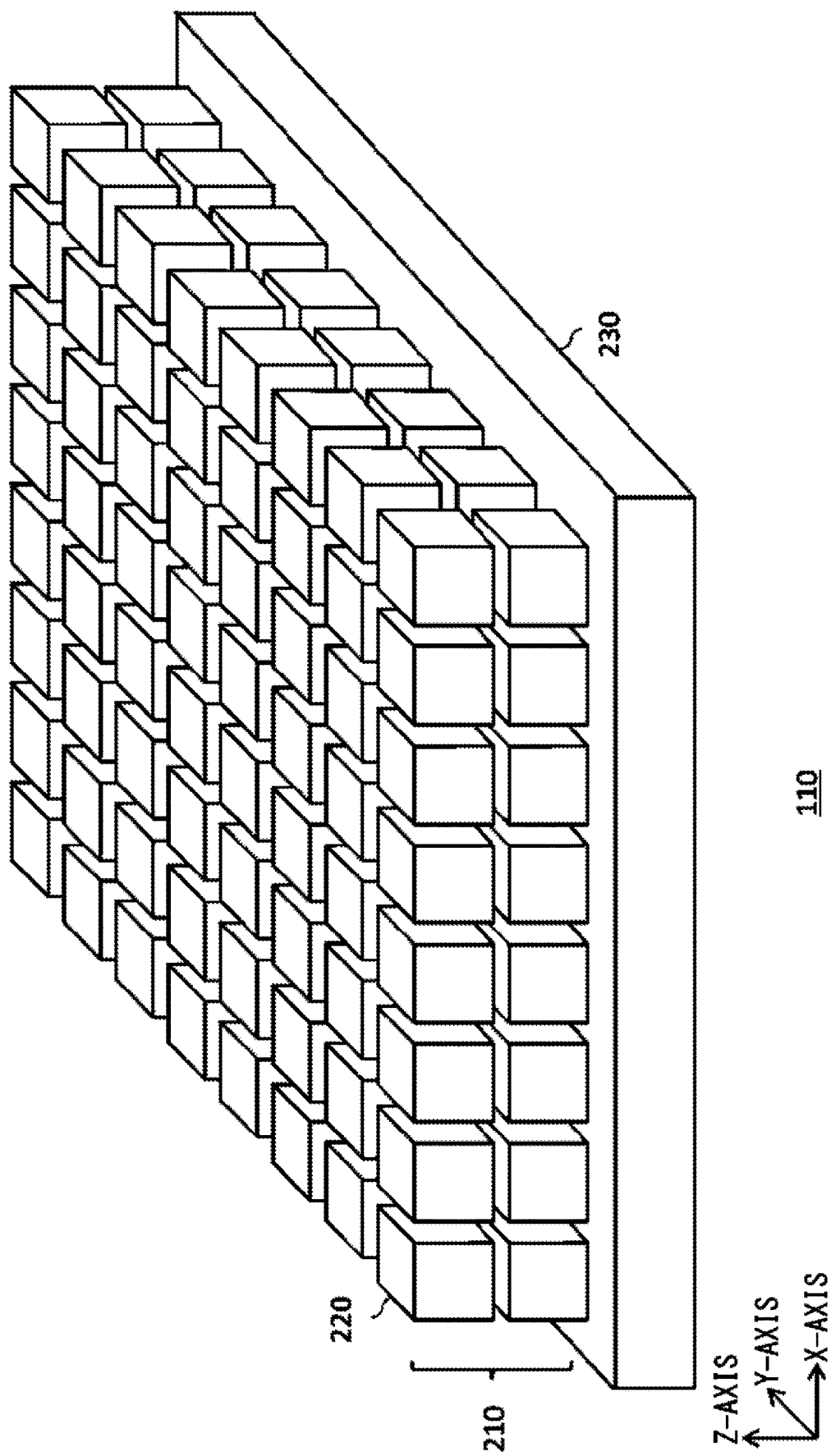
FIG. 2 illustrates a configuration of the magnetic sensor unit 110 according to the present embodiment.

FIG. 2 illustrates a configuration of the magnetic sensor unit 110 according to the present embodiment. The magnetic sensor unit 110 includes a magnetic sensor array 210 and a sensor data gathering section 230. The magnetic sensor array 210 includes a plurality of magnetic sensor cells 220, and is capable of detecting input magnetic fields in three axial directions at a plurality of locations in three-dimensional space. In the present drawing, the plurality of magnetic sensor cells 220 in the magnetic sensor array 210 are arranged in a planar shape, in each of the X direction, the Y direction, and the Z direction (for example, a total of 128 magnetic sensor cells 220 with 8 cells arranged in the X direction, 8 cells arranged in the Y direction, and 2 cells arranged in the Z direction).

The sensor data gathering section 230 is electrically connected to the plurality of magnetic sensor cells 220 included in the magnetic sensor array 210 (not illustrated in the drawings), gathers sensor data (detection signals) from the plurality of magnetic sensor cells 220, and supplies this sensor data to the information processing section 150.

Figure 3:
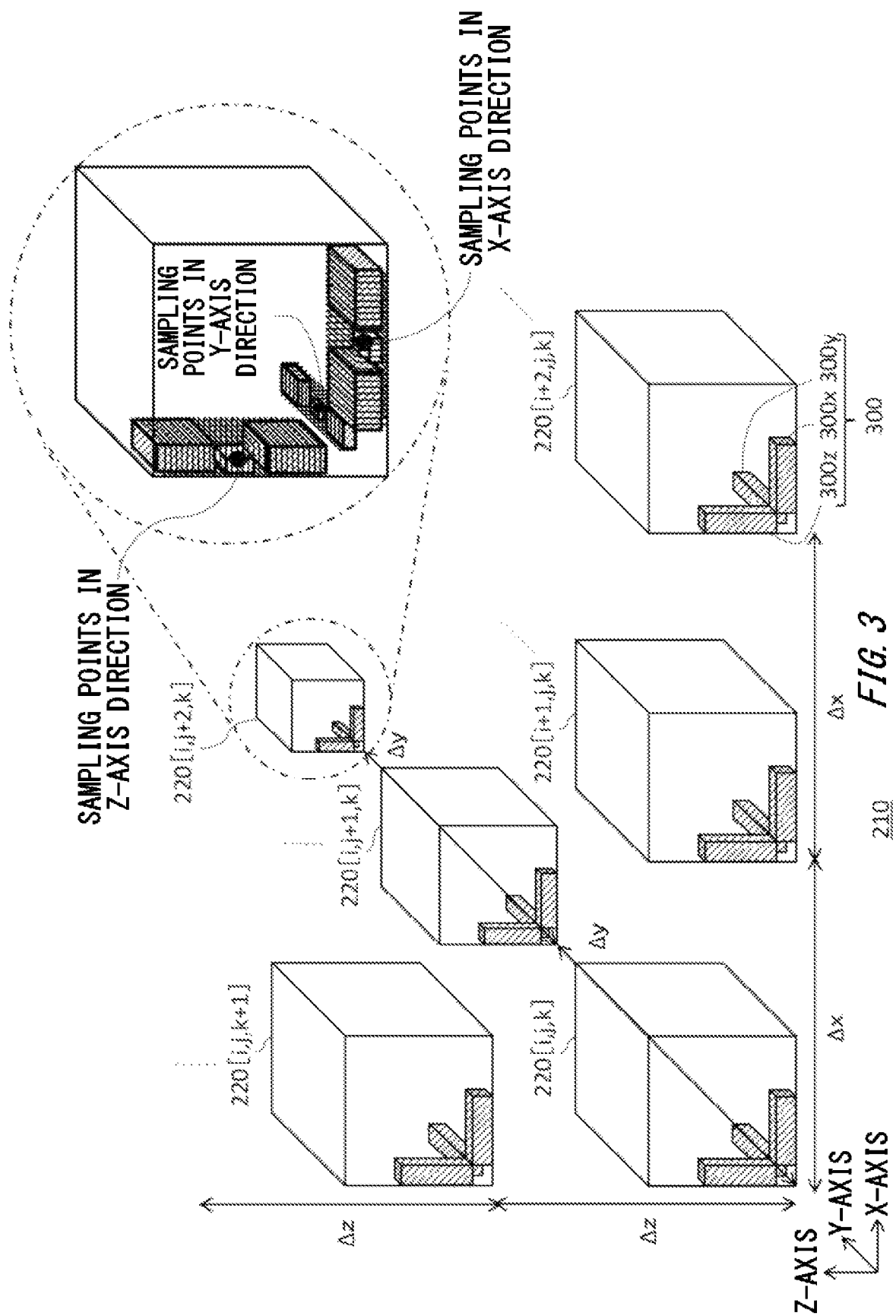
FIG. 3 illustrates a configuration and an arrangement of a magnetic sensor cell 220 of a magnetic sensor array 210 according to the present embodiment.

FIG. 3 illustrates the configuration and arrangement of the magnetic sensor cell 220 in the magnetic sensor array 210 according to the present embodiment. Each of the plurality of magnetic sensor cells 220 has at least one sensor section 300, which respectively has a magnetoresistive element. In the present drawing, one example is shown of a case in which each of the plurality of magnetic sensor cells 220 includes three sensor sections 300x to 300z (referred to collectively as "sensor sections 300"), and is capable of detecting an input magnetic field in three axial directions. However, any of the plurality of magnetic sensor cells 220 may be not limited to having three sensor sections 300x to 300z, but may be capable of detecting input magnetic fields in three axial directions at a plurality of locations in three-dimensional space in at least a part of the magnetic sensor array 210. The sensor section 300x is arranged along the X-axis direction and is capable of detecting a magnetic field in the X-axis direction. Also, the sensor section 300y is arranged along the Y-axis direction and is capable of detecting a magnetic field in the Y-axis direction. Also, the sensor section 300z is arranged along the Z-axis direction and is capable of detecting a magnetic field in the Z-axis direction. As illustrated in an enlarged view shown in a dash-dot line part of the present drawing, in the present embodiment, each of the sensor sections 300 respectively has the magnetic flux concentrators arranged on both ends of the magnetoresistive element. Accordingly, each sensor section 300 uses the magnetoresistive element arranged in a narrow position sandwiched between the magnetic flux concentrators to perform the sampling on the magnetic field spatial distribution, so that spatial sampling points can be clarified in each axial direction. The details of the configuration of each sensor section 300 are described below.

In the present drawing, the three axial directions of the magnetic field detected by the sensor sections 300x, 300y and 300z are the same direction as those of the three dimensions in which the magnetic sensor cells 220 are arranged. Therefore, it becomes easier to understand each component of the distribution of the measured magnetic field. Further, it is preferable that, within each magnetic sensor cell 220, the three sensor sections 300x, 300y and 300z do not overlap each other when viewed from any of the three-dimensional directions in which the magnetic sensor cells 220 are arranged, and one end of each sensor section 300 is provided on a gap side provided between the three sensor sections 300 and the other end of each sensor section 300 is arranged extending away from the gap in each axial direction of the three axial directions. As one example, the present drawing illustrates an example where an air space (gap) is provided at the lower left corner portion in front view of the magnetic sensor cell 220, and the sensor sections 300x, 300y, and 300z are provided to respectively extend in the X-axis, the Y-axis, and the Z-axis directions, so that one end of each sensor section is provided in contact with the air space and the other end is away from the air space. In the present drawing, the sensor sections 300x, 300y and 300z are arranged along three sides orthogonal to each other from one corner portion of the magnetic sensor cell 220 having a cubic shape, with an air space provided at the one corner portion. However, the three axial directions in which the magnetic field is detected may instead be different from the three dimensional directions in which the magnetic sensor cells 220 are arranged. For example, instead of the X-axis, Y-axis, and Z-axis serving as the three axial directions in which the magnetic field is detected, the r-axis, θ-axis, and φ-axis of the polar coordinate system may be used. Furthermore, instead of the X-axis, Y-axis, and Z-axis, the r-axis, θ-axis, and φ-axis of the polar coordinate system may be used as the three dimensional directions in which the magnetic sensor cells 220 are arranged. In a case where the three axial directions in which the magnetic field is detected are different from the three dimensional directions in which the magnetic sensor cells 220 are arranged, there are no restrictions on the arrangement of the sensor sections 300 in the magnetic sensor cells 220 or the arrangement directions of the magnetic sensor cells 220, and it is possible to increase flexibility of the design of the magnetic sensor array 210. Also, in the corner portion of the magnetic sensor cell 220, a gap may not be provided, and a sensor sections 300x, 300y and 300z may be provided. In this case, the magnetic sensor cell 220 can be configured to be smaller, thereby a magnetic sensor array 210 having such a plurality of magnetic sensor cells 220 can be miniaturized.

Figure 4:
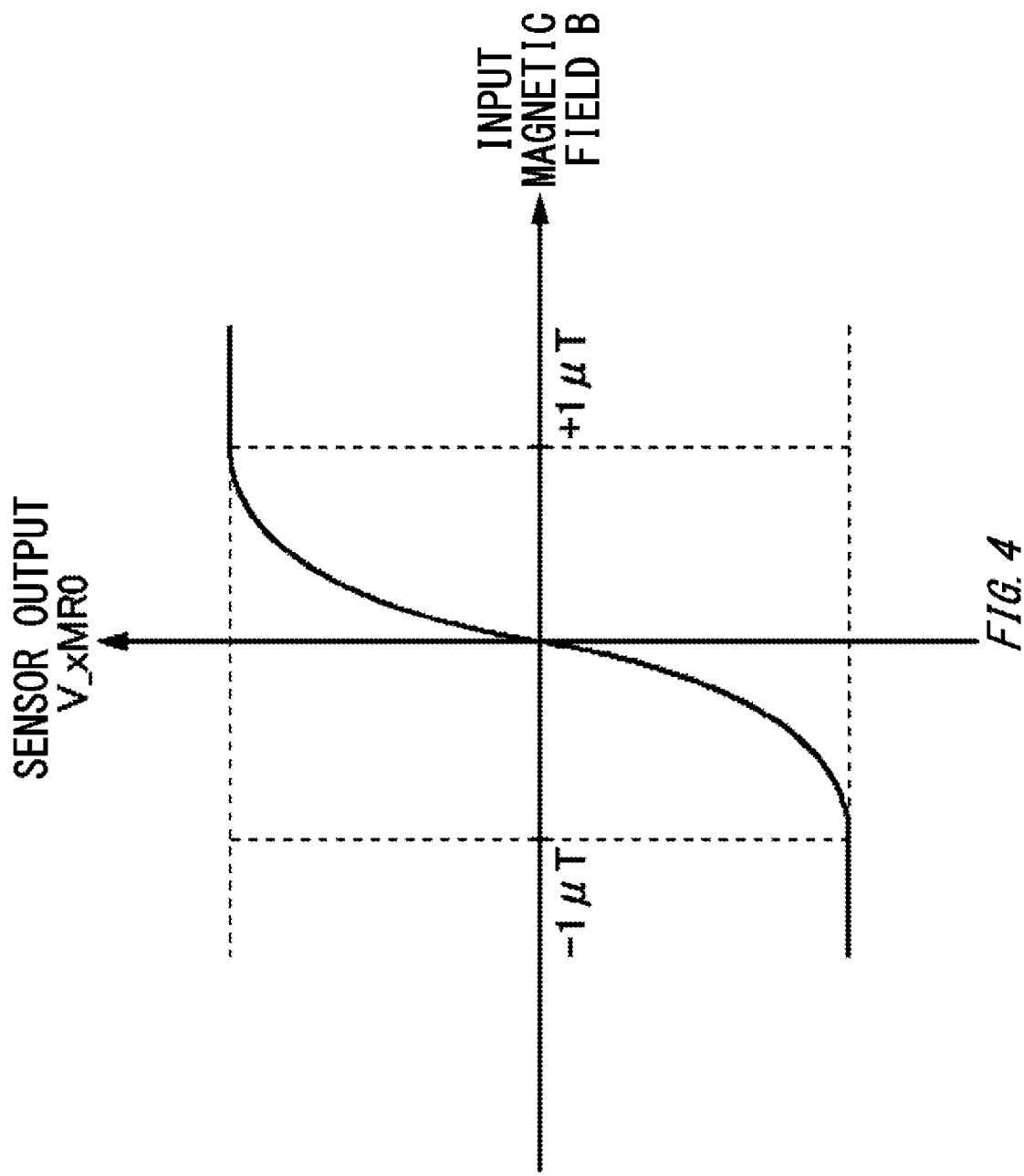
FIG. 4 illustrates one example of input/output characteristics of a magnetic sensor having a magnetoresistive element according to the present embodiment.

FIG. 4 illustrates one example of input/output characteristics of the magnetic sensor having the magnetoresistive element according to the present embodiment. In the present drawing, the horizontal axis indicates the magnitude B of the input magnetic field input to the magnetic sensor, and the vertical axis indicates the magnitude V_xMR 0 of the detection signal of the magnetic sensor. The magnetic sensor, for example, includes a Giant Magneto-Resistance (GMR) element, a Tunnel Magneto-Resistance (TMR) element, or the like, and detects the magnitude of the magnetic field in one predetermined axial direction.

Such a magnetic sensor has high magnetic sensitivity, which is the slope of the detection signal V_xMR0 relative to the input magnetic field B, and can detect a very small magnetic field of approximately 10 pT. On the other hand, the detection signal V_xMR0 becomes saturated when the absolute value of an input magnetic field B is approximately 1 µT, for example, and the magnetic sensor has a narrow range in which the linearity of the input/output characteristic is good. Therefore, when a closed loop is added to such a magnetic sensor, which generates a feedback magnetic field, it is possible to improve the linearity of the magnetic sensor. The following describes such a magnetic sensor.

Figure 5:
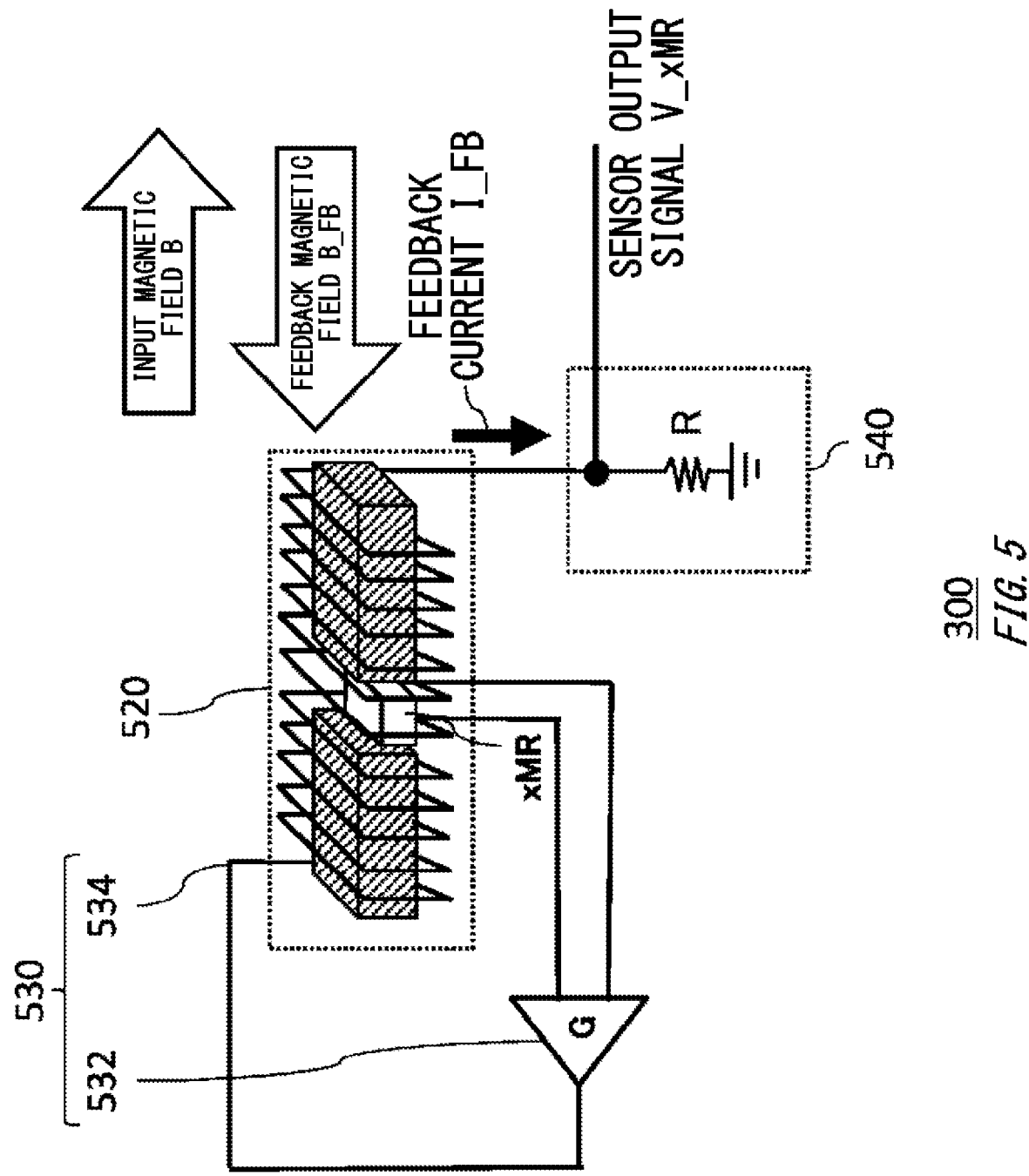
FIG. 5 illustrates a configuration example of a sensor section 300 according to the present embodiment.

FIG. 5 illustrates a configuration example of the sensor section 300 according to the present embodiment. The sensor section 300 is provided inside each of the plurality of magnetic sensor cells 220, and includes a magnetic sensor 520, a first magnetic field generation section 530 and an output section 540. Note that a part of the sensor section 300, for example, such as a first amplification circuit 532 and the output section 540, may be provided on the sensor data gathering section 230 side instead of the magnetic sensor cell 220 side.

The magnetic sensor 520 includes a magnetoresistive element such as a GMR element or a TMR element, similar to the magnetic sensor described in FIG. 4. Also, each of the magnetic sensors 520 includes a magnetoresistive element and two magnetic flux concentrators arranged on both ends of the magnetoresistive element, and the magnetoresistive element is arranged in a position sandwiched between the two magnetic flux concentrators. When a positive direction of the magnetosensitive axis is defined as a +X direction, the magnetoresistive element of the magnetic sensor 520 may be formed so that a resistance value increases in response to an input of a magnetic field in a +X direction and the resistance value decreases in response to an input of a magnetic field in a −X direction. That is, observing a change in the resistance value of the magnetoresistive element of the magnetic sensor 520 can detect the magnitude of the magnetic field B input to the magnetic sensor 520. For example, when the magnetic sensitivity of the magnetic sensor 520 is S, the detection result of the magnetic sensor 520 for the input magnetic field B can be calculated as S×B. Note that as one example, the magnetic sensor 520 is connected to a power source or the like, and outputs a voltage drop corresponding to the change of the resistance value, as a detection result of the input magnetic field. The details of the configuration of the magnetic sensor 520 are described below.

The first magnetic field generation section 530 is configured to generate a feedback magnetic field, which has a magnitude corresponding to the output signal output by the output section 540, for reducing the input magnetic field detected by the magnetic sensor 520, and apply the feedback magnetic field to the magnetic sensor 520. For example, the first magnetic field generation section 530 is configured to generate a feedback magnetic field B_FB, which is in a direction opposite to the magnetic field B input to the magnetic sensor 520 and has an absolute value substantially the same as the input magnetic field, and operate to cancel out the input magnetic field. The first magnetic field generation section 530 includes a first amplification circuit 532 and a first coil 534.

The first amplification circuit 532 is configured to output a current corresponding to the detection result of the input magnetic field of the magnetic sensor 520 as a feedback current I_FB. When the magnetoresistive element included in the magnetic sensor 520 is configured by a bridge circuit including at least one magnetoresistive element, each of the output terminals of the bridge circuit are connected to the input terminal pair of the first amplification circuit 532. Then, the first amplification circuit 532 is configured to output a current corresponding to the output of the bridge circuit as a feedback current I_FB. The first amplification circuit 532, for example, includes a transconductance amplifier, and outputs a feedback current I_FB corresponding to the output voltage of the magnetic sensor 520. For example, when the voltage/current conversion coefficient of the first amplification circuit 532 is referred to as G, the feedback current I_FB can be calculated as G×S×B.

The first coil 534 is configured to generate a feedback magnetic field B_FB corresponding to the feedback current I_FB. The first coil 534 is wrapped along the axial direction of the magnetic field with the magnetic sensor 520 being the detection target, so as to enclose the magnetoresistive element and the two magnetic flux concentrators arranged on both ends of the magnetoresistive element, which are included in the magnetic sensor 520. It is preferable that the first coil 534 generates a uniform feedback magnetic field B_FB over the entire magnetic sensor 520. For example, when the coil factor of the first coil 534 is referred to as β, the feedback magnetic field B_FB can be calculated as β×I_FB. Herein, the feedback magnetic field B_FB is generated with an orientation that cancels out the input magnetic field B, and therefore the magnetic field input to the magnetic sensor 520 is reduced to B-B_FB. Accordingly, the feedback current I_FB is shown as shown in the following expression.

$$I\_FB = G \times S \times (B - \beta \times I\_FB) \qquad \text{[Expression 1]}$$

When Expression 1 is solved for the feedback current I_FB, it is possible to calculate the value of the feedback current I_FB in a steady state of the sensor section 300. When the magnetic sensitivity S of the magnetic sensor 520 and the voltage/current conversion coefficient G of the first amplification circuit 532 are sufficiently large, the following expression can be calculated from Expression 1.

$$I\_FB = \frac{G \times S \times B}{1 + G \times S \times \beta} \cong \frac{B}{\beta} \qquad \text{[Expression 2]}$$

The output section 540 is configured to output an output signal V_xMR corresponding to a flowing feedback current I_FB for generating a feedback magnetic field B_FB by the first magnetic field generation section 530. The output section 540, for example, includes a resistance element of resistance value R, and outputs a voltage drop generated by the feedback current I_FB flowing through the resistance element as a output signal V_xMR. In this case, the output signal V_xMR is calculated from Expression 2 as shown in the following expression.

$$V\_xMR = R \times I\_FB = \frac{R \times B}{\beta} \quad \text{[Expression 3]}$$

As described above, the sensor section 300 generates the feedback magnetic field that reduces the magnetic field input thereto from the outside, and therefore the magnetic field substantially input to the magnetic sensor 520 is reduced. In this way, the sensor section 300, for example, is non-linear as a magnetic sensor 520 as shown in FIG. 4, and can prevent the detection signal V_xMR from being saturated even when the absolute value of the input magnetic field B exceeds 1 µT by using a magnetoresistive element with a characteristic of narrow operating magnetic field range. The following describes the input/output characteristics of such a sensor section 300.

Figure 6:
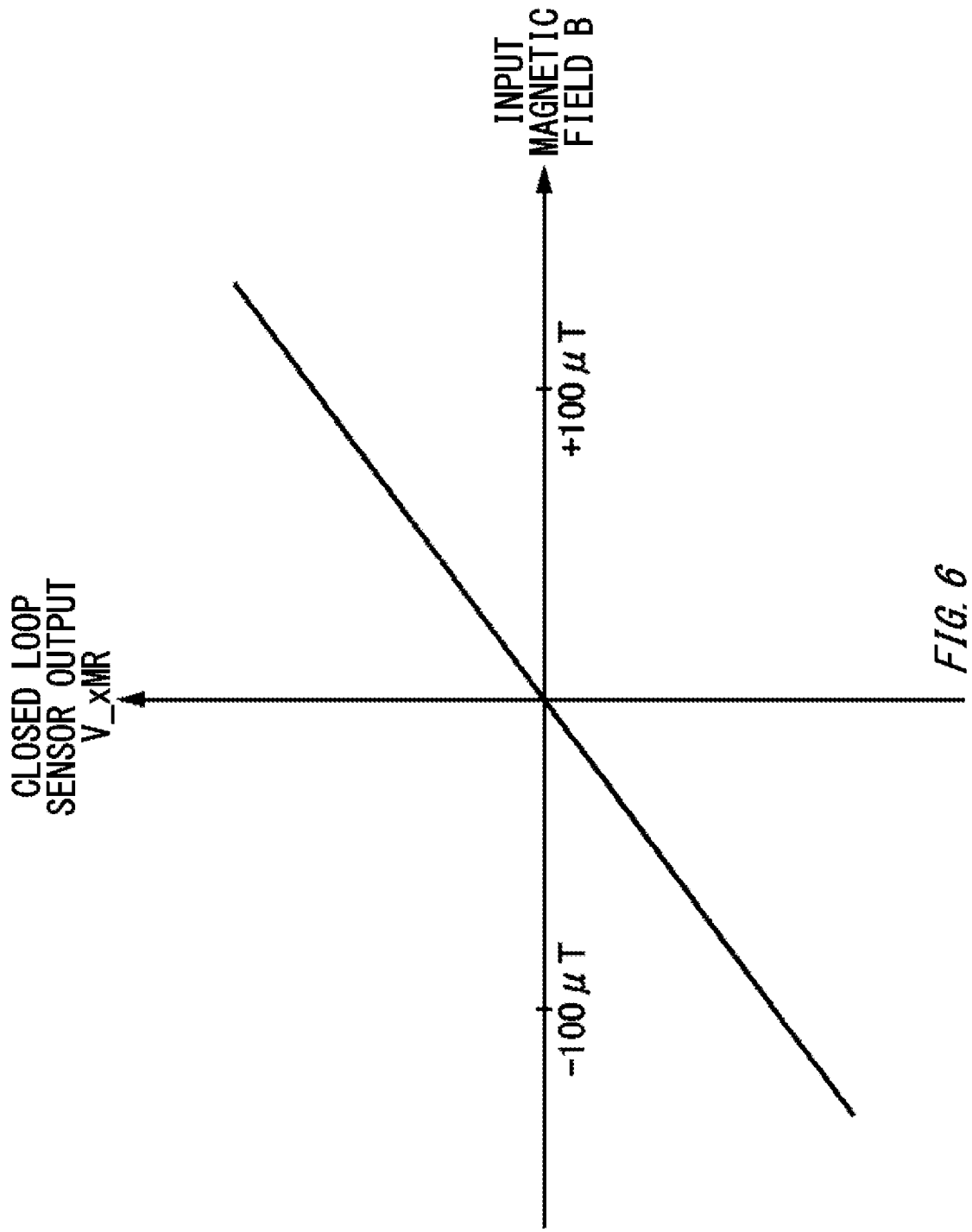
FIG. 6 illustrates one example of input/output characteristics of the sensor section 300 according to the present embodiment.

FIG. 6 illustrates one example of input/output characteristics of the sensor section 300 according to the present embodiment. In the present drawing, the horizontal axis indicates the magnitude B of the input magnetic field input to the sensor section 300, and the vertical axis indicates the magnitude V_xMR of the detection signal of the sensor section 300. The sensor section 300 has high magnetic sensitivity and can detect a very small magnetic field of approximately 10 pT. Furthermore, even when the absolute value of the input magnetic field B exceeds 100 µT, for example, the sensor section 300 can maintain good linearity for the detection signal V_xMR.

That is, the sensor section 300 according to the present embodiment is configured such that the detection result for the input magnetic field B has linearity in a predetermined range of the input magnetic field B where the absolute value of the input magnetic field B is less than or equal to several hundred µT for example. By using such a sensor section 300, it is possible to easily detect very weak magnetic signals, such as cardiac magnetic field signals.

Figure 7:
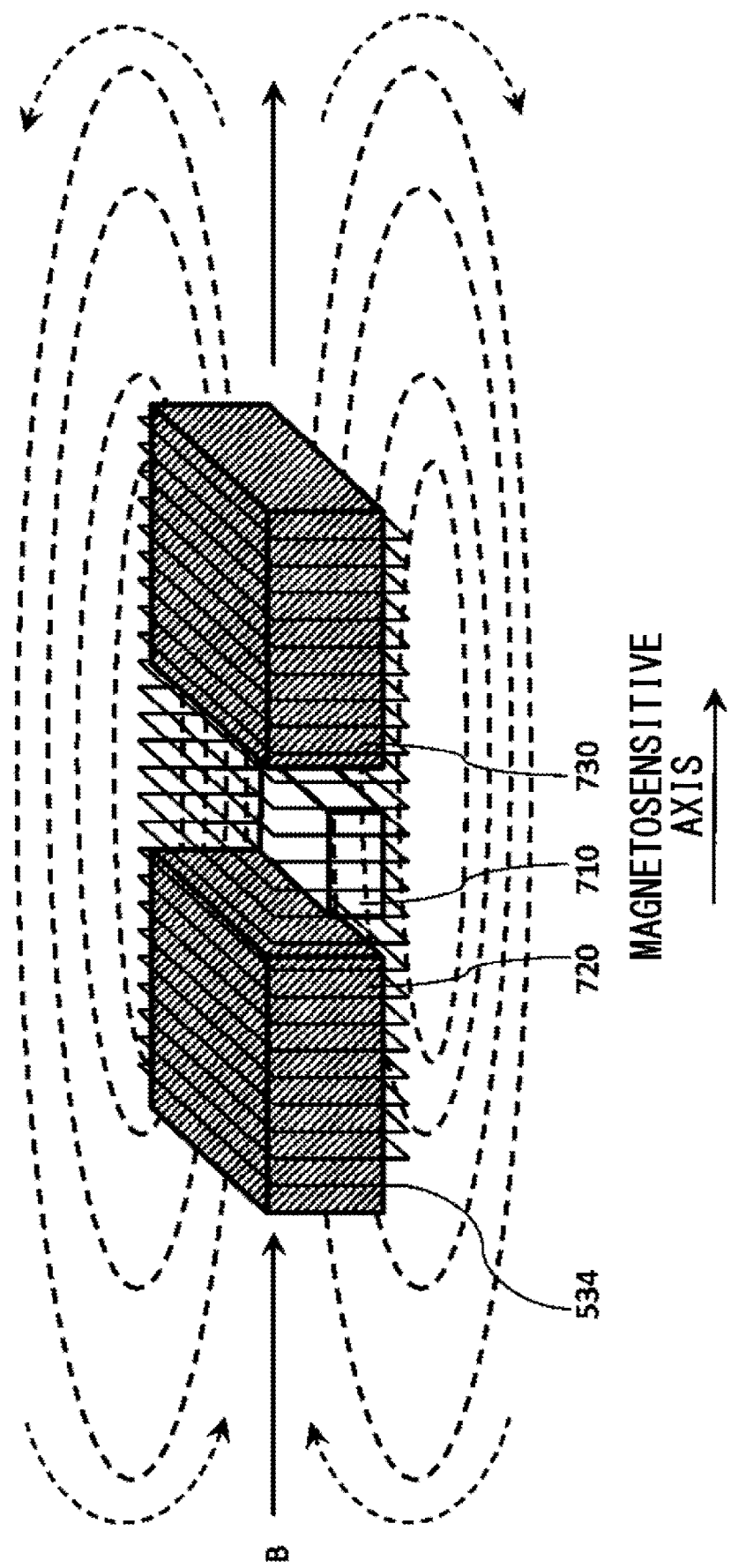
FIG. 7 illustrates a configuration example of a magnetic sensor 520 according to the present embodiment.

FIG. 7 illustrates a configuration example of the magnetic sensor 520 according to the present embodiment. In the present drawing, the magnetic sensor 520 includes a magnetoresistive element 710, magnetic flux concentrators 720 and 730 arranged on both ends of the magnetoresistive element 710. The magnetic flux concentrators 720 and 730 are arranged on both ends of the magnetoresistive element 710 to sandwich the magnetoresistive element 710 in between. In the present drawing, the magnetic flux concentrator 720 is provided on the negative side of the magnetoresistive element 710 along the magnetosensitive axis, and the magnetic flux concentrator 730 is provided on the positive side of the magnetoresistive element 710 along the magnetosensitive axis. Note that herein, the magnetosensitive axis may be along the fixed magnetizing direction in the magnetization fixed layer for forming the magnetoresistive element 710. Also, the resistance of the magnetoresistive element 710 may increase or decrease when the magnetic field is input toward the positive side from the negative side of the magnetosensitive axis. The magnetic flux concentrators 720 and 730 are formed of a material with high magnetic permeability such as permalloy, for example. Then, when the magnetic sensor 520 is configured as illustrated in the present drawing, the first coil 534 is wrapped along the axial direction of the magnetic field with the magnetic sensor 520 being the detection target, so as to enclose the cross section of the magnetoresistive element 710, the magnetic flux concentrators 720 and 730 arranged on both ends of the magnetoresistive element 710. Also, the magnetic sensor 520 may have a plurality of pairs including a magnetoresistive element and magnetic flux concentrators arranged on the both ends when having a plurality of magnetoresistive elements 710 within one magnetic sensor 520. In this case, the first coil 534 may be wrapped so that a pair including a magnetoresistive element and magnetic flux concentrators arranged on the both ends is enclosed by one coil.

In such a magnetic sensor 520, when a magnetic field is input from the negative side to the positive side of the magnetosensitive axis, the magnetic flux concentrators 720 and 730 formed of the material with high magnetic permeability are magnetized, thereby generating a magnetic flux distribution such as shown by a dashed line in the present drawing. Then, the magnetic flux generated by the magnetization of the magnetic flux concentrators 720 and 730 passes through the position of the magnetoresistive element 710 sandwiched between the two magnetic flux concentrators 720 and 730. Therefore, the magnetic flux density at the position of the magnetoresistive element 710 can be significantly increased by arranging the magnetic flux concentrators 720 and 730. Also, as shown in the present drawing, the spatial sampling points can be clarified by performing the sampling on the magnetic field spatial distribution using the magnetoresistive element 710 arranged at a narrow position sandwiched between the magnetic flux concentrators 720 and 730.

Figure 8:
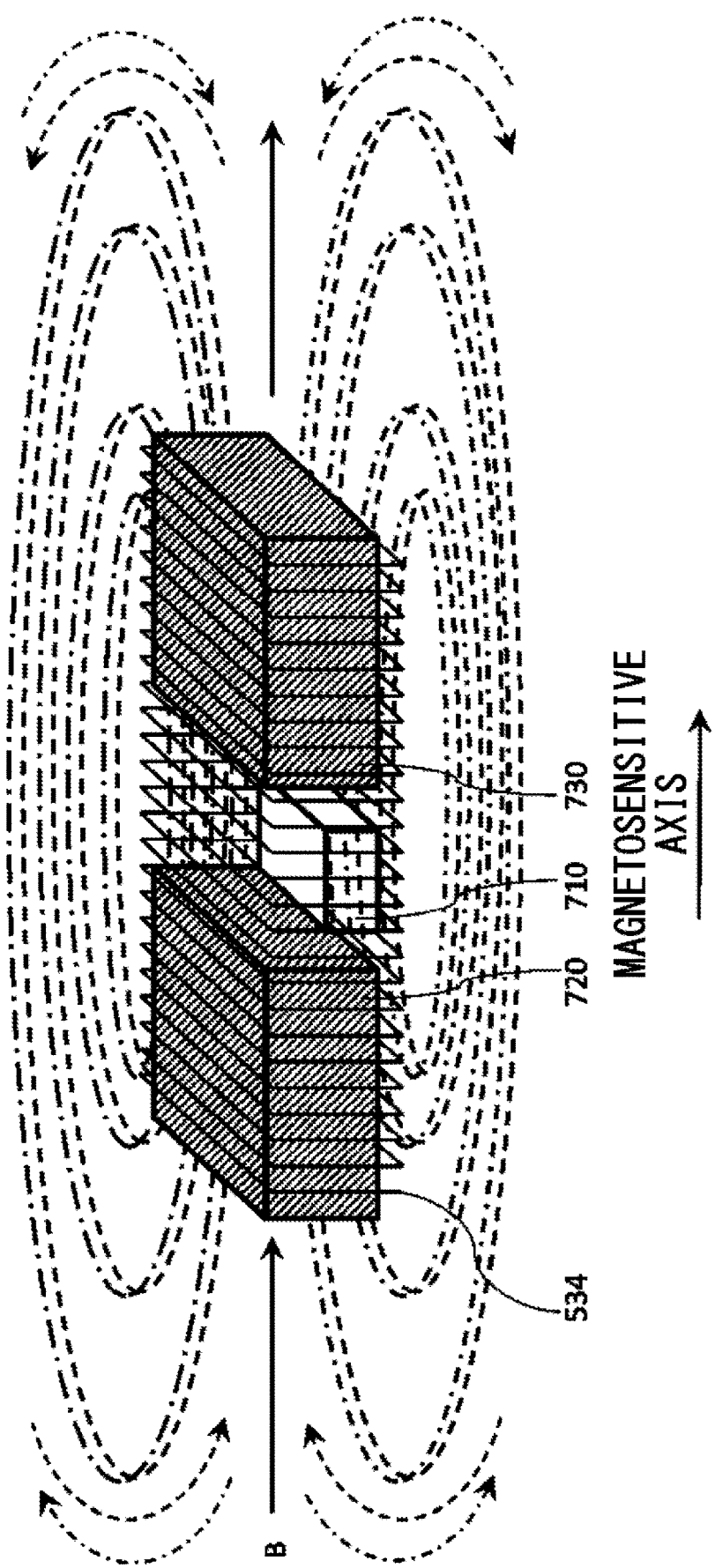
FIG. 8 illustrates a magnetic flux distribution when a feedback magnetic field has been generated in the magnetic sensor 520 according to the present embodiment.

FIG. 8 illustrates a magnetic flux distribution when a feedback magnetic field is generated in the magnetic sensor 520 according to the present embodiment. In FIG. 8, members having the same function and configuration as in FIG. 7 are given the same reference numerals, and the following describes only differing points. In the magnetic sensor 520 according to the present embodiment, when a feedback current is supplied to the first coil 534, a feedback magnetic field is generated by the first coil 534, thereby a magnetic flux distribution is generated as illustrated by a dash-dot line in the present drawing. This magnetic flux generated by the feedback magnetic field has a spatial distribution to cancel out the magnetic field spatial distribution that is magnetically amplified by the magnetic flux concentrators 720 and 730, which is input to the magnetoresistive element 710. Therefore, as shown in the present drawing, when the magnetic flux concentrators 720 and 730 are arranged on both ends of the magnetoresistive element 710, the feedback magnetic field can accurately cancel out the magnetic field distribution at the position of the magnetoresistive element 710, thereby the magnetic sensor 520 can achieve a sensor with high linearity between the input magnetic field and the output voltage.

Figure 9:
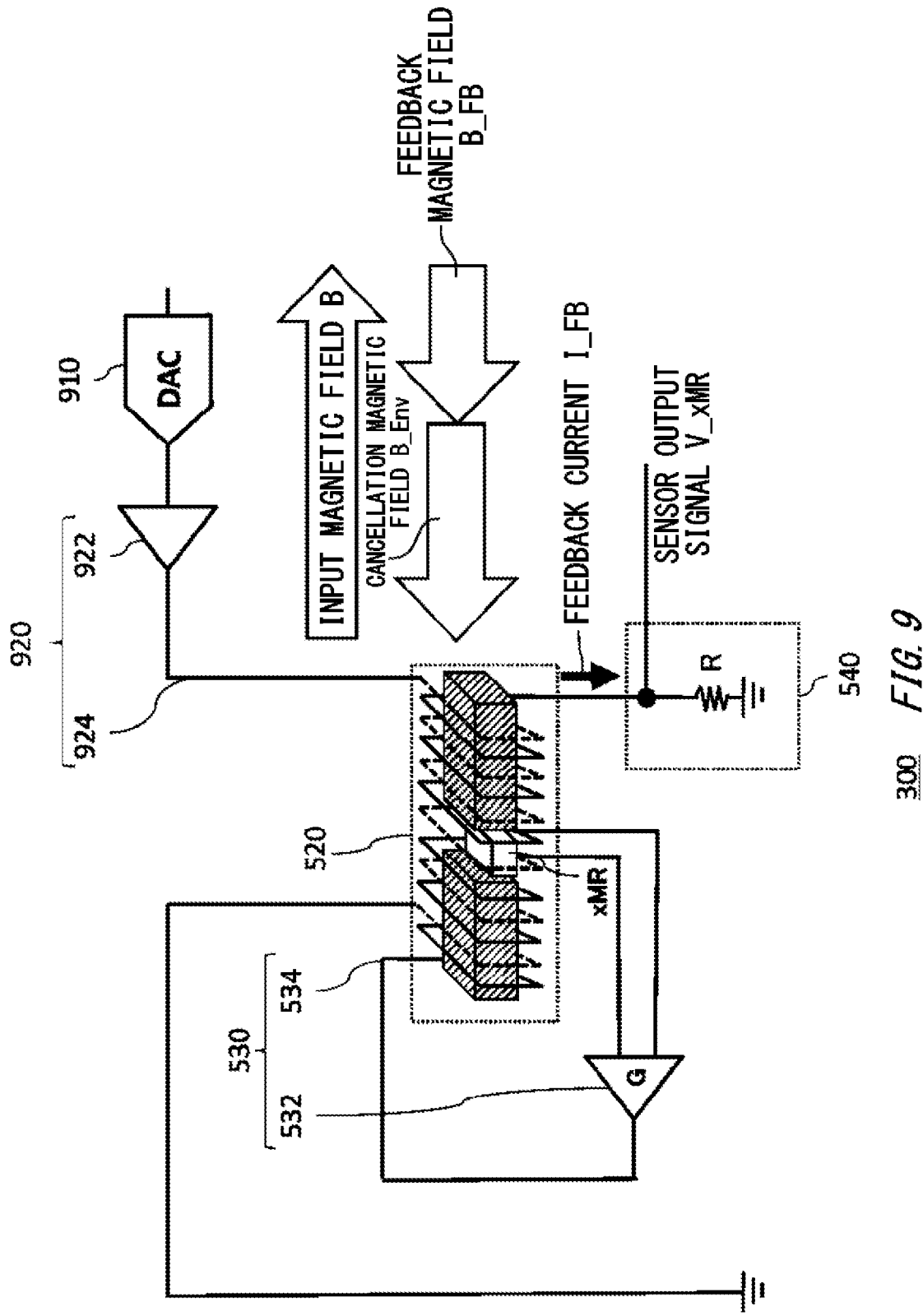
FIG. 9 illustrates another configuration example of the sensor section 300 according to the present embodiment.

FIG. 9 illustrates another configuration example of the sensor section 300 according to the present embodiment. In FIG. 9, members having the same function and configuration as in FIG. 5 are given the same reference numerals, and the following describes only differing points. The sensor section 300 in the present drawing is configured to cancel out an environment magnetic field component that accounts for the majority of the input magnetic field B, and detect the cardiomagnetic component that is a microscopic component included in the input magnetic field B with high resolution from the input magnetic field B. In the present drawing, the sensor section 300 further includes a current DA converter 910 and a second magnetic field generation section 920.

The current DA converter 910 is a DA converter for converting a digital value into an analog current. The current DA converter 910 is configured to accept the detected result of each axis component of the input magnetic field in a digital signal, and supply a current value corresponding to the digital signal to the second magnetic field generation section 920. Herein, for example, the current DA converter 910 may accept the value calculated from an average value of a plurality of X-axis components Bx, which are obtained when the input magnetic field B is detected by the magnetic sensor array 210, as a digital signal of the X-axis components. Similarly, the current DA converter 910 may accept a value calculated from an average value of a plurality of Y-axis components By and a value calculated from an average value of Z-axis components Bz, which are obtained when the input magnetic field B is detected by the magnetic sensor array 210, as a digital signal of the Y-axis components and a digital signal of the Z-axis components, respectively.

The second magnetic field generation section 920 is connected to the current DA converter 910, and is configured to generate a cancellation magnetic field B_Env for reducing an environment magnetic field that accounts for the majority of the input magnetic field B in a magnitude corresponding to the current value supplied from the current DA converter 910, and apply it to the magnetic sensor 520. The second magnetic field generation section 920, for example, is in a direction opposite to the environment magnetic field, and generates a cancellation magnetic field B_Env with an absolute value substantially the same as the environment magnetic field, and operates to cancel out the environment magnetic field. The second magnetic field generation section 920 includes a second amplification circuit 922 and a second coil 924.

The second amplification circuit 922 is connected to the current DA converter 910 and the second coil 924, and outputs a current corresponding to the current value supplied from the current DA converter 910 as a cancellation current I_Comp.

The second coil 924 has one end connected to the second amplification circuit 922, and another end connected to the ground. The second coil 924 is configured to generate a cancellation magnetic field B_Env corresponding to the cancellation current I_Comp supplied from the second amplification circuit 922. The second coil 924 is wrapped along the axial direction of the magnetic field with the magnetic sensor 520 being the detection target, so as to enclose the two magnetic flux concentrators 720 and 730 arranged on both ends of the magnetoresistive element 710 and the magnetoresistive element 710, which are included in the magnetic sensor 520. It is preferable that the second coil 924 generates a uniform cancellation magnetic field B_Env over the entire magnetic sensor 520. For example, when the coil factor of the second coil 924 is referred to as $\beta 2$, the cancellation magnetic field B_Env can be calculated as $\beta 2 \times I\_Comp$. Herein, since the cancellation magnetic field B_Env is generated in the direction for cancelling out the input magnetic field B, the magnetic field input to the magnetic sensor 520 is to be reduced to B-B_Env.

Note that in addition to the first coil 534, when the second coil 924 is wrapped on the magnetoresistive element 710 and the two magnetic flux concentrators 720 and 730 arranged on both ends of the magnetoresistive element 710, two of the first coil 534 and the second coil 924 may be wrapped on the magnetoresistive element 710 and the magnetic flux concentrators 720 and 730 in parallel.

Each of the plurality of magnetic sensor cells 220 may further include a second magnetic field generation section for generating a cancellation magnetic field to reduce the environment magnetic field which is included in the input magnetic field and detected by the magnetic sensor by utilizing the magnetic sensor 520 illustrated in the present drawing as the magnetic sensor 520. Therefore, the magnetic sensor array 210 of the magnetocardiographic measuring apparatus 10 detects a resultant magnetic field for each axial direction, in which the environment magnetic field that accounts for the majority of the input magnetic field B has been cancelled out by the cancellation magnetic field B_Env, thereby can detect the cardiomagnetic component that is a microscopic component of the input magnetic field B with high resolution.

Figure 10:
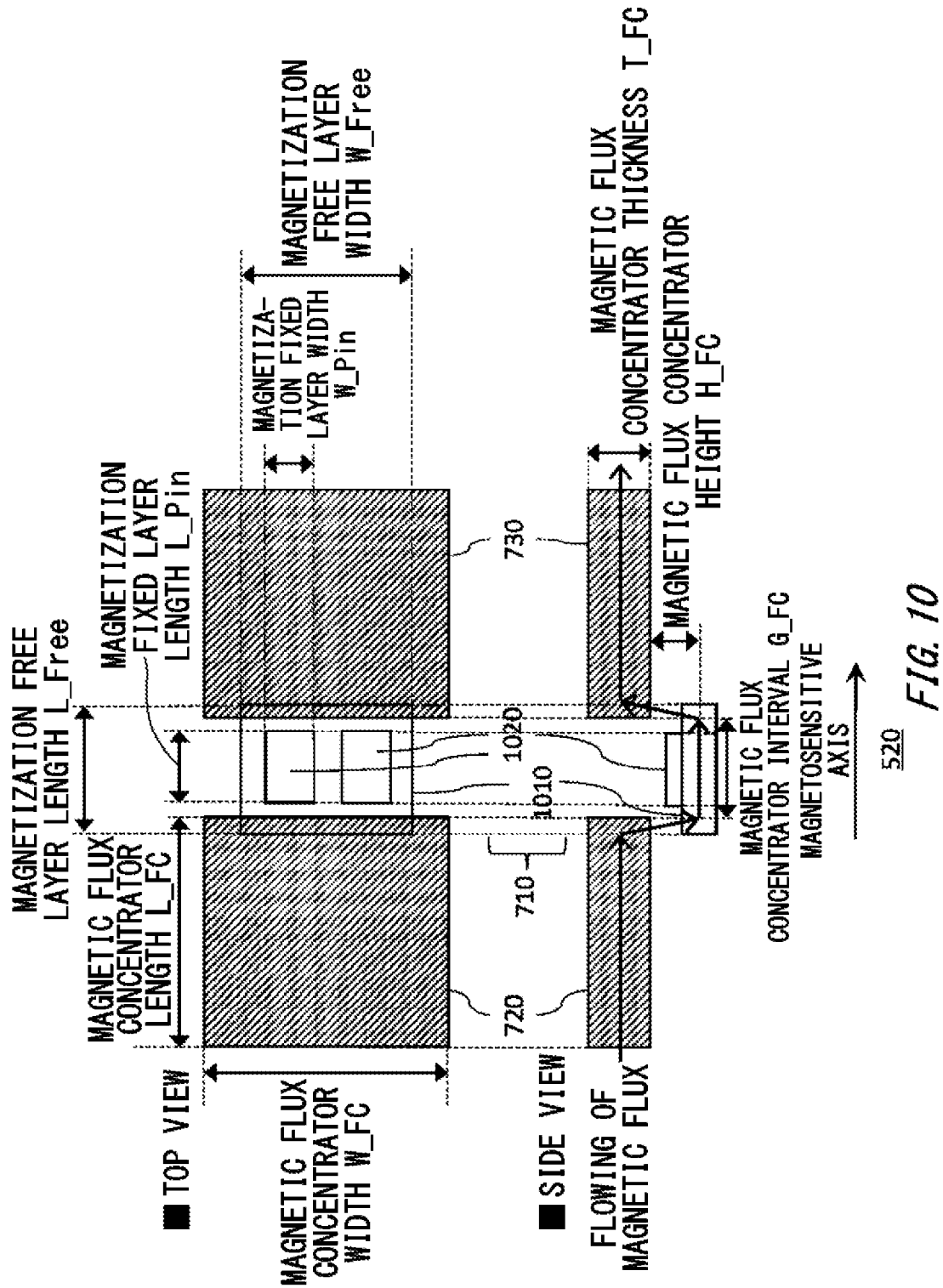
FIG. 10 illustrates a specific example of a configuration of the magnetic sensor 520 according to the present embodiment.

FIG. 10 illustrates a specific example of a configuration of the magnetic sensor 520 according to the present embodiment. In FIG. 10, members having the same function and configuration as in FIG. 7 are given the same reference numerals, and the following describes only differing points. In the present drawing, the magnetoresistive element 710 includes a magnetization free layer 1010 and a magnetization fixed layer 1020. Generally, the magnetoresistive element 710 has a structure in which an insulator thin-film-layer is sandwiched between two ferromagnetic layers. The magnetization free layer 1010 is a layer with the magnetization direction changing corresponding to the external magnetic field of the two ferromagnetic layers. Also, the magnetization fixed layer 1020 is a layer with the magnetization direction not changing relative to the external magnetic field of the two ferromagnetic layers.

In the present specific example, the magnetoresistive element 710 is a magnetoresistive element with a so-called bottom-free structure in which the magnetization free layer 1010 is arranged at the bottom and the magnetization fixed layer 1020 is arranged above the magnetization free layer 1010 via an insulator thin-film-layer (not illustrated in the drawings). Since the magnetoresistive element with a bottom free structure can form a magnetization free layer 1010 in a relatively larger area, it can obtain a high magnetic sensitivity.

Also, in the present specific example, the magnetic sensor 520 has the magnetic flux concentrators 720 and 730 arranged at both ends of the magnetoresistive element 710 via an insulating layer (not illustrated in the drawings) above the magnetoresistive element 710 so as to sandwich the magnetoresistive element 710 in the center. Therefore, the magnetoresistive element 710 is arranged in a narrow space sandwiched between the magnetic flux concentrators 720 and 730.

Herein, in the present drawing, the length along the magnetosensitive axis direction in the magnetization free layer 1010 is defined as the magnetization free layer length L_Free. Also, the length along the axis perpendicular to the magnetosensitive axis direction in the magnetization free layer 1010 in a top view is defined as the magnetization free layer width W_Free. Also, the length along the magnetosensitive axis direction in the magnetization fixed layer 1020 is defined as the magnetization fixed layer length L_Pin. Also, the length along the axis perpendicular to the magnetosensitive axis direction in the magnetization fixed layer 1020 in a top view is defined as the magnetization fixed layer width W_Pin. Also, the length along the magnetosensitive axis direction from one end outside the magnetic flux concentrator to one end outside the magnetization free layer (in the present drawing, the length along the magnetosensitive axis direction from the left end to the right end of the magnetic flux concentrator 720, and the length along the magnetosensitive axis direction from the right end to the left end of the magnetic flux concentrator 730) is defined as the magnetic flux concentrator length L_FC. Also, the length along the axis perpendicular to the magnetosensitive axis direction in the magnetic flux concentrator in a top view is defined as the magnetic flux concentrator width W_FC. Also, the length along the axis perpendicular to the magnetosensitive axis direction in the magnetic flux concentrator in a side view is defined as the magnetic flux concentrator thickness T_FC. Also, the interval along the magnetosensitive axis direction of the two magnetic flux concentrators 720 and 730 (in the present drawing, the length along the magnetosensitive axis direction from the right end of the magnetic flux concentrator 720 to the left end of the magnetic flux concentrator 730) is defined as the magnetic flux concentrator interval G_FC. Also, the interval along the axis perpendicular to the magnetosensitive axis direction, in a side view, from the center of the thickness direction of the magnetization free layer 1010 to the bottom surface of the magnetic flux concentrator, is defined as the magnetic flux concentrator height H_FC.

Figure 11:
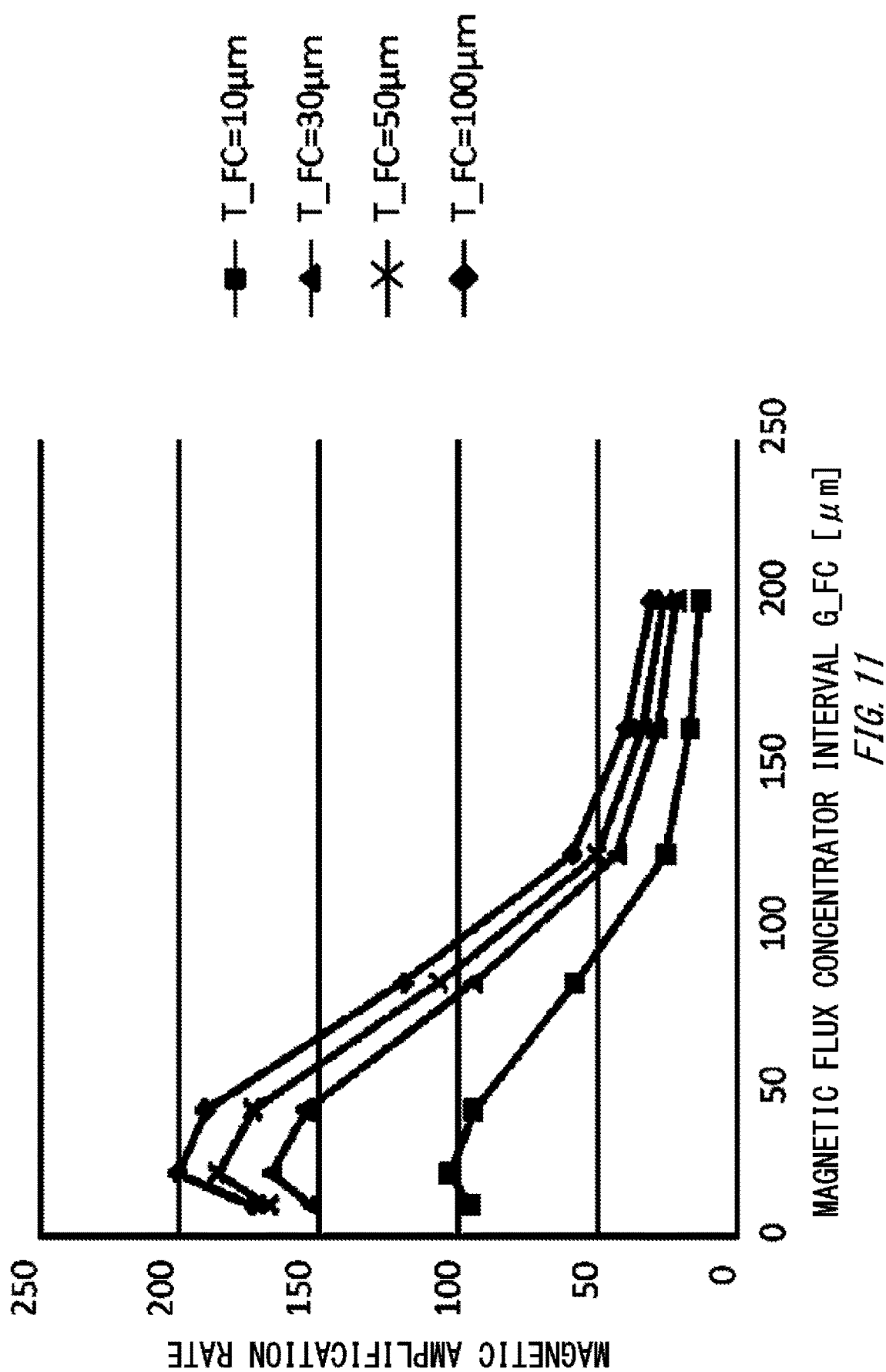
FIG. 11 illustrates simulation results of a magnetic amplification rate in a case where a magnetic flux concentrator interval G_FC has been changed in the magnetic sensor 520 according to the present specific example.

FIG. 11 illustrates simulation results of the magnetic amplification rate when the magnetic flux concentrator interval G_FC has been changed in the magnetic sensor 520 according to the present specific example. In the present drawing, the horizontal axis indicates the magnetic flux concentrator interval G_FC in the unit of μm, and the vertical axis indicates the magnetic amplification rate. Herein, in the present simulation, the magnetization free layer length L_Free is 100 μm, the magnetization free layer width W_Free is 140 μm, the magnetization fixed layer length L_Pin is 40 μm, the magnetization fixed layer width W_Pin is 20 μm, the magnetic flux concentrator width W_FC is 300 μm, and the magnetic flux concentrator height H_FC is 0.6 μm. All of these parameters were assumed to be common values in the simulations shown below. In the present simulation, a simulation has been further performed, in which the magnetic flux concentrator length L_FC is 10 mm, the magnetic flux concentrator thickness T_FC is 10 μm, 30 μm, 50 μm and 100 μm.

As illustrated in the present drawing, the magnetic amplification rate of the magnetic sensor 520 becomes higher as the magnetic flux concentrator interval G_FC is narrowed. Herein, since the magnetization free layer length L_Free is 100 μm, when the magnetic flux concentrator interval G_FC is 100 μm, the side of the magnetic flux concentrator and the side of the magnetization free layer 1010 are aligned in a side view (that is, in FIG. 10, the right end of the magnetic flux concentrator 720 and the left end of the magnetization free layer 1010, and the left end of the magnetic flux concentrator 730 and the right end of the magnetization free layer 1010 are aligned in a side view). According to the results of the present simulation, the magnetic amplification rate of the magnetic sensor 520 becomes further higher when the magnetic flux concentrator interval G_FC is less than 100 μm. Accordingly, it is preferable that the interval between the magnetic flux concentrators along the magnetosensitive axis direction of 720 and 730 arranged on both ends of the magnetoresistive element 710 (the magnetic flux concentrator interval G_FC) is less than the length in the magnetosensitive axis direction of the magnetization free layer 1010 of the magnetoresistive element 710 (the magnetization free layer length L_Free), thereby the magnetic sensor 520 can obtain a higher magnetic amplification rate. Also, the magnetic sensor 520 may have the magnetic flux concentrator interval G_FC less than the magnetization fixed layer length L_Pin (40 μm). That is, the magnetic sensor 520 may arrange the magnetic flux concentrator so that the magnetic flux concentrator is partially overlapped with the magnetization fixed layer in a top view.

Figure 12:
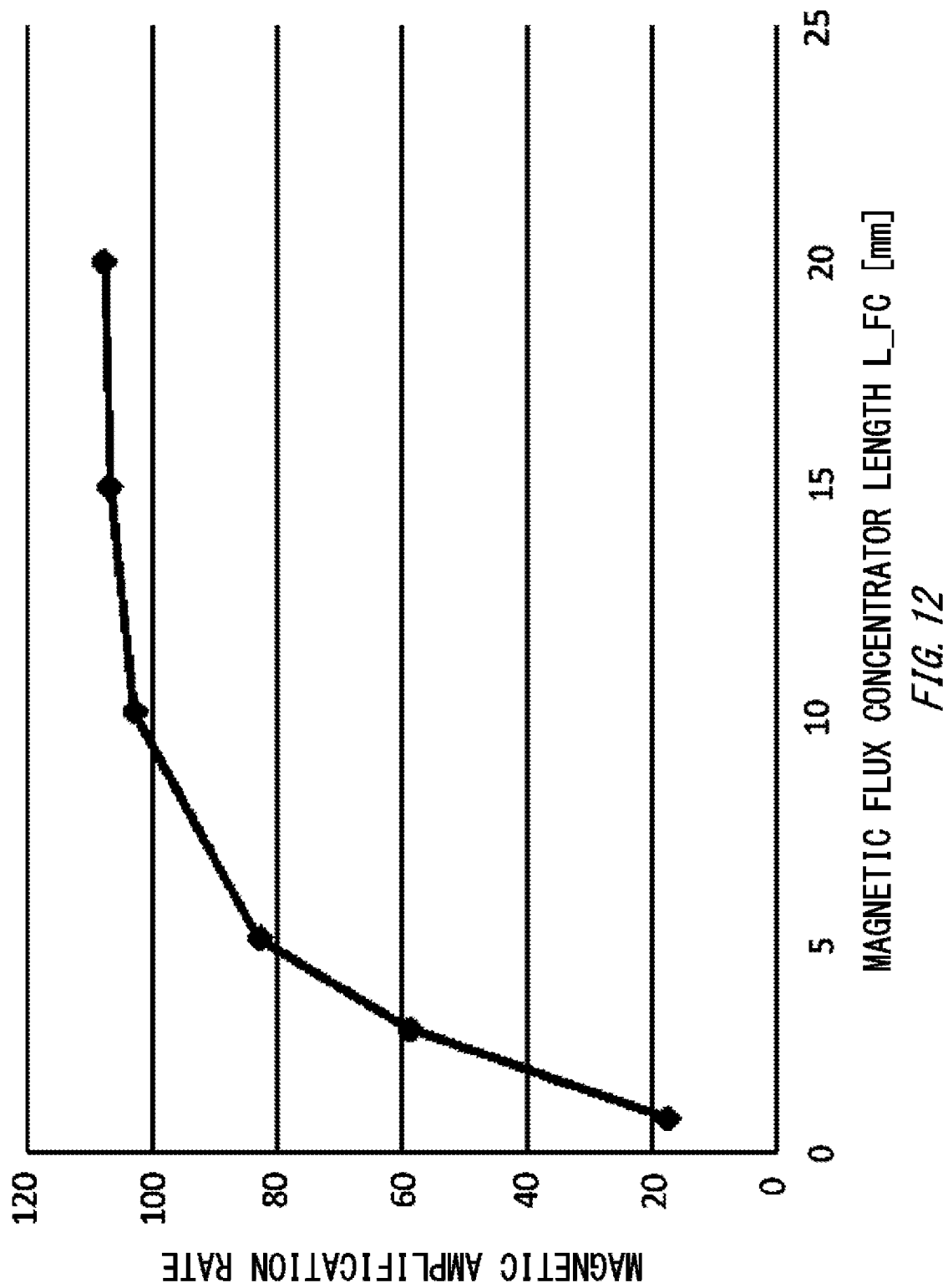
FIG. 12 illustrates simulation results of the magnetic amplification rate in a case where a magnetic flux concentrator length L_FC has been changed in the magnetic sensor 520 according to the present specific example.

FIG. 12 illustrates simulation results of the magnetic amplification rate in a case where a magnetic flux concentrator length L_FC has been changed in the magnetic sensor 520 according to the present specific example. In the present drawing, the horizontal axis indicates the magnetic flux concentrator length L_FC in the unit of mm, and the vertical axis indicates the magnetic amplification rate. In the present simulation, a simulation has been performed, in which the magnetic flux concentrator thickness T_FC is 10 μm, and the magnetic flux concentrator interval G_FC is 20 μm.

As illustrated in the present drawing, the magnetic amplification rate of the magnetic sensor 520 becomes higher as the magnetic flux concentrator length L_FC becomes longer. This can be said to be because the longer the magnetic flux concentrator, which is formed of a material with high magnetic permeability, the more magnetic flux it generates. Accordingly, for the magnetic sensor 520, in providing the magnetic flux concentrator at both ends of the magnetoresistive element 710, it is preferable to increase the length of the magnetic flux concentrator along the magnetosensitive axis direction (magnetic flux concentrator length L_FC) as much as possible in terms of design, so that a higher magnetic amplification rate can be obtained. Specifically, the length of the magnetic flux concentrator along the magnetosensitive axis direction (magnetic flux concentrator length L_FC) is preferably 1 mm or more, so that a higher magnetic amplification effect can be obtained. In particular, as illustrated in the present drawing, the magnetic sensor 520 is highly effective in increasing the magnetic amplification rate in the range where the magnetic flux concentrator length L_FC is less than 10 mm. Also, if the magnetic flux concentrator length L_FC is 10 mm or more, a magnetic amplification rate of 100 times or more can be obtained. Accordingly, in a magnetocardiographic measurement, in order to detect the weak cardiac magnetic field more accurately, the length of the magnetic flux concentrator along the magnetosensitive axis direction (magnetic flux concentrator length L_FC) is preferably 10 mm or more.

Figure 13:
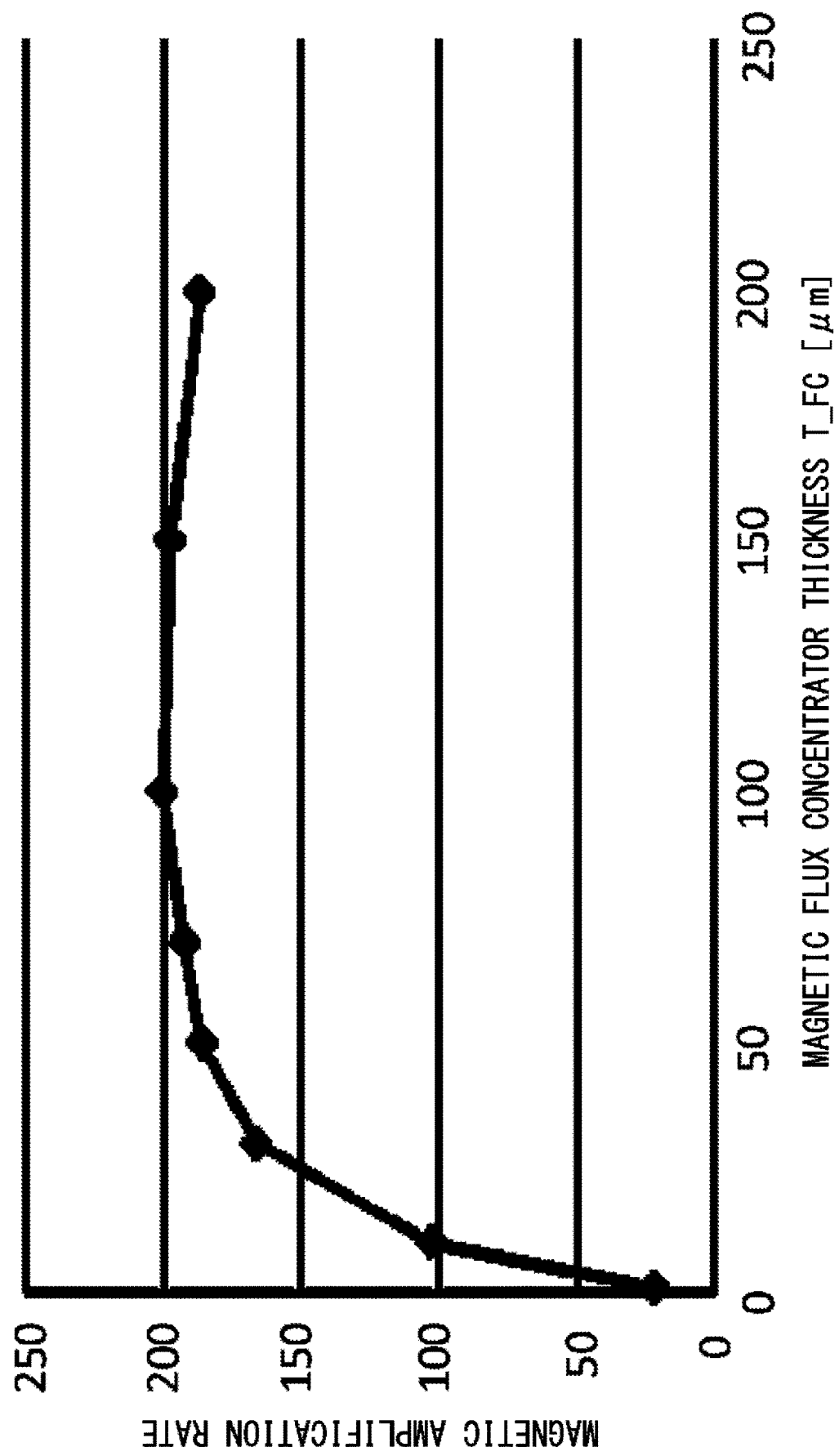
FIG. 13 illustrates simulation results of the magnetic amplification rate in a case where a magnetic flux concentrator thickness T_FC has been changed in the magnetic sensor 520 according to the present specific example.

FIG. 13 illustrates simulation results of the magnetic amplification rate in a case where a magnetic flux concentrator thickness T_FC has been changed in the magnetic sensor 520 according to the present specific example. In the present drawing, the horizontal axis indicates the magnetic flux concentrator thickness T_FC in the unit of μm, and the vertical axis indicates the magnetic amplification rate. In the present simulation, a simulation has been performed, in which the magnetic flux concentrator length L_FC is 10 mm, the magnetic flux concentrator thickness T_FC is 10 μm, and the magnetic flux concentrator interval G_FC is 20 μm.

As illustrated in the present drawing, for the magnetic sensor 520, as the magnetic flux concentrator thickness T_FC is increased, the magnetic amplification rate tends to increase up to a certain point, and then the magnetic amplification rate tends to decrease. This is because, up to a certain point, the thicker the magnetic flux concentrator formed of a material with high magnetic permeability is, the more magnetic flux is generated, and thus the magnetic amplification rate increases, but after exceeding a certain point, the center of the thickness direction of the magnetic flux concentrator moves away from the magnetoresistive element 710 rather than the magnetic amplification effect, and the magnetic flux converged by the magnetic flux concentrator has a stronger effect of becoming difficult to pass through the magnetoresistive element 710. Accordingly, the thickness of the magnetic flux concentrator (the magnetic flux concentrator thickness T_FC) is preferably kept within approximately 100 μm, so that a higher magnetic amplification effect can be obtained.

Figure 14:
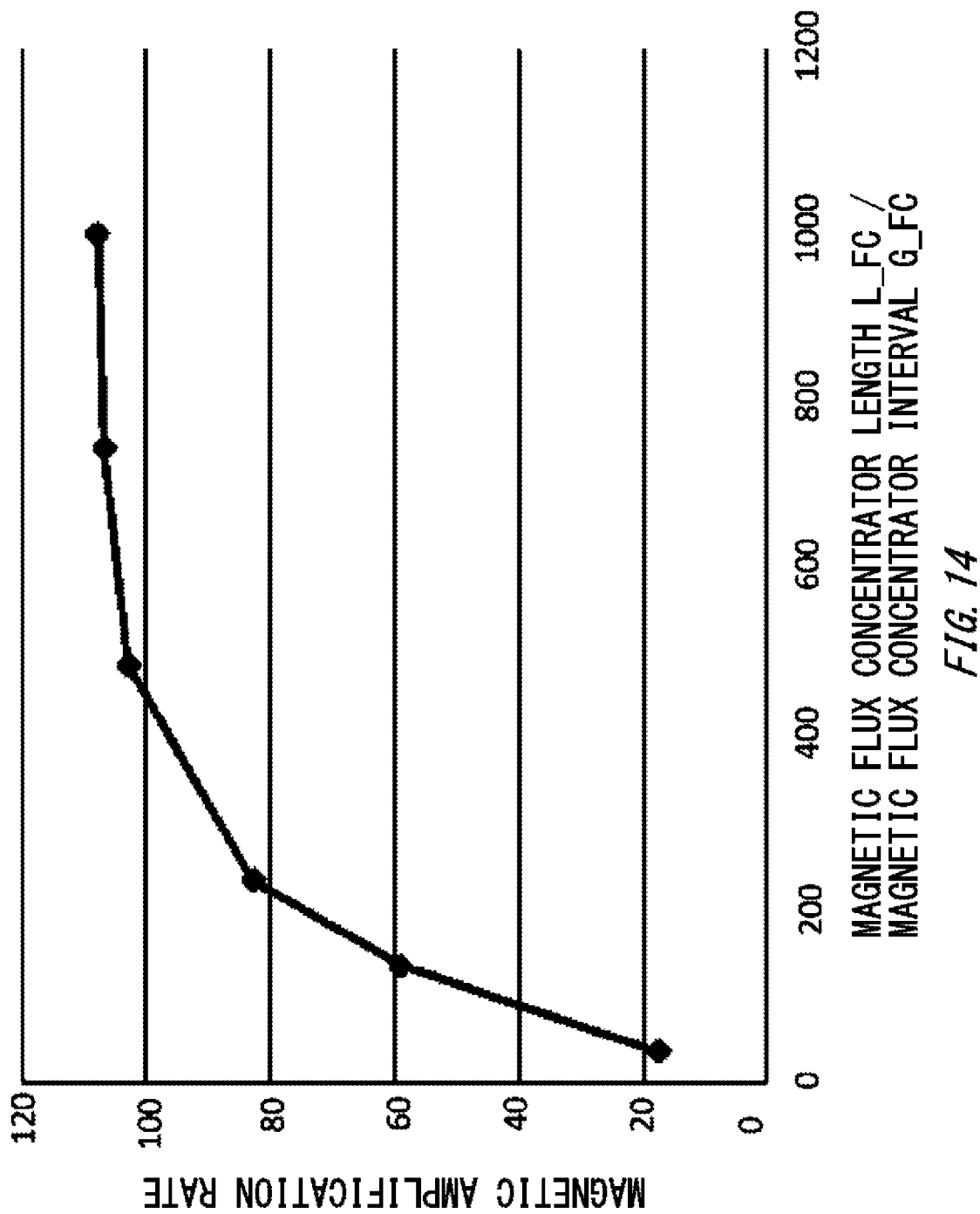
FIG. 14 illustrates simulation results of the magnetic amplification rate in a case where a magnetic flux concentrator interval G_FC is constant, and a magnetic flux concentrator length L_FC or a magnetic flux concentrator interval G_FC has been changed, in the magnetic sensor 520 according to the present specific example.

FIG. 14 illustrates simulation results of the magnetic amplification rate in a case where a magnetic flux concentrator interval G_FC is constant, and a magnetic flux concentrator length L_FC or a magnetic flux concentrator interval G_FC has been changed, in the magnetic sensor 520 according to the present specific example. In the present drawing, the horizontal axis indicates a value of the magnetic flux concentrator length L_FC divided by the magnetic flux concentrator interval G_FC, and the vertical axis indicates the magnetic amplification rate. In the present simulation, a simulation has been performed, in which the magnetic flux concentrator thickness T_FC is 10 μm, and the magnetic flux concentrator interval G_FC is 20 μm.

As illustrated in FIG. 14, for the magnetic sensor 520, the magnetic amplification rate increases as the magnetic flux concentrator length L_FC or the magnetic flux concentrator interval G_FC increases. This can be said to reflect the fact that the smaller the magnetic flux concentrator G_FC is in FIG. 11, the higher the magnetic amplification rate becomes, and the longer the magnetic flux concentrator length L_FC is in FIG. 12, the higher the magnetic amplification rate becomes. As illustrated in the present drawing, for the magnetic sensor 520, the length of the magnetic flux concentrator along the magnetosensitive axis direction (the magnetic flux concentrator length L_FC) is preferably greater than 10 times of the interval between the magnetic flux concentrators along the magnetosensitive axis direction 720 and 730 arranged on both ends of the magnetoresistive element 710 (the magnetic flux concentrator interval G_FC), so that a higher magnetic amplification effect can be obtained. In particular, for the magnetic sensor 520, the interval between the magnetic flux concentrators along the magnetosensitive axis direction 720 and 730 arranged on both ends of the magnetoresistive element 710 (the magnetic flux concentrator interval G_FC) is preferably less than the length in the magnetosensitive axis direction of the magnetization free layer 1010 of the magnetoresistive element 710 (the magnetization free layer length L_Free), and the length of the magnetic flux concentrator along the magnetosensitive axis direction (the magnetic flux concentrator length L_FC) is preferably greater than 10 times of the length in the magnetosensitive axis direction of the magnetization free layer 1010 of the magnetoresistive element 710, so that a higher magnetic amplification effect can be obtained. Furthermore, for the magnetic sensor 520, it is shown that the magnetic flux concentrator interval G_FC is preferably less than 100 μm when the magnetization free layer length is 100 μm based on the simulation results of FIG. 11, and the is preferably 10 mm or more based on the simulation results of FIG. 12, thus the length of the magnetic flux concentrator along the magnetosensitive axis direction (the magnetic flux concentrator length L_FC) is preferably 100 times or more of the interval between the magnetic flux concentrators along the magnetosensitive axis direction 720 and 730 arranged on both ends of the magnetoresistive element 710 (the magnetic flux concentrator interval G_FC), so that a higher magnetic amplification rate can be obtained. In this way, for the magnetic sensor 520, by appropriately designing the magnetic flux concentrator length L_FC and the magnetic flux concentrator interval G_FC, a high magnetic amplification rate can be achieved.

Figure 15:
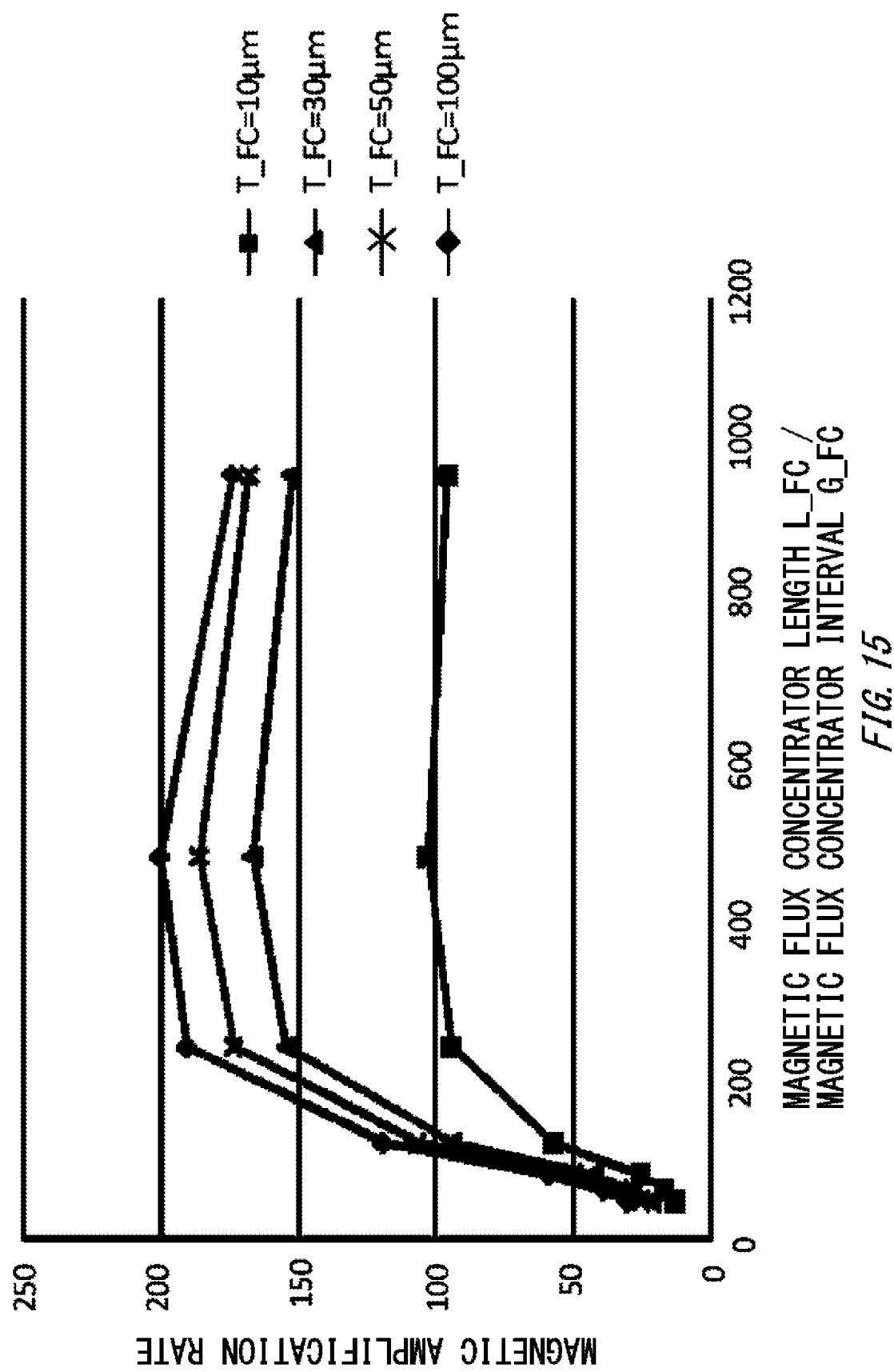
FIG. 15 illustrates simulation results of the magnetic amplification rate in a case where the magnetic flux concentrator length L_FC is constant, and the magnetic flux concentrator length L_FC or the magnetic flux concentrator interval G_FC has been changed, in the magnetic sensor 520 according to the present specific example.

FIG. 15 illustrates simulation results of the magnetic amplification rate in a case where the magnetic flux concentrator length L_FC is constant, and the magnetic flux concentrator length L_FC or the magnetic flux concentrator interval G_FC has been changed, in the magnetic sensor 520 according to the present specific example. In the present drawing, the horizontal axis indicates a value of magnetic flux concentrator length L_FC divided by the magnetic flux concentrator interval G_FC, and the vertical axis indicates the magnetic amplification rate. In the present simulation, a simulation has been performed, in which the magnetic flux concentrator length L_FC is 10 mm, and the magnetic flux concentrator thickness T_FC is 10 μm, 30 μm, 50 μm and 100 μm.

Figure 16:
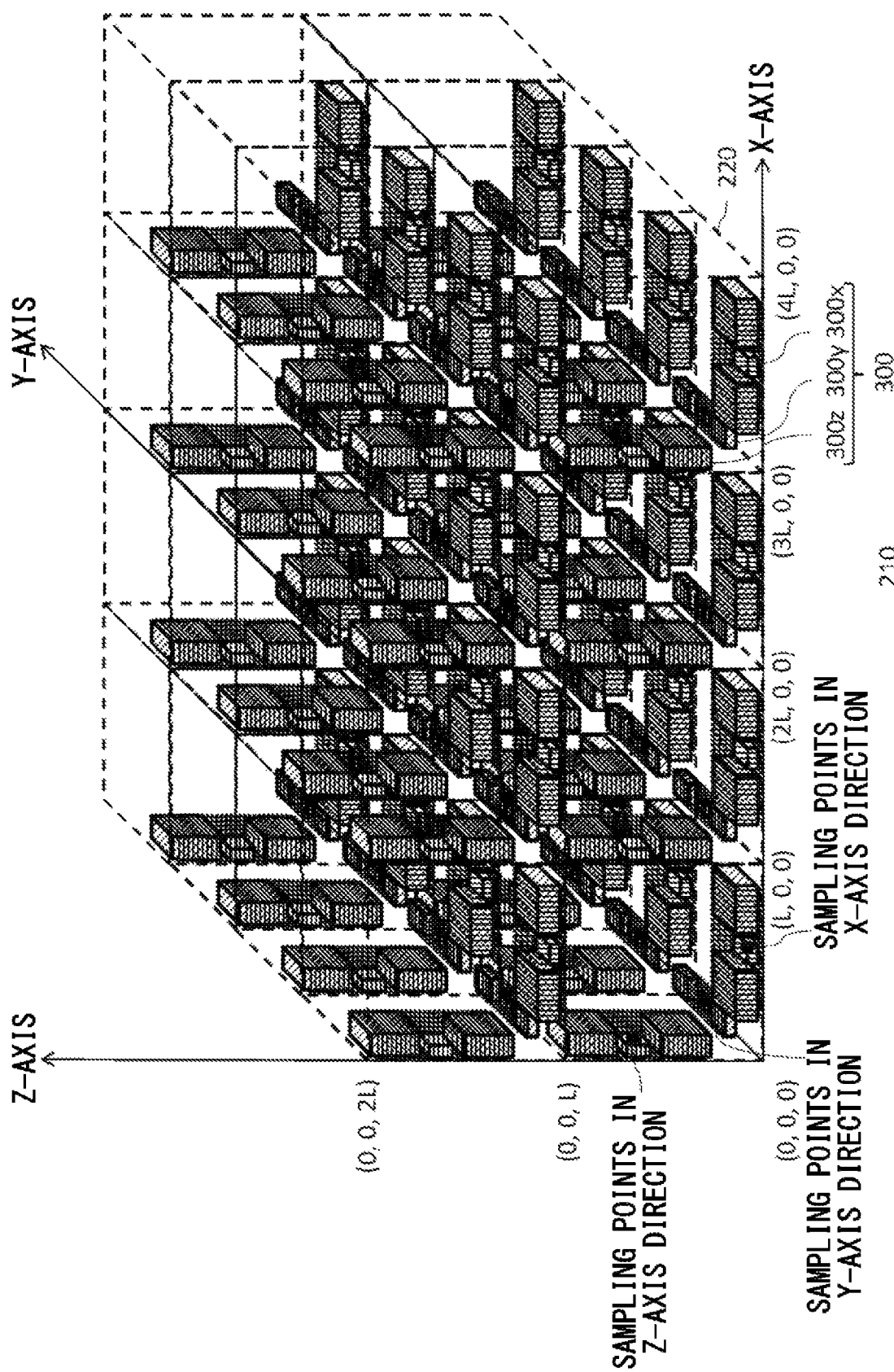
FIG. 16 illustrates an example of applying the magnetic sensor 520 according to the present embodiment to the sensor sections 300 of a plurality of magnetic sensor cells 220 in the magnetic sensor array 210.

FIG. 16 illustrates an example of applying the magnetic sensor 520 according to the present embodiment to the sensor sections 300 of a plurality of magnetic sensor cells 220 in the magnetic sensor array 210. In FIG. 16, members having the same function and configuration as in FIG. 3 are given the same reference numerals, and the following describes only differing points. In the present drawing, the plurality of magnetic sensor cells 220 use the magnetic sensors 520 according to the configuration example illustrated in FIG. 7 as magnetic sensors 520 in the three sensor sections 300x, 300y and 300z. For the plurality of magnetic sensor cells 220, by using the magnetic sensor 520 with the magnetic flux concentrators 720 and 730 arranged on both ends of the magnetoresistive element 710 in each of the sensor sections 300, the above-mentioned magnetic amplification effect can be obtained, and the spatial sampling points can be clarified at the same time.

Also, for the magnetocardiographic measuring apparatus 10, by using the magnetic sensor 520 with the magnetic flux concentrator length L_FC and the magnetic flux concentrator interval G_FC optimized as the magnetic sensor 520 in each sensor section 300 of the plurality of magnetic sensor cells 220, a magnetic amplification rate exceeding, for example, 100 times, can be achieved, and in the magnetocardiographic measurement, the weak cardiac magnetic field can be more accurately detected.

Furthermore, as illustrated in the present drawing, the sensor sections 300x, 300y and 300z, which are magnetic sensors of the three axes in the plurality of magnetic sensor cells 220, do not overlap each other when viewed from each of the three-dimensional directions of the X-axis, Y-axis, and Z-axis, and are arranged with one end provided in a gap provided between the magnetic sensors of the three axes and the other end extended in each axial direction of the three axial directions away from the gap. As one example, in the present drawing, an air space (gap) is provided at the lower left corner portion in front view of the magnetic sensor cell 220, and the sensor sections 300x, 300y and 300z are shown in the example, respectively with one end provided contacting the air space and with another end arranged extending in each axial direction of the X-axis, the Y-axis and the Z-axis direction to be away from the air space. As illustrated in the present drawing, the coil or the magnetic body included in the sensor sections 300x, 300y and 300z are preferably arranged not to overlap each other, so that the following points can be achieved. First, by arranging the coil or the magnetic body not to overlap each other, the sampling points can be further clarified, and each component of the magnetic field can further become easier to understand. Also, the cross-axis sensitivities of the sensor sections 300x, 300y and 300z can be regarded as equivalent to each other, thus the calibration operations in linear algebra become easier. Note that the cross-axis sensitivities are caused by mutual interference by the coil or magnetic body included in the sensor sections 300x, 300y and 300z. By such a configuration of each sensor section 300 of the plurality of magnetic sensor cells 220, the magnetocardiographic measuring apparatus 10 is capable of detecting the weak cardiac magnetic field more accurately in a magnetocardiographic measurement. As another example, the sensor sections 300x, 300y and 300z may be provided without providing a gap at the corner portion of the magnetic sensor cell 220. In this case, the magnetic sensor cell 220 can be configured to be smaller, thereby a magnetic sensor array 210 having such a plurality of magnetic sensor cells 220 can be miniaturized.

Also, in the magnetic sensor array 210, a plurality of magnetic sensor cells 220 are arranged in a manner that places them in the closest proximity to each other. In the magnetocardiographic measuring apparatus, the adjacent magnetic sensor cells 220 are preferably arranged close to each other for detecting an electrical activity in the heart by measuring the cardiac magnetic field spatial distribution. For example, when used in the diagnosis of ischemic heart failure or the like, the interval between the sensor sections adjacent in the magnetosensitive axis direction (L in the present drawing) is preferably 3 cm or less to obtain the required space resolution.

In order to obtain a high magnetic sensitivity even in such a limited interval, the sensor sections 300 of the plurality of magnetic sensor cells 220 are preferably have the length of the magnetic flux concentrator along the magnetosensitive axis direction L_FC to be as large as possible. More detailly, the magnetic sensor 520 in each sensor section 300 is preferably designed to make the sum of the lengths of the two magnetic flux concentrators along the magnetosensitive axis direction and the interval between the two magnetic flux concentrators along the magnetosensitive axis direction become greater than half of the interval between the sensor sections adjacent in the magnetosensitive axis direction (that is, satisfy 2× magnetic flux concentrator length L_FC+ magnetic flux concentrator interval G_FC>0.5×L), so that a high magnetic sensitivity can be obtained even in a limited interval.

Generally, if each sensor section 300 is arranged close to each other in this way, the mutual magnetic interference between each 3-axis sensor becomes not negligible, but with the magnetocardiographic measuring apparatus 10 according to the present embodiment, not only the magnetic sensitivity error of each 3-axis sensor itself (mismatch of main axis sensitivity in X, Y, and Z axes, and cross-axis sensitivities), as described below, but also the magnetic interference from the adjacent sensor sections can be corrected.

Figure 17:
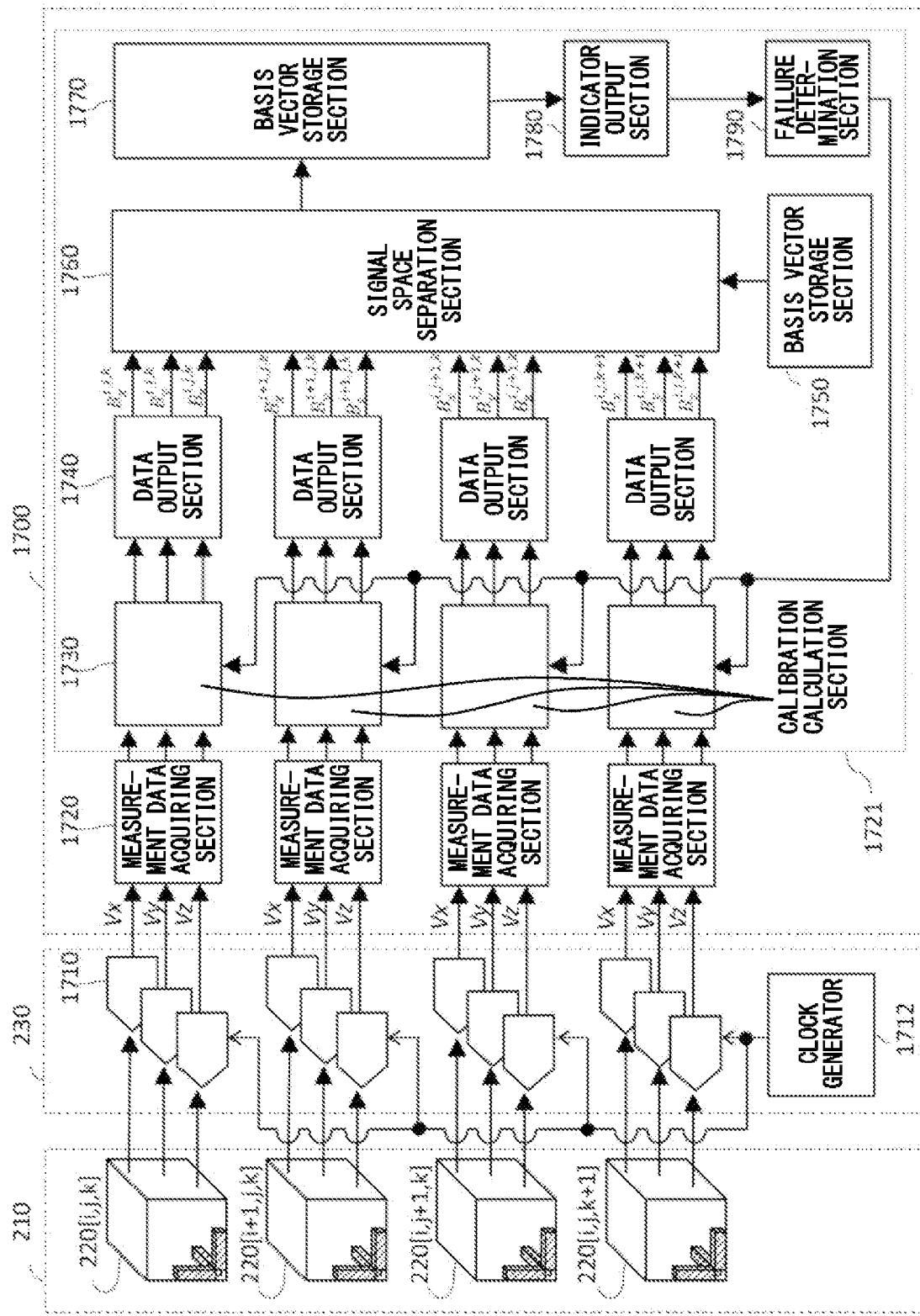
FIG. 17 illustrates a configuration of the magnetic sensor array 210, a sensor data gathering section 230 and a sensor data processing section 1700 according to the present embodiment.

FIG. 17 illustrates a configuration of the magnetic sensor array 210, a sensor data gathering section 230 and a sensor data processing section 1700 according to the present embodiment.

The magnetic sensor array 210 includes a plurality of magnetic sensor cells 220. Each of the plurality of magnetic sensor cells 220 may include a plurality of sensor sections 300x to 300z as mentioned above. In the present drawing, among the plurality of magnetic sensor cells 220 included in the magnetic sensor array 210 in each dimensional direction, the portions relating to the positions [i, j, k], [i+1, j, k], [i, j+1, k], and [i, j, k+1] are illustrated.

The sensor data gathering section 230 includes a plurality of AD converters 1710 and clock generators 1712. The plurality of AD converters 1710 are provided corresponding to each of the plurality of sensor sections 300x to 300z of the magnetic sensor cell 220, and convert an analog detection signal (sensor output signal V_xMR in FIG. 6) output by the corresponding sensor section 300 into a digital measurement data V (Vx,Vy,Vz). Herein, the Vx, Vy and Vz are measurement values (for example, digital voltage values) obtained by converting the detection signals to digital from the sensor sections 300x, 300y, and 300z.

The clock generator 1712 generates a sampling clock and supplies a common sampling clock to each of the plurality of AD converters 1710. Then, each of the plurality of AD converters 1710 performs AD conversion according to the common sampling clock supplied from the clock generator 1712. Thus, the plurality of AD converters 1710 all operate in synchronization to perform AD conversion on the respective outputs from the 3-axis sensor sections 300x to 300z provided at different positions. This enables the plurality of AD converters 1710 to simultaneously sample the detection results from the 3-axis sensor sections 300x to 300z provided in different spaces.

The sensor data processing section 1700 includes a plurality of measurement data acquiring sections 1720 provided corresponding to each of the plurality of magnetic sensor cells 220, and a measurement data computing section 1721. The measurement data computing section 1721 includes a plurality of calibration calculation sections 1730, a plurality of data output sections 1740, a basis vector storage section 1750, a signal space separation section 1760, an indicator calculation section 1770, an indicator output section 1780 and a failure determination section 1790.

The measurement data acquiring section 1720 is configured to acquire the measurement data based on the input magnetic field including a to-be-measured magnetic field (for example, a cardiac magnetic field generated by an electrical activity of the heart). The measurement data acquiring section 1720 is connected to three AD converters 1710 that are respectively connected to the corresponding magnetic sensor cell 220, and configured to acquire the measurement data respectively measured by the sensor sections 300x to 300z within the plurality of magnetic sensor cells 220 constituting the magnetic sensor array 210. Specifically, the measurement data acquiring section 1720 may be configured by using the flip-flop or the like for latching the measurement data V (Vx,Vy,Vz) at a predetermined timing T that are converted to digital by the AD converter 1710.

The measurement data computing section 1721 is configured to calibrate the measurement data that are acquired by the measurement data acquiring section 1720. For example, the calibration calculation section 1730 is connected to the measurement data acquiring section 1720, and is configured to calibrate the measurement data that are acquired by the measurement data acquiring section 1720 by using the calibration parameter. An overview of the calibration for the measurement data performed by the calibration calculation section 1730 is as follows. The magnetic field input to the magnetic sensor cell 220 at the position [i, j, k] is referred to as B ($B_x, B_y, B_z$), and the detection result of the 3-axis magnetic sensor detected by the sensor sections 300x, 300y and 300z are referred to as the measurement data V (Vx, Vy,Vz). In this case, when the magnetic sensor characteristic of the 3-axis magnetic sensor is referred to as the 3-axis sensor magnetic sensitivity matrix S, the detection result V of the 3-axis magnetic sensor can be shown as shown in the following expression.

$$\begin{pmatrix} Vx \\ Vy \\ Vz \end{pmatrix} = \qquad\qquad\text{[Expression 4]}$$

-continued $$S\begin{pmatrix}Bx\\By\\Bz\end{pmatrix}+\begin{pmatrix}Vos,x\\Vos,y\\Vos,z\end{pmatrix}=\begin{pmatrix}Sxx & Sxy & Sxz\\Syx & Syy & Syz\\Szx & Szy & Szz\end{pmatrix}\begin{pmatrix}Bx\\By\\Bz\end{pmatrix}+\begin{pmatrix}Vos,x\\Vos,y\\Vos,z\end{pmatrix}$$

Herein, Sxx, Syy and Szz respectively indicates the sensitivity of the main axis direction of the sensor sections 300x, 300y and 300z, and Sxy, Sxz, Syx, Syz, Szx and Szy respectively indicates the sensitivity of cross-axis directions. Also, "Vos, x", "Vos, y" and "Vos, z" respectively indicates the main axis direction offset of the sensor sections 300x, 300y and 300z.

Since each of the sensor sections 300 has a linearity of detection results for the input magnetic field in the range of the input magnetic field to be detected, each element of the 3-axis sensor magnetic sensitivity matrix S is an substantially constant coefficient that is independent of the magnitude of the input magnetic field B. Also, even if the sensor section 300 has cross-axis sensitivities, if the detection results of the sensor section 300 have linearity, each element of the 3-axis sensor magnetic sensitivity matrix S becomes an substantially constant coefficient that is independent of the magnitude of the input magnetic field B.

Accordingly, the calibration calculation section 1730 can convert the measurement data V (Vx,Vy,Vz) to the magnetic field measurement data B ($B_x$,$B_y$,$B_z$) indicating originally input magnetic field, as shown in the following expression, by using the inverse matrix S−1 of the 3-axis sensor magnetic sensitivity matrix S and the offset ("Vos,x", "Vos,y", "Vos,z"). Note that this conversion can be also true even when the sensor sections 300x to 300z have the magnetic flux concentrators described above. This is because the magnetic sensor cell 220 is configured as a 3-axis magnetic sensor using the sensor sections 300x to 300z, and because conversion using linear algebra can be performed.

$$\begin{pmatrix}Bx\\By\\Bz\end{pmatrix}=S^{-1}\left\{\begin{pmatrix}Vx\\Vy\\Vz\end{pmatrix}-\begin{pmatrix}Vos,x\\Vos,y\\Vos,z\end{pmatrix}\right\}$$ [Expression 5]

The calibration calculation section 1730 is configured to calculate the inverse matrix S−1 of the 3-axis sensor magnetic sensitivity matrix S and the offset ("Vos,x", "Vos,y", "Vos,z") using the environment magnetic field measurement data), and convert the measurement data V acquired by the measurement data acquiring section 1720 to the magnetic field measurement data B using these calibration parameter, and supply it to the data output section 1740.

As described above, since each of the sensor sections 300 has linearity, the calibration calculation section 1730 can convert the measurement data V to the magnetic field measurement data B by using a substantially constant coefficient. That is, the substantially constant coefficients used by the calibration calculation sections 1730 can be defined as a set of calibration parameters using the environment magnetic field data.

The data output section 1740 supplies the magnetic field measurement data B, calibrated by the calibration calculation section 1730, to the signal space separation section 1760.

The basis vector storage section 1750 prestores basis vectors required for the signal space separation section 1760 to perform signal separation on the magnetic field measurement data B, and supplies the basis vectors to the signal space separation section 1760.

The signal space separation section 1760 performs the signal separation on the input magnetic field spatial distribution indicated by the magnetic field measurement data B generated from the measurement data V, for example, by the magnetic field measurement data B generated by the calibration calculation section 1730 calibrating the measurement data V. The signal vectors output by each of the magnetic sensors 520 when the magnetic sensor array 210 has detected the magnetic field having the spatial distribution of the orthonormal functions are taken as the basis vectors. In this case, the signal space separation section 1760 acquires the basis vectors required for the signal separation from the basis vector storage section 1750. Then, the signal space separation section 1760 uses the basis vectors obtained from the basis vector storage section 1750 to signal-separate the magnetic field spatial distribution indicated by the magnetic field measurement data B into the cardiac magnetic field, which is a to-be-measured magnetic field, and the disturbance magnetic field, and calculates the cardiac magnetic field by suppressing the disturbance magnetic field, and outputs it.

The indicator calculation section 1770 calculates the indicator ε, which indicates the calibration accuracy in the measurement data computing section 1721, for example, the calibration calculation section 1730. The indicator calculation section 1770 is connected to the signal space separation section 1760, and calculates the indicator ε based on the results of signal separation performed by the signal space separation section 1760. This will be described below.

The indicator output section 1780 is connected to the indicator calculation section 1770, and is configured to output the indicator ε calculated by the indicator calculation section 1770. In this case, the indicator output section 1780 may, for example, display the indicator ε on the display section, or may supply the indicator ε to other apparatuses via a network. Also, the indicator output section 1780 is configured to supply the indicator ε to the failure determination section 1790 as illustrated in the present drawing.

The failure determination section 1790 is configured to determine the failure of the magnetocardiographic measuring apparatus 10 based on the indicator ε calculated by the indicator calculation section 1770.

Figure 18:
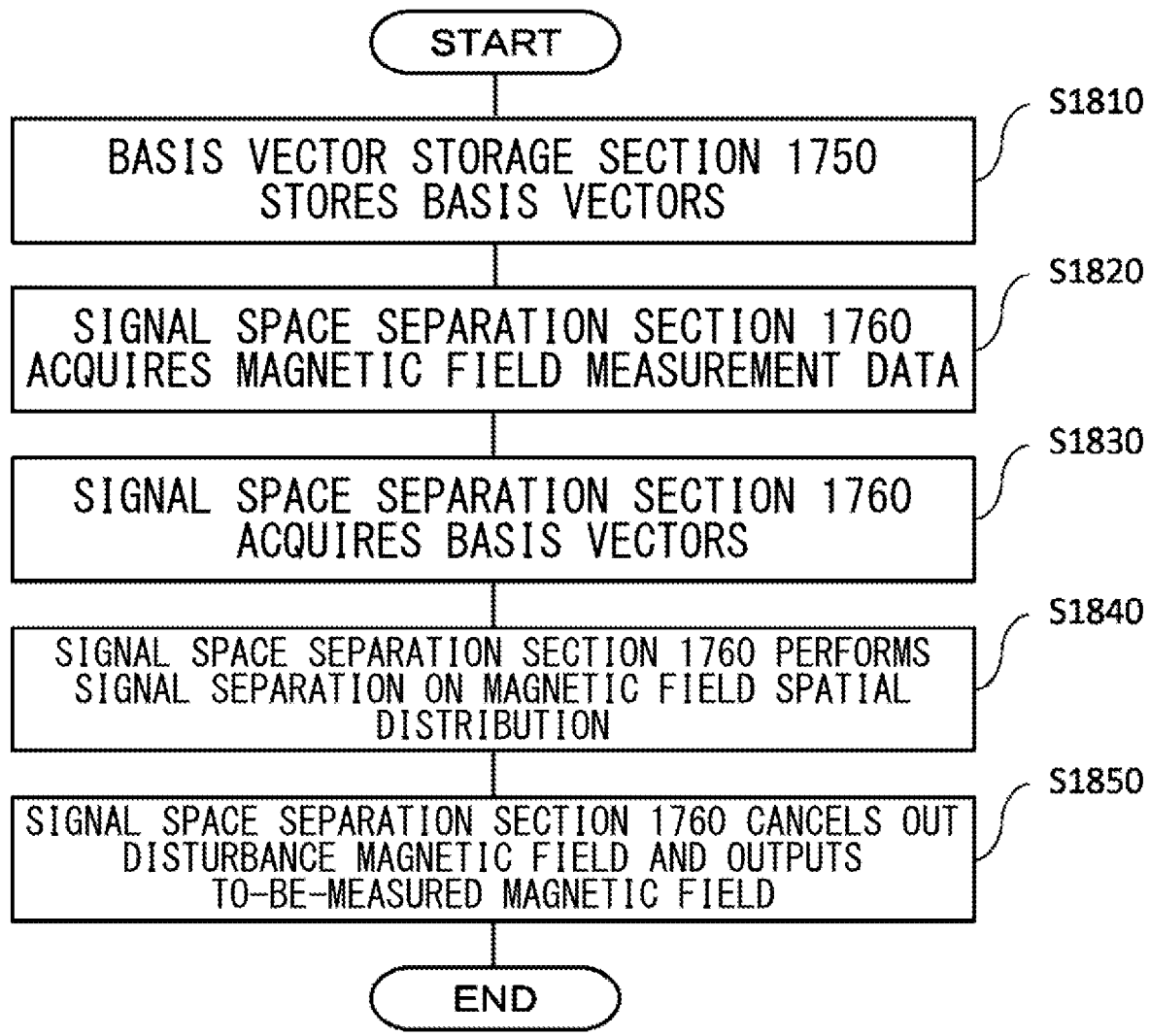
FIG. 18 illustrates a flow of signal separation performed on a magnetic field spatial distribution by the magnetocardiographic measuring apparatus 10 according to the present embodiment.

FIG. 18 illustrates a flow of signal separation performed on a magnetic field spatial distribution by the magnetocardiographic measuring apparatus 10 according to the present embodiment. In step 1810, the basis vector storage section 1750 is configured to store the basis vectors. As one example, before a measurement of the cardiac magnetic field, the basis vector storage section 1750 is configured to store the signal vectors, which is output by each of the plurality of magnetic sensors 520 when a magnetic field with a spatial distribution of spherical harmonics has been detected by the magnetic sensor array 210, as the basis vectors. That is, the basis vector storage section 1750 stores, as the basis vectors, magnetic field signal vectors obtained by spatially sampling the spherical harmonics when a predetermined point in a space is identified as the coordinate origin. Herein, the spherical harmonics are functions obtained by restricting, to a unit sphere, the homogeneous polynomial that is a solution to an n-dimensional Laplace equation, and has orthonormality on the sphere. Note that in the present drawing, a case is shown as one example, where step 1810, in which the basis vector storage section 1750 stores the basis vectors, is taken as the initial step in the flow of the signal separation performed by the magnetocardiographic measuring apparatus 10 on the magnetic field spatial distribution. However, the basis vector storage section 1750 may store the basis vectors in advance before the flow of the signal separation performed by the magnetocardiographic measuring apparatus 10 on the magnetic field spatial distribution. Furthermore, the basis vector storage section 1750 may store, as the basis vectors, signal vectors predetermined from a simulation result or the like.

Next, in step 1820, the signal space separation section 1760 acquires the magnetic field measurement data B measured by the magnetic sensor array 210 and calibrated by the calibration calculation section 1730, from the data output section 1740.

Further, in step 1830, the signal space separation section 1760 acquires the signal vectors stored as the basis vectors in the basis vector storage section 1750 in step 1810, from the basis vector storage section 1750. Note that in this flow, either of step 1820 or step 1830 may be performed before the other.

In step 1840, the signal space separation section 1760 performs series expansion of the magnetic field spatial distribution indicated by the magnetic field measurement data B acquired in step 1820, using the signal vectors acquired in step 1830 as the basis vectors. Then, the signal space separation section 1760 signal-separates the magnetic field spatial distribution from the vectors obtained by series expansion into the to-be-measured magnetic field and the disturbance magnetic field. Note that the orthonormal functions may be a spherical harmonics. Also, the signal space separation section 1760 calculates the coefficients of the basis vectors using the least-squares method during the signal separation.

Then, in step 1850, the signal space separation section 1760 is configured to suppress the disturbance magnetic field, calculate and output only the cardiac magnetic field that is the to-be-measured magnetic field based on the result of signal separation in steps 1840, and end the process. This will be described in detail below.

The static magnetic field B(r) is obtained as the spatial gradient of the potential V(r), using the potential V(r) satisfying the Laplace equation $\Delta \cdot V(r)=0$, as shown in the following expression. Herein, r represents a position vector representing the position with respect to the coordinate origin, $\Delta$ represents a Laplacian, $\mu$ represents magnetic permeability, and $\nabla$ represents an operator representing vector derivative operations.

$$B(r) = -\mu \cdot \nabla \cdot V(r) \quad \text{[Expression 6]}$$

Then, generally, a solution to the Laplace equation is a solution in a form of series expansion using spherical harmonics $Y_{l,m}(\theta,\varphi)$ which are functions of an orthonormal function system, and thus the potential V(r) can be expressed as in the following expression. Herein, in the expression, |r| represents an absolute value (the distance from the coordinate origin) of the position vector r, $\theta$ and $\varphi$ represent two declinations of spherical coordinate, l represents an azimuthal quantum number, m represents a magnetic quantum number, $\alpha$ and $\beta$ represent multipole moments, and Lin and Lout are respectively the number of series for the space in front of and the space behind the magnetic sensor array 210, respectively, as viewed by the subject. The azimuthal quantum number l is a positive integer, and the magnetic quantum number m is an integer in a range from $-1$ to $+1$. In other words, when l is 1, for example, m is $-1$, 0, and 1, and when l is 2, for example, m is $-2$, $-1$, 0, 1, and 2. Note that since there is no case of a single magnetic pole in the magnetic field, the azimuthal quantum number l starts from 1 instead of 0 in Expression 7. The first term in Expression 7 is a term inverse proportional to a distance from the coordinate origin, and represents a potential in the space in front in the magnetic sensor array 210 as viewed from the subject. Also, the second term in Expression 7 is a term proportional to a distance from the coordinate origin, and represents a potential in the farther space in the magnetic sensor array 210 as viewed from the subject.

$$V(r) = \sum_{l=1}^{Lin} \sum_{m=-l}^{l} \alpha_{l,m} \cdot \left( \frac{1}{|r|^{l+1}} \cdot Y_{l,m}(\theta, \phi) \right) + \quad \text{[Expression 7]}$$

$$\sum_{l=1}^{Lout} \sum_{m=-l}^{l} \beta_{l,m} \cdot \left( |r|^l \cdot Y_{l,m}(\theta, \phi) \right)$$

Therefore, according to Expression 6 and Expression 7, the static magnetic field B(r) can be expressed by the expression below. Herein, the first term in Expression 8 represents the magnetic field source that exists in the space in front of the magnetic sensor array 210 as viewed by the subject, that is, the cardiac magnetic field generated by the electrical activity of the heart (the to-be-measured magnetic field). Also, the second term in Expression 8 represents the disturbance magnetic field generated by the magnetic field source in the farther space in the magnetic sensor array 210 as viewed from the subject.

$$B(r) = -\mu \sum_{l=1}^{Lin} \sum_{m=-l}^{l} \alpha_{l,m} \cdot \nabla \left( \frac{1}{|r|^{l+1}} \cdot Y_{l,m}(\theta, \phi) \right) - \quad \text{[Expression 8]}$$

$$\mu \sum_{l=1}^{Lout} \sum_{m=-l}^{l} \beta_{l,m} \cdot \nabla \left( |r|^l \cdot Y_{l,m}(\theta, \phi) \right)$$

When the solution to the Laplace equation is expressed in a form of series expansion using the spherical harmonics, the general solution of such will be infinite series, but what needs to be obtained is a sufficient signal-to-noise ratio SNR, (which is a ratio of the to-be-measured magnetic field signal to the disturbance magnetic field and sensor noise) for measuring a biomagnetic field, which is regarded as being actually sufficiently expressible with a series of approximately 10 terms. Furthermore, it is said that approximately Lin=8 and Lout=3 is sufficient for a series of signal space separations in magnetoencephalography. Accordingly, in the present embodiment, a case in which Lin=8, Lout=3 is described as one example. However, the Lin and Lout values are not limited to this, and may be any numerical values that are sufficient for only suppressing the disturbance magnetic field and calculating the to-be-measured magnetic field.

Figure 29:
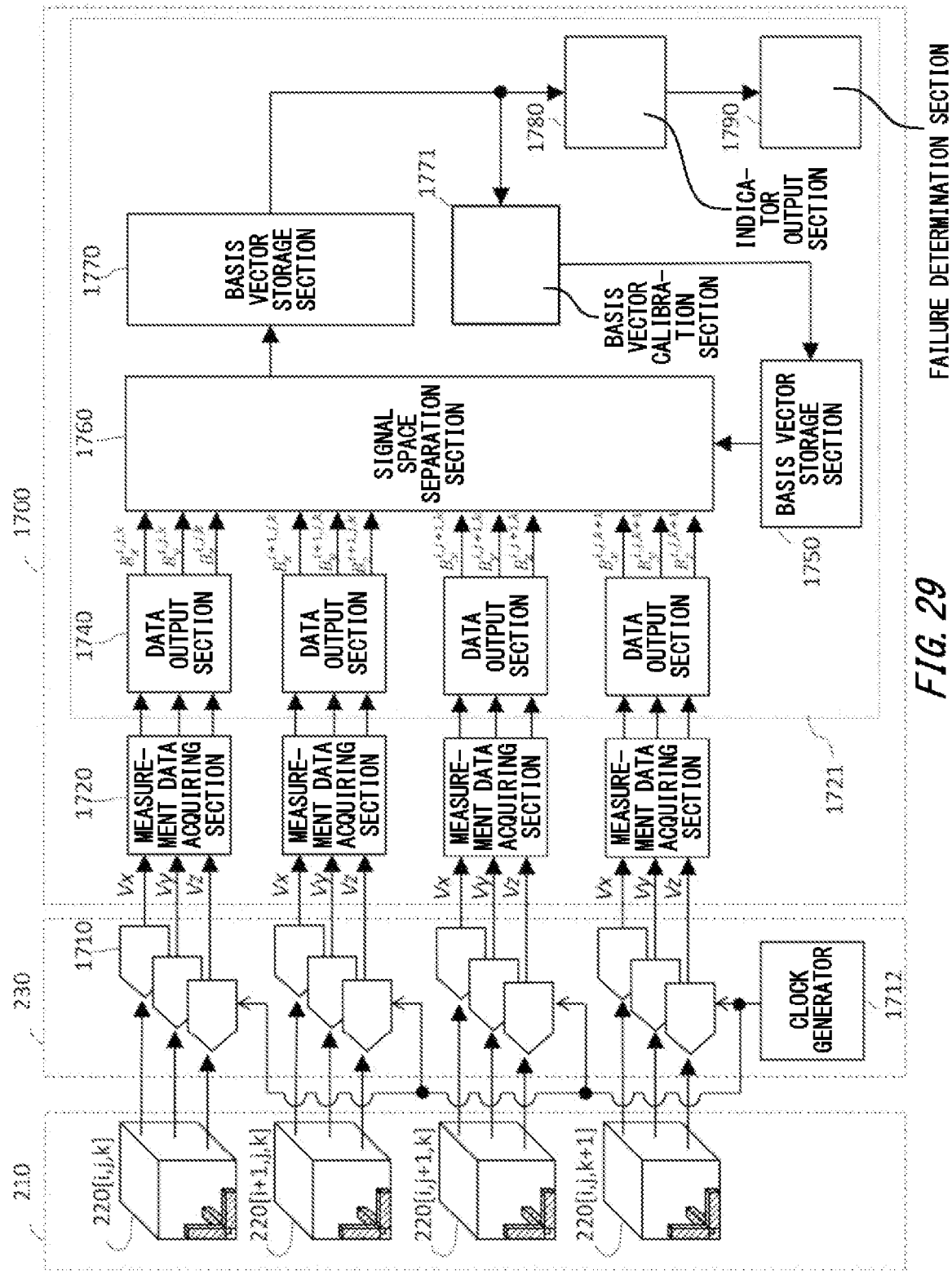
FIG. 29 illustrates a variation of the magnetic sensor array 210, the sensor data gathering section 230 and the sensor data processing section 1700 shown in FIG. 17.

Herein, the vectors representing the magnetosensitive axis direction and magnetic sensitivity of the sensor sections 300x, y, and z in each magnetic sensor cell 220 are nx, ny, and nz, respectively, and $a_{l,m}$ and $b_{l,m}$ are defined as the following expression with the subscript t as the transposing matrix. That is, $a_{l,m}$ and $b_{l,m}$ are defined as vectors that have as their components the inner product of nx, ny, nz, each vector of which represents the magnetosensitive axis direction and the magnetic sensitivity of the sensor sections 300x, y, and z, and the spherical harmonics, which is a three-dimensional vector signal. This means that in each magnetic sensor cell 220, the spherical harmonics are sampled in a Cartesian coordinate system. Note that the $a_{l,m}$ and $b_{l,m}$ are vectors with dimensions equal to the number of magnetic sensor cells 220 multiplied by three. Also, the respective vectors nx, ny, and nz, which represent the magnetosensitive axis direction and the magnetic sensitivity of each of the sensor sections 300, may be the vectors corresponding to the sensitivity in the main axis direction and the sensitivity in the cross-axis direction described above. nx may correspond to Sxx, Sxy and Sxz. ny may correspond to Syx, Syy and Syz. nz may correspond to Szx, Szy and Szz. For example, as the variation illustrated in FIG. 29, the measurement data computing section 1721 may include the basis vector calibration section 1771 instead of the calibration calculation section 1730. In such a configuration, the basis vector calibration section 1771 calibrates the basis vectors by calculating al,m and bl,m based on the indicator ε calculated by the indicator calculation section 1770, including the sensitivity correction in the main axis direction and the sensitivity correction in the cross-axis direction of the sensor sections 300x, y, and z, and the basis vector storage section 1750 stores the calibrated basis vectors $a_{l,m}$ and $b_{l,m}$. The signal space separation section 1760 of the magnetocardiographic measuring apparatus 10 according to the present variation uses the calibrated basis vectors, $a_{l,m}$ and $b_{l,m}$, stored in the basis vector storage section 1750 during operation to signal-separate the magnetic field spatial distribution indicated by the magnetic field measurement data B into a cardiac magnetic field that is a to-be-measured magnetic field and a disturbance magnetic field, and suppress the disturbance magnetic field and calculate the cardiac magnetic field, then output it as described above. The cardiac magnetic field calculated in this way is corrected for the magnetic sensitivity (main axis sensitivity and cross-axis sensitivity) of each magnetic sensor cell 220.

$$a_{l,m} = -\mu \cdot \left[\nabla\left(\frac{1}{r^{l+1}} \cdot Y_{l,m}(\theta, \phi)\right)\right]^t \cdot \begin{bmatrix} nx \\ ny \\ nz \end{bmatrix} \quad \text{[Expression 9]}$$

$$b_{l,m} = -\mu \cdot \left[\nabla\left(r^l \cdot Y_{l,m}(\theta, \phi)\right)\right]^t \cdot \begin{bmatrix} nx \\ ny \\ nz \end{bmatrix}$$

Then, the sensor output vector Φ output by each magnetic sensor cell 220 at certain timing can be expressed by the following expression.

$$\Phi = \sum_{l=1}^{Lin} \sum_{m=-l}^{l} \alpha_{l,m} \cdot a_{l,m} + \sum_{l=1}^{Lout} \sum_{m=-l}^{l} \beta_{l,m} \cdot b_{l,m} \quad \text{[Expression 10]}$$

Furthermore, Sin, Sout, Xin, and Xout are each defined in the following manner. That is, Sin is defined as vector of total Lin·(Lin+2) column in which each vector a at each integer timing of l, from m=−l to m=l, is arrayed in column sequentially from l=1 to l=Lin. Furthermore, Sout is defined as vector of total Lout·(Lout+2) column in which each vector b at each integer timing of l, from m=−l to m=l, is arrayed in column sequentially from l=1 to l=Lout. Further, Xin is defined as a vector of total Lin·(Lin+2) row obtained by transposing a vector in which each multipole moment α at each integer timing of l, from m=−l to m=l, is arrayed in column sequentially from l=1 to l=Lin. Further, Xout is defined as a vector of total Lout·(Lout+2) row obtained by transposing a vector in which each multipole moment S at each integer timing of l, from m=−l to m=l, is arrayed in column sequentially from l=1 to l=Lin.

$Sin=[a_{1,-1}a_{1,0}a_{1,+1} \ldots a_{Lin,Lin}]$ $Sout=[b_{1,-1}b_{1,0}b_{1,+1} \ldots b_{Lout,Lout}]$ $xin=[\alpha_{1,-1}\alpha_{1,0}\alpha_{1,+1} \ldots \alpha_{Lin,Lin}]^t$ $xout=[\beta_{1,-1}\beta_{1,0}\beta_{1,+1} \ldots \beta_{Lout,Lout}]^t$ [Expression 11]

Then, the sensor output vector Φ can be expressed in the form of the inner product of the basis vector matrix S and the column vector X, as shown in the following expression. Herein, the basis vector matrix S indicates the basis vectors, for example, obtained by the signal space separation section 1760 from the basis vector storage section 1750 in step 1830. Also, a column vector X represents coefficients related to the basis vectors.

$$\Phi = S \cdot X = [Sin, Sout] \cdot \begin{bmatrix} Xin \\ Xout \end{bmatrix} \quad \text{[Expression 12]}$$

In step 1840, the signal space separation section 1760 according to the present embodiment uses the following expression based on the model equation of the sensor output vector Φ obtained from Expression 12 to determine the column vector ^X (where "^X" indicates the left side in Expression 13 and means the hat (estimated) value of X) that satisfies Φ=S·X in the least-squares approximation. Thus, the signal space separation section 1760 can solve the magnetic field spatial distribution in step 1840. In this case, the signal space separation section 1760 may issue a warning that the cardiac magnetic field that is the to-be-measured magnetic field cannot be measured with high precision, if the magnitude of the disturbance magnetic field exceeds a predetermined range. This allows the magnetocardiographic measuring apparatus 10 to prevent in advance the measurement of the cardiac magnetic field in situations such as when the apparatus is malfunctioning or when there is a disturbance magnetic field so large that the to-be-measured magnetic field cannot be measured with high accuracy. In this case, the signal space separation section 1760 may, for example, determine that the magnitude of the disturbance magnetic field exceeds the predetermined range when the magnitude of any of the components of ^Xout·Sout exceeds the predetermined threshold value, or may determine that the magnitude of the disturbance magnetic field exceeds the predetermined range when the sum or average of the magnitudes of any of the components of ^Xout·Sout exceeds the predetermined threshold value.

$$\widehat{X} = \begin{bmatrix} \widehat{Xin} \\ \widehat{Xout} \end{bmatrix} = (S^t \cdot S)^{-1} \cdot S^t \cdot \phi \quad \text{[Expression 13]}$$

Then, in step 1850, the signal space separation section 1760 outputs the result of suppressing the disturbance magnetic field component, that is, the component of the second term in Expression 8, by decreasing ^Xout·Sout using the column vector determined in step 1840. The signal space separation section 1760 may suppress the disturbance magnetic field component by outputting only ^Xin·Sin as a result, and output only the cardiomagnetic component, which is the to-be-measured magnetic field, that is, the component of the first term in Expression 8.

This means that, according to the magnetocardiographic measuring apparatus 10 of the present embodiment, the magnetic field spatial distribution indicated by the magnetic field measurement data B measured using the magnetic sensor array 210, which has a plurality of magnetic sensor cells 220 and can detect input magnetic fields in the three axial directions at a plurality of locations in three-dimensional space, can be signal-separated into the to-be-measured magnetic field, the cardiac magnetic field, and the disturbance magnetic field. In addition, the magnetocardiographic measuring apparatus 10 suppresses the disturbance magnetic field component and outputs only the cardiomagnetic component, which allows for more accurate measurement of the cardiac magnetic field. Furthermore, since each of the plurality of sensor sections 300 include magnetic flux concentrators, it is possible to increase the magnetic sensitivity of the sensor sections 300, clarify spatial sampling points, and increase the affinity with signal space separation technology. Furthermore, if the magnetocardiographic measuring apparatus 10 has a calibration calculation section 1730, highly accurate calibration (main axis sensitivity mismatch, cross-axis sensitivities, and offset or the like.) can be achieved, and calibration errors in a plurality of sensor sections 300 can be reduced in the previous step rather than processed in the signal space separation step, so that the to-be-measured magnetic field component can be extracted with higher accuracy.

Figure 19:
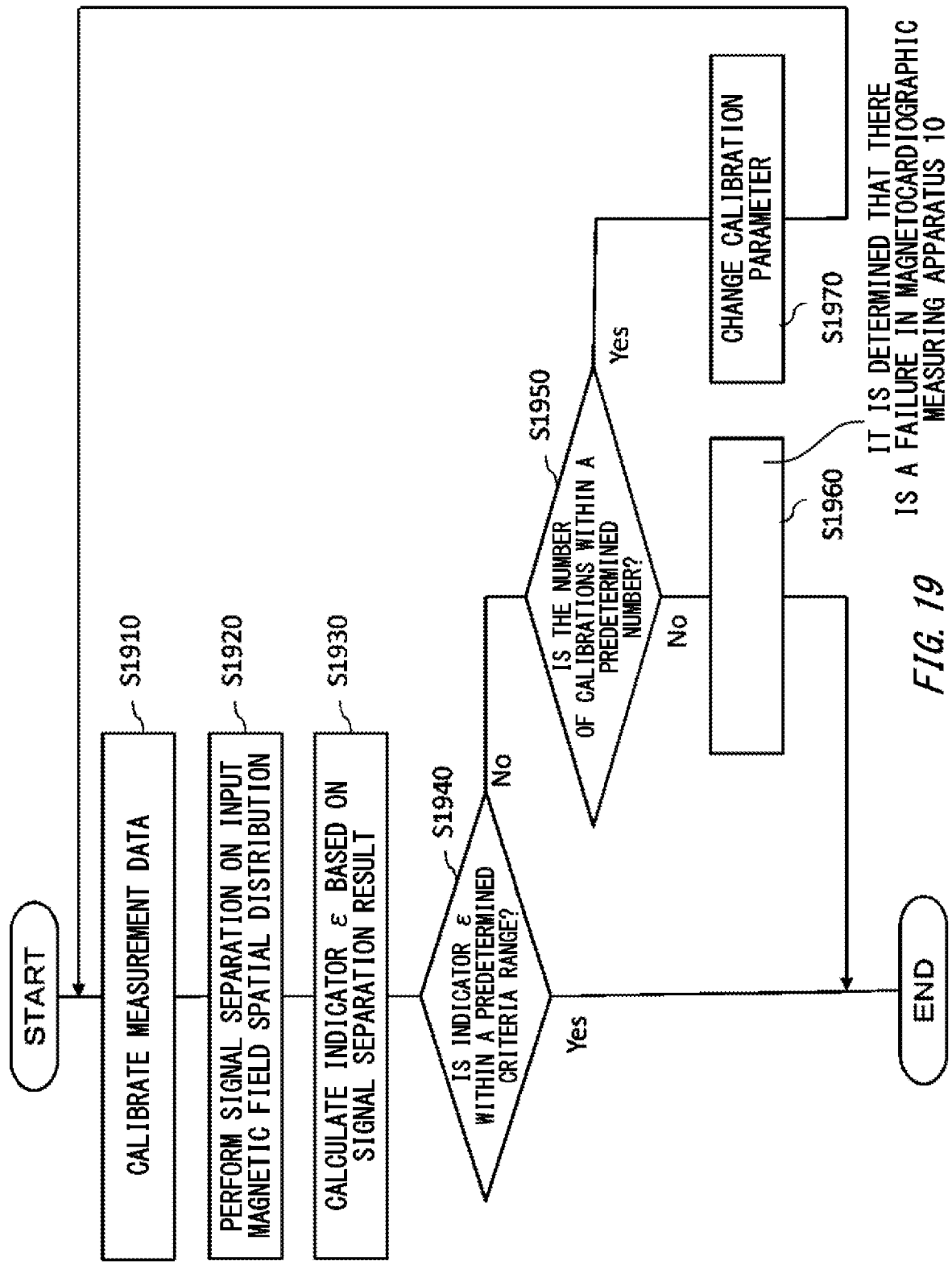
FIG. 19 illustrates a flow of the magnetocardiographic measuring apparatus 10 according to the present embodiment calculating an indicator ε and performing control based on the indicator ε.

FIG. 19 illustrates a flow of the magnetocardiographic measuring apparatus 10 according to the present embodiment calculating an indicator ε and performing control based on the indicator ε. In step 1910, the calibration calculation section 1730 calibrates the measurement data V and generates the magnetic field measurement data B based on Expression 5 described above. Then, the calibration calculation section 1730 supplies the magnetic field measurement data B to the signal space separation section 1760 via the data output section 1740.

In step 1920, the signal space separation section 1760 signal-separates the input magnetic field spatial distribution indicated by the magnetic field measurement data B, according to the flow in FIG. 18. Then, the signal space separation section 1760 supplies the signal separation result to the indicator calculation section 1770. In this case, the signal space separation section 1760 may supply, for example, the sensor output vector Φ, the basis vector matrix S, and the column vector ^X to the indicator calculation section 1770 as the signal separation result.

In step 1930, the indicator calculation section 1770 calculates the indicator e, which indicates the calibration accuracy in the measurement data computing section 1721, for example, the calibration calculation section 1730, based on the signal separation result by the signal space separation section 1760. For example, the indicator calculation section 1770 may calculate the indicator ε by subtracting the inner product of the basis vector matrix S and the column vector ^X from the sensor output vector Φ, as shown in the following expression. In other words, the indicator calculation section 1770 calculates the error when mapping the sensor output vector Φ output by each magnetic sensor cell 220 at certain timing to the subspace stretched by the basis vector matrix S=[Sin, Sout] using the least-squares method, for each vector component, and sets it as the indicator ε. Then, the indicator calculation section 1770 supplies the calculated indicator ε to the indicator output section 1780.

$$\varepsilon = \phi - S \cdot \hat{X} \quad \text{[Expression 14]}$$

Next, the indicator output section 1780 displays the indicator ε on the display section. Then, the indicator output section 1780 supplies the indicator ε to the failure determination section 1790. In this case, the indicator output section 1780 may further supply the indicator ε to another apparatus via the network.

In step 1940, the failure determination section 1790 determines whether the indicator ε is within a predetermined criteria range or not. The failure determination section 1790 determines, for example, whether the square of the indicator is less than the square of the predetermined threshold value E_Th, as shown in the following expression. That is, the failure determination section 1790 determines whether the vector magnitude of the indicator ε is less than the predetermined threshold value E_th.

$$\varepsilon^2 = |\phi - S \cdot \hat{X}|^2 < E\_Th^2 \quad \text{[Expression 15]}$$

Herein, the indicator ε consists of a component of the vector corresponding to the number of sensor sections 300 included in the plurality of magnetic sensor cells 220 that the magnetic sensor array 210 has. The failure determination section 1790, for example, may calculate the indicator for each of the plurality of components, and determine whether the average is within a predetermined criteria range. Alternatively, the failure determination section 1790 may determine whether the indicator of the component with the largest magnitude, the indicator of the component with the smallest magnitude, and any of the median value of the plurality of components of the calculated indicators for each of the plurality of components are all within the predetermined criteria range.

Then, when the failure determination section 1790 determines that the indicator ε is within the predetermined criteria range, it determines that the indicator has been highly accurately calibrated in the calibration calculation section 1730 and ends the process. In other words, the failure determination section 1790 determines that the measurement result of the magnetocardiographic measuring apparatus 10 are highly reliable since it has been accurately calibrated in the calibration calculation section 1730, and does not require further processing.

On the other hand, if it is determined in step 1940 that the indicator ε is not within the predetermined criteria range, the failure determination section 1790 determines in step 1950 whether the number of calibrations in the calibration calculation section 1730 is within the predetermined number.

Then, if it has been determined that the number of calibrations is not within the predetermined number, in step 1960, the failure determination section 1960 determines that a failure has occurred in the magnetocardiographic measuring apparatus 10 and ends the process. In this case, the failure determination section 1960 may display on the display section or inform the user by sound that a failure has occurred in the magnetocardiographic measuring apparatus 10. Also, the failure determination section 1960 may estimate the failure part of the magnetocardiographic measuring apparatus 10 from the indicators for each component of the vector calculated in step 1940 and output them. In this case, the failure determination section 1960 may output information that identifies the magnetic sensor cell 220 or sensor section 300 corresponding to the indicator that is determined to be not within the predetermined criteria range. Also, the failure determination section 1960 may, for example, output an indicator map that maps the indicators for each vector component to the corresponding magnetic sensor cell 220 or sensor section 300.

On the other hand, in step 1950, when the number of calibrations is determined to be within the predetermined number, the failure determination section instructs the calibration calculation section 1730 to recalibrate the measurement data. Then, in step 1970, the calibration calculation section 1730 changes the calibration parameters, returns the process to step 1910, recalibrates by using the changed calibration parameters, and continues the process. In this case, the calibration calculation section 1730 may change the calibration parameters by, for example, measuring the environment magnetic field again and readjusting the main axis sensitivity, cross-axis sensitivities, and offset of the sensor section 300.

Note that the flow in FIG. 19 may be performed when the subject is at the measurement position of the magnetocardiographic measuring apparatus 10, or it may be performed in advance before the subject comes to the measurement position of magnetocardiographic measuring apparatus 10. In this case, the failure determination section may set the threshold value E_Th used for failure determination to a different value in a case where the subject is present and in a case where the subject is not present.

In this way, the magnetocardiographic measuring apparatus 10 according to the present embodiment calculates an indicator ε indicating the calibration accuracy in the measurement data computing section 1721, for example, the calibration calculation section 1730, and performs control based on the indicator ε. As a result, with the magnetocardiographic measuring apparatus 10 according to the present embodiment, it is possible to understand whether or not it has been accurately calibrated in the calibration calculation section 1730. Also, with the magnetocardiographic measuring apparatus 10 according to the present embodiment, the user can be informed of the reliability of the measurement results of the magnetocardiographic measuring apparatus 10 by displaying the indicator ε. Also, with the magnetocardiographic measuring apparatus 10 according to the present embodiment, the failure of the magnetocardiographic measuring apparatus 10 can be determined based on the indicator ε and the failure part can be estimated. Also, with the magnetocardiographic measuring apparatus according to the present embodiment, the measurement data computing section 1721, for example, the calibration calculation section 1730, recalibrates the measurement data V based on the indicator ε calculated by the indicator calculation section 1770, so that the cardiac magnetic field can be measured in a precisely calibrated state.

Figure 20:
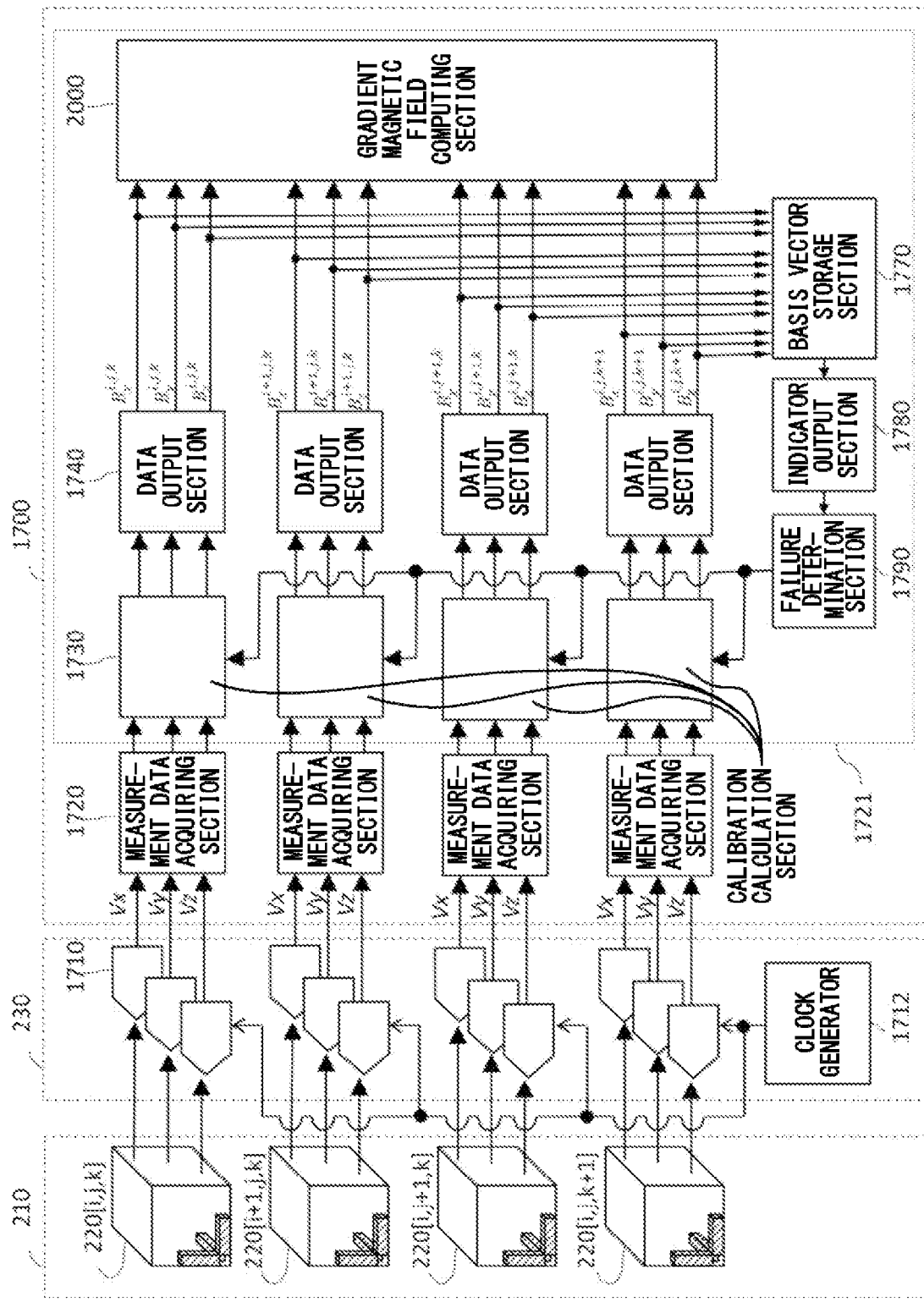
FIG. 20 illustrates a configuration of a magnetic sensor array 210, a sensor data gathering section 230 and a sensor data processing section 1700 according to a variation of the present embodiment.

FIG. 20 illustrates a configuration of a magnetic sensor array 210, a sensor data gathering section 230 and a sensor data processing section 1700 according to a variation of the present embodiment. In FIG. 20, members having the same function and configuration as in FIG. 17 are given the same reference numerals, and the following describes only differing points. In the present drawing, the measurement data computing section 1721 has a gradient magnetic field computing section 2000, instead of a basis vector storage section 1750 and a signal space separation section 1760. Further, the indicator calculation section 1770 is connected to the data output section 1740, instead of the signal space separation section 1760.

The gradient magnetic field computing section 2000 calculates the gradient magnetic field using the magnetic field measurement data B supplied from the data output section 1740. In the present variation, the gradient magnetic field computing section 2000 calculates the gradient magnetic field in all the three-dimensional directions relative to all the magnetic fields in three axial directions. In this way, a more detailed gradient magnetic field distribution can be obtained. Alternatively, the gradient magnetic field computing section 2000 may calculate only the gradient magnetic field relative to a part of the magnetic fields in the three axial directions. Also, the gradient magnetic field computing section 2000 may calculate only the gradient magnetic field for part of the directions of the three-dimensional directions. This allows only the necessary gradient magnetic field components to be calculated, and reduces the load of the operation process in the gradient magnetic field computing section 2000.

Also, in the present variation, the three axial directions of the detected magnetic field are the same direction as those of the three-dimensional directions in which the magnetic sensor cells 220 are arranged. In this way, each component of the gradient magnetic field in the distribution drawing of the gradient magnetic field as shown below becomes easier to understand. Alternatively, the three axial directions of the detected magnetic field may be different from the three-dimensional directions in which the magnetic sensor cells 220 are arranged. When these directions are different from each other, no restriction on the arrangement of the sensor sections 300 in the magnetic sensor cells 220 and the arrangement direction of the magnetic sensor cells 220 can increase the flexibility of the design of the magnetic sensor array 210.

The gradient magnetic field computing section 2000 calculates the gradient magnetic field by calculating the difference in the magnetic field between adjacent magnetic sensor cells 220 using the magnetic field measurement data B measured between the adjacent magnetic sensor cells 220 of the plurality of magnetic sensor cells 220, that is, by calculating the difference in the magnetic field measurement data B. The gradient magnetic field computing section 2000 may calculate the gradient magnetic field of the second or higher order using the magnetic field measurement data B measured between the plurality of adjacent magnetic sensor cells 220.

Figure 21:
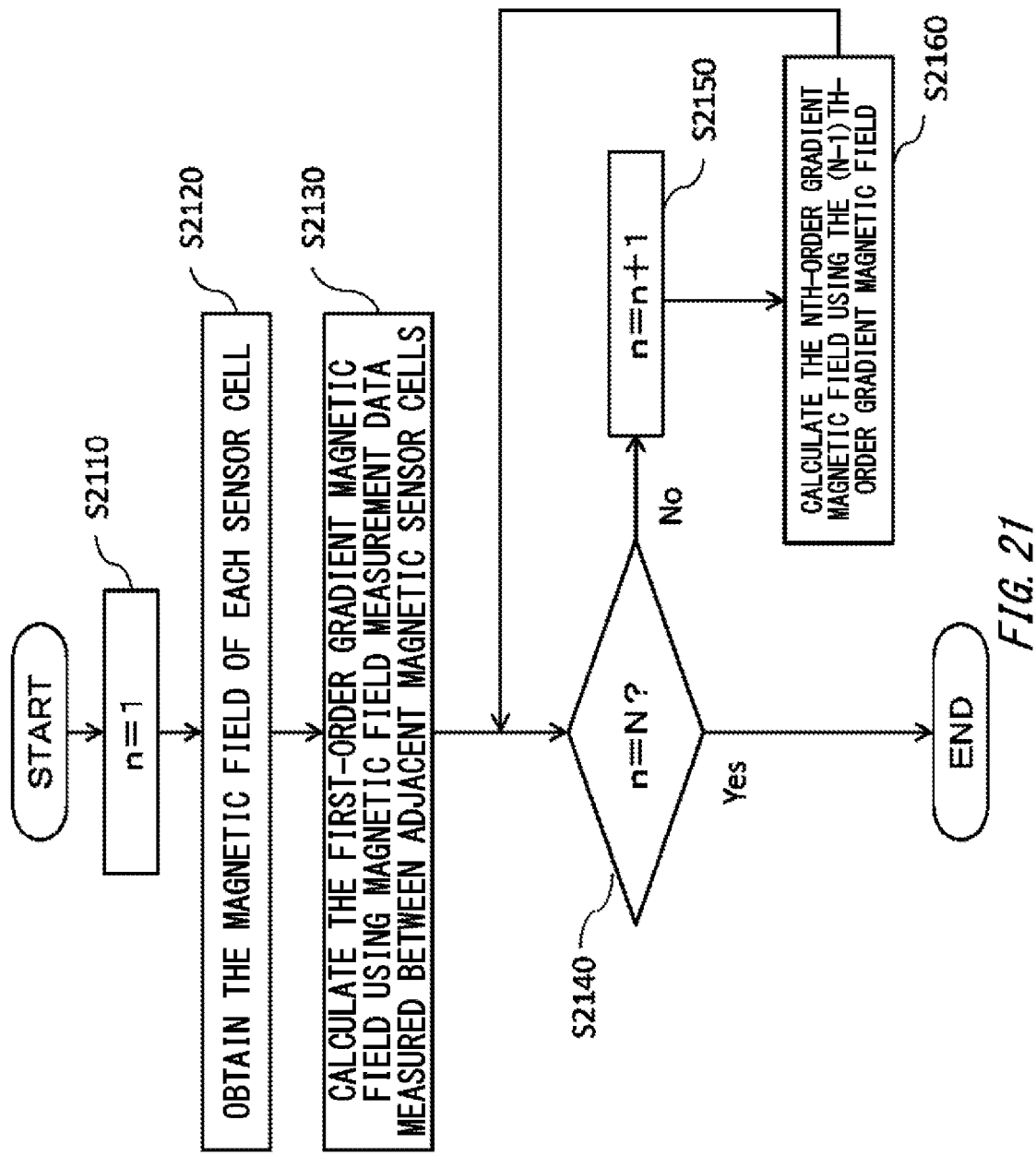
FIG. 21 illustrates a flow of the magnetocardiographic measuring apparatus 10 according to the present variation calculating an Nth-order gradient magnetic field.

FIG. 21 illustrates a flow of the magnetocardiographic measuring apparatus 10 according to the present variation calculating an Nth-order gradient magnetic field. In step 2110, the gradient magnetic field computing section 2000 substitutes 1 for n. In step 2120, the gradient magnetic field computing section 2000 obtains the magnetic field measurement data B measured by the magnetic sensor cell 220 at each position. Herein, the magnetic field measurement data measured by the magnetic sensor cell 220 at position [i, j, k] is denoted by the following expression (Expression 16).

$$B^{i,j,k} = (B_x^{i,j,k}, B_y^{i,j,k}, B_z^{i,j,k})^T \qquad \text{[Expression 16]}$$

In step 2130, the gradient magnetic field computing section 2000 calculates the first-order gradient magnetic field by calculating the first-order difference of the magnetic field using the magnetic field measurement data B between each adjacent magnetic sensor cell 220 included in the magnetic sensor array 210. The gradient magnetic field computing section 2000 calculates the first-order gradient magnetic field about the X-axis direction using the magnetic field measurement data measured between the magnetic sensor cell 220 [i+1, j, k] and the magnetic sensor cell 220 [i, j, k] using the following expression.

$$\frac{B^{i+1,j,k} - B^{i,j,k}}{\Delta x} = \left( \frac{\Delta B_x^{i,j,k}}{\Delta x}, \frac{\Delta B_y^{i,j,k}}{\Delta x}, \frac{\Delta B_z^{i,j,k}}{\Delta x} \right)^T \qquad \text{[Expression 17]}$$

In other words, the gradient magnetic field computing section 2000 subtracts the X-axis magnetic field measurement data $B_x^{i,j,k}$ in the magnetic sensor cell 220 [i,j,k] from the X-axis magnetic field measurement data $Bx^{i+1,j,k}$ in the magnetic sensor cell 220 [i+1,j,k] to calculate the X-axis component difference of the magnetic field measurement data between the magnetic sensor cell 220 [i+1,j,k] and the magnetic sensor cell 220 [i,j,k]. The difference in the X-axis component of the magnetic field measurement data between the magnetic sensor cell 220 [i+1, j, k] and the magnetic sensor cell 220 [i, j, k] is calculated and divided by the distance Δx between the magnetic sensor cell 220 [i+1, j, k] and the magnetic sensor cell 220 [i, j, k], thereby the first-order gradient magnetic field for the X-axis component about the X-axis direction of the magnetic field measurement data at position [i, j, k] is calculated.

Similarly, the gradient magnetic field computing section 2000 subtracts the Y-axis magnetic field measurement data $B_y^{i,j,k}$ in the magnetic sensor cell 220 [i,j,k] from the Y-axis magnetic field measurement data $By^{i+1,j,k}$ in the magnetic sensor cell 220 [i+1,j,k], and calculates the Y-axis component difference of the magnetic field measurement data between the magnetic sensor cell 220 [i+1,j,k] and the magnetic sensor cell 220 [i,j,k]. The difference in the Y-axis component of the magnetic field measurement data between the magnetic sensor cell 220 [i+1, j, k] and the magnetic sensor cell 220 [i, j, k] is calculated and divided by the distance Δx between the magnetic sensor cell 220 [i+1, j, k] and the magnetic sensor cell 220 [i, j, k], thereby the first-order gradient magnetic field for the Y-axis component about the X-axis direction of the magnetic field measurement data at position [i, j, k] is calculated.

Similarly, the gradient magnetic field computing section 2000 subtracts the Z-axis magnetic field measurement data $B_z^{i,j,k}$ in the magnetic sensor cell 220 [i,j,k] from the Z-axis magnetic field measurement data $Bz^{i+1,j,k}$ in the magnetic sensor cell 220 [i+1,j,k], and calculates the Z-axis component difference of the magnetic field measurement data between the magnetic sensor cell 220 [i+1,j,k] and the magnetic sensor cell 220 [i,j,k]. The difference in the Z-axis component of the magnetic field measurement data between the magnetic sensor cell 220 [i+1, j, k] and the magnetic sensor cell 220 [i, j, k] is calculated and divided by the distance Δx between the magnetic sensor cell 220 [i+1, j, k] and the magnetic sensor cell 220 [i, j, k], thereby the first-order gradient magnetic field for the Z-axis component about the X-axis direction of the magnetic field measurement data at position [i, j, k] is calculated.

Further, the gradient magnetic field computing section 2000 calculates the first-order gradient magnetic field for the Y-axis direction similarly to the first-order gradient magnetic field for the X-axis direction using the magnetic field measurement data measured between the magnetic sensor cell 220 [i, j+1, k] and the magnetic sensor cell 220 [i, j, k] using the following expression.

$$\frac{B^{i,j+1,k} - B^{i,j,k}}{\Delta y} = \left( \frac{\Delta B_x^{i,j,k}}{\Delta y}, \frac{\Delta B_y^{i,j,k}}{\Delta y}, \frac{\Delta B_z^{i,j,k}}{\Delta y} \right)^T \quad \text{[Expression 18]}$$

Also, the gradient magnetic field computing section 2000 calculates the first-order gradient magnetic field for the Z-axis direction similarly to the first-order gradient magnetic field for the X-axis direction using the magnetic field measurement data measured between the magnetic sensor cell 220 [i, j, k+1] and the magnetic sensor cell 220 [i, j, k] using the following expression.

$$\frac{B^{i,j,k+1} - B^{i,j,k}}{\Delta z} = \left( \frac{\Delta B_x^{i,j,k}}{\Delta z}, \frac{\Delta B_y^{i,j,k}}{\Delta z}, \frac{\Delta B_z^{i,j,k}}{\Delta z} \right)^T \quad \text{[Expression 19]}$$

The gradient magnetic field computing section 2000 can obtain the following first-order gradient magnetic fields in the three-dimensional direction for the 3-axis magnetic field measurement data by the operation of Expression 17 to Expression 19. Note that the gradient magnetic field computing section 2000 may calculate the first-order gradient magnetic field using the distance Δx=Δy=Δz between each magnetic sensor cell 220 as one unit. In this case, the gradient magnetic field computing section 2000 can regard the difference of the magnetic field measurement data as the first-order gradient magnetic field.

$$\begin{bmatrix} \frac{\Delta B_x^{i,j,k}}{\Delta x} & \frac{\Delta B_x^{i,j,k}}{\Delta y} & \frac{\Delta B_x^{i,j,k}}{\Delta z} \\ \frac{\Delta B_y^{i,j,k}}{\Delta x} & \frac{\Delta B_y^{i,j,k}}{\Delta y} & \frac{\Delta B_y^{i,j,k}}{\Delta z} \\ \frac{\Delta B_z^{i,j,k}}{\Delta x} & \frac{\Delta B_z^{i,j,k}}{\Delta y} & \frac{\Delta B_z^{i,j,k}}{\Delta z} \end{bmatrix} \quad \text{[Expression 20]}$$

In step 2140, the gradient magnetic field computing section 2000 determines whether n is equal to N. If n is equal to N, the gradient magnetic field computing section 2000 ends the process. In step 2140, if n is not equal to N, the gradient magnetic field computing section 2000 proceeds the process to step 2150 and increments n by 1. Then, the gradient magnetic field computing section 2000 proceeds the process to step 2160.

In step 2160, the gradient magnetic field computing section 2000 calculates the nth-order gradient magnetic field using the n−1st-order gradient magnetic field of the magnetic field. As one example, the gradient magnetic field computing section 2000 has already calculated the first-order gradient magnetic field at the position [i+1, j, k] by the following expression using the magnetic field measurement data measured between the magnetic sensor cell 220 [i+2, j, k] and the magnetic sensor cell 220 [i+1, j, k] as the first-order gradient magnetic field in the X-axis direction in addition to Expression 17 in the step 2130 before the calculation of the second-order gradient magnetic field.

$$\frac{B^{i+2,j,k} - B^{i+1,j,k}}{\Delta x} = \left( \frac{\Delta B_x^{i+1,j,k}}{\Delta x}, \frac{\Delta B_y^{i+1,j,k}}{\Delta x}, \frac{\Delta B_z^{i+1,j,k}}{\Delta x} \right)^T \quad \text{[Expression 21]}$$

Therefore, in step 2160 when calculating the second-order gradient magnetic field, the gradient magnetic field computing section 2000 calculates the second-order gradient magnetic field about the X-axis direction by the following expression using the first-order gradient magnetic field calculated by Expression 17 and Expression 21.

$$\frac{\frac{B^{i+2,j,k} - B^{i+1,j,k}}{\Delta x} - \frac{B^{i+1,j,k} - B^{i,j,k}}{\Delta x}}{\Delta x} = \left( \frac{\Delta^2 B_x^{i,j,k}}{\Delta x^2}, \frac{\Delta^2 B_y^{i,j,k}}{\Delta x^2}, \frac{\Delta^2 B_z^{i,j,k}}{\Delta x^2} \right)^T \quad \text{[Expression 22]}$$

In other words, the gradient magnetic field computing section 2000 calculates the second-order gradient magnetic field in the X-axis direction by dividing the value obtained by subtracting the first-order gradient magnetic field in the X-axis direction at position [i, j, k] from the first-order gradient magnetic field in the X-axis direction at position [i+1, j, k] by the distance ΔX between adjacent magnetic sensor cells 220 in the X-axis direction.

The gradient magnetic field computing section 2000 can calculate the second-order gradient magnetic field for the Y-axis direction and Z-axis direction by the same operation as for the X-axis direction. Next, the gradient magnetic field computing section 2000 returns the process to step 2140, and repeats the below process. This allows the gradient magnetic field computing section 2000 to obtain the nth-order gradient magnetic field in the three-dimensional directions for the 3-axis magnetic field measurement data using the magnetic field measurement data measured between adjacent magnetic sensor cells 220.

Herein, when N=1, the gradient magnetic field computing section 2000 can express the first-order gradient magnetic field given by the Expression 20 obtained in step 2130 as follows, assuming that $\Delta x = \Delta y = \Delta z$ is sufficiently small.

$$\begin{bmatrix} \frac{\partial B_x^{i,j,k}}{\partial x} & \frac{\partial B_x^{i,j,k}}{\partial y} & \frac{\partial B_x^{i,j,k}}{\partial z} \\ \frac{\partial B_y^{i,j,k}}{\partial x} & \frac{\partial B_y^{i,j,k}}{\partial y} & \frac{\partial B_y^{i,j,k}}{\partial z} \\ \frac{\partial B_z^{i,j,k}}{\partial x} & \frac{\partial B_z^{i,j,k}}{\partial y} & \frac{\partial B_z^{i,j,k}}{\partial z} \end{bmatrix}$$ [Expression 23]

When N=2, the gradient magnetic field computing section 2000 obtains the first-order gradient magnetic field and the following second-order gradient magnetic field according to the flow in the present drawing.

$$\begin{bmatrix} \frac{\partial^2 B_x^{i,j,k}}{\partial x^2} & \frac{\partial^2 B_x^{i,j,k}}{\partial y^2} & \frac{\partial^2 B_x^{i,j,k}}{\partial z^2} \\ \frac{\partial^2 B_y^{i,j,k}}{\partial x^2} & \frac{\partial^2 B_y^{i,j,k}}{\partial y^2} & \frac{\partial^2 B_y^{i,j,k}}{\partial z^2} \\ \frac{\partial^2 B_z^{i,j,k}}{\partial x^2} & \frac{\partial^2 B_z^{i,j,k}}{\partial y^2} & \frac{\partial^2 B_z^{i,j,k}}{\partial z^2} \end{bmatrix}$$ [Expression 24]

If N is greater than 2, the gradient magnetic field computing section 2000 obtains the first-order and the second-order gradient magnetic fields and the following nth-order gradient magnetic fields according to the flow of the present drawing.

$$\begin{bmatrix} \frac{\partial^n B_x^{i,j,k}}{\partial x^n} & \frac{\partial^n B_x^{i,j,k}}{\partial y^n} & \frac{\partial^n B_x^{i,j,k}}{\partial z^n} \\ \frac{\partial^n B_y^{i,j,k}}{\partial x^n} & \frac{\partial^n B_y^{i,j,k}}{\partial y^n} & \frac{\partial^n B_y^{i,j,k}}{\partial z^n} \\ \frac{\partial^n B_z^{i,j,k}}{\partial x^n} & \frac{\partial^n B_z^{i,j,k}}{\partial y^n} & \frac{\partial^n B_z^{i,j,k}}{\partial z^n} \end{bmatrix}$$ [Expression 25]

In this way, according to the magnetocardiographic measuring apparatus 10 of the present variation, the gradient magnetic field in the three-dimensional directions can be obtained for the 3-axis magnetic field measurement data without omissions, as shown in Expression 23, Expression 24 and Expression 25. Also, according to the magnetocardiographic measuring apparatus 10 of the present variation, since the operation is based on the magnetic field between adjacent magnetic sensor cells 220, not only the gradient magnetic field of the second or higher order in the X-axis direction, Y-axis direction, and Z-axis direction only, but also the gradient magnetic field component corresponding to the form of partial differentiation in different axial directions, such as $\partial^2 B/\partial x\, \partial y$, $\partial^2 B/\partial y\, \partial z$, and $\partial^2 B/\partial z\, \partial x$, can be obtained.

Figure 22:
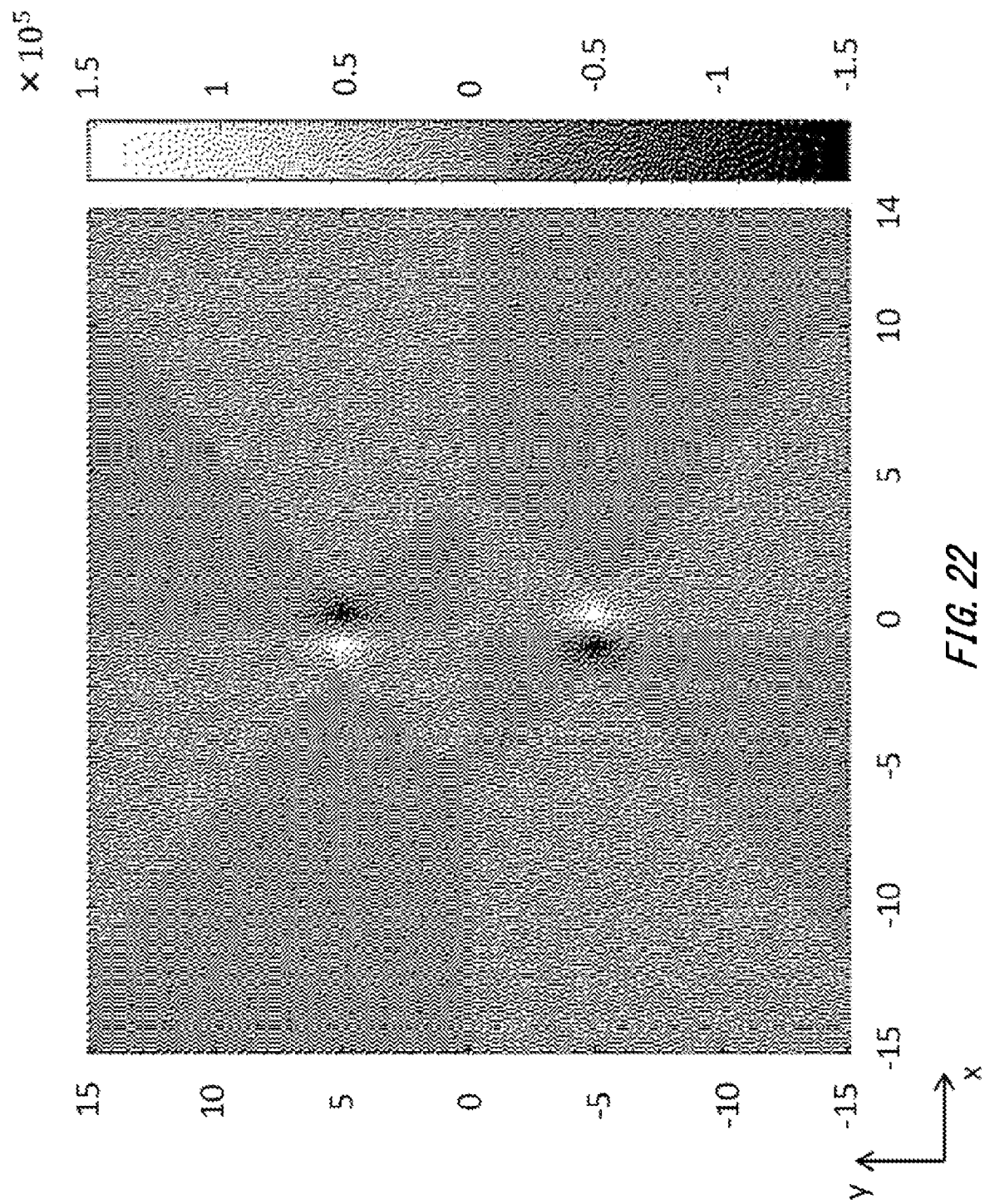
FIG. 22 illustrates one example of a first-order gradient magnetic field distribution obtained by the magnetocardiographic measuring apparatus 10 according to the present variation.
Figure 23:
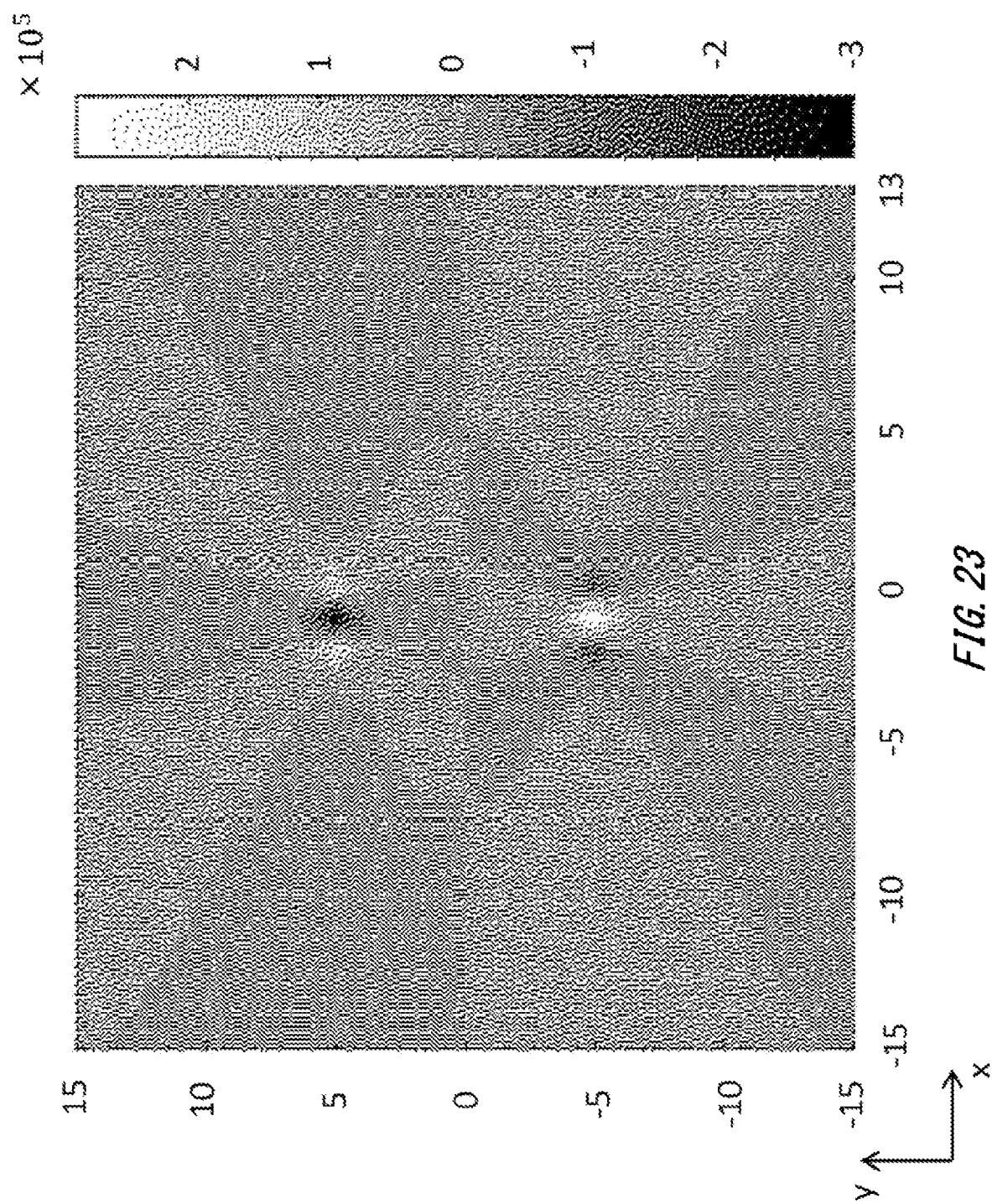
FIG. 23 illustrates one example of a second-order gradient magnetic field distribution obtained by the magnetocardiographic measuring apparatus 10 according to the present variation.

FIG. 22 illustrates one example of a first-order gradient magnetic field distribution obtained by the magnetocardiographic measuring apparatus 10 according to the present variation. FIG. 23 illustrates one example of a second-order gradient magnetic field distribution obtained by the magnetocardiographic measuring apparatus 10 according to the present variation. These drawings show that a magnet with X=5 mm, Y=0.5 mm, Z=0.5 mm is placed at the point (X, Y)=(0, −5 cm) so that the N-pole faces the positive direction of the X-axis, and a magnet with X=5 mm, Y=0.5 mm, Z=0.5 mm is placed at the point (X, Y)=(0, 5 cm) so that the N-pole faces the negative direction of the X-axis. The gradient magnetic field distribution is shown when the magnet is placed so that its N-pole faces the negative direction of the X-axis, and the gradient magnetic field is measured by the magnetocardiographic measuring apparatus 10 at a height of Z=1 cm from the surface where the magnet is placed, with grid points at 1 cm intervals on a 30 cm×30 cm plane. In these drawings, the dot density at each coordinate indicates the magnitude of the gradient magnetic field in arbitrary units, with a smaller dot density indicating a larger gradient magnetic field. FIG. 22 illustrates the $\partial B_x/\partial x$ component of the first-order gradient magnetic field distribution obtained by this condition, and FIG. 23 illustrates the $\partial^2 B_x/\partial x^2$ component of the second-order gradient magnetic field distribution obtained by this condition.

As shown in FIG. 22 and FIG. 23, according to the magnetocardiographic measuring apparatus 10 of the present variation, the gradient magnetic field distribution that visualizes the calculated gradient magnetic field can be obtained. Note that in the present drawing, only the $\partial B_x/\partial x$ component for the first-order gradient magnetic field distribution and the $\partial^2 B_x/\partial x^2$ component for the second-order gradient magnetic field distribution are shown as one example, but the magnetocardiographic measuring apparatus 10 can obtain the gradient magnetic field distribution in the same way for other gradient components and gradient magnetic fields of the third-order or higher.

Figure 24:
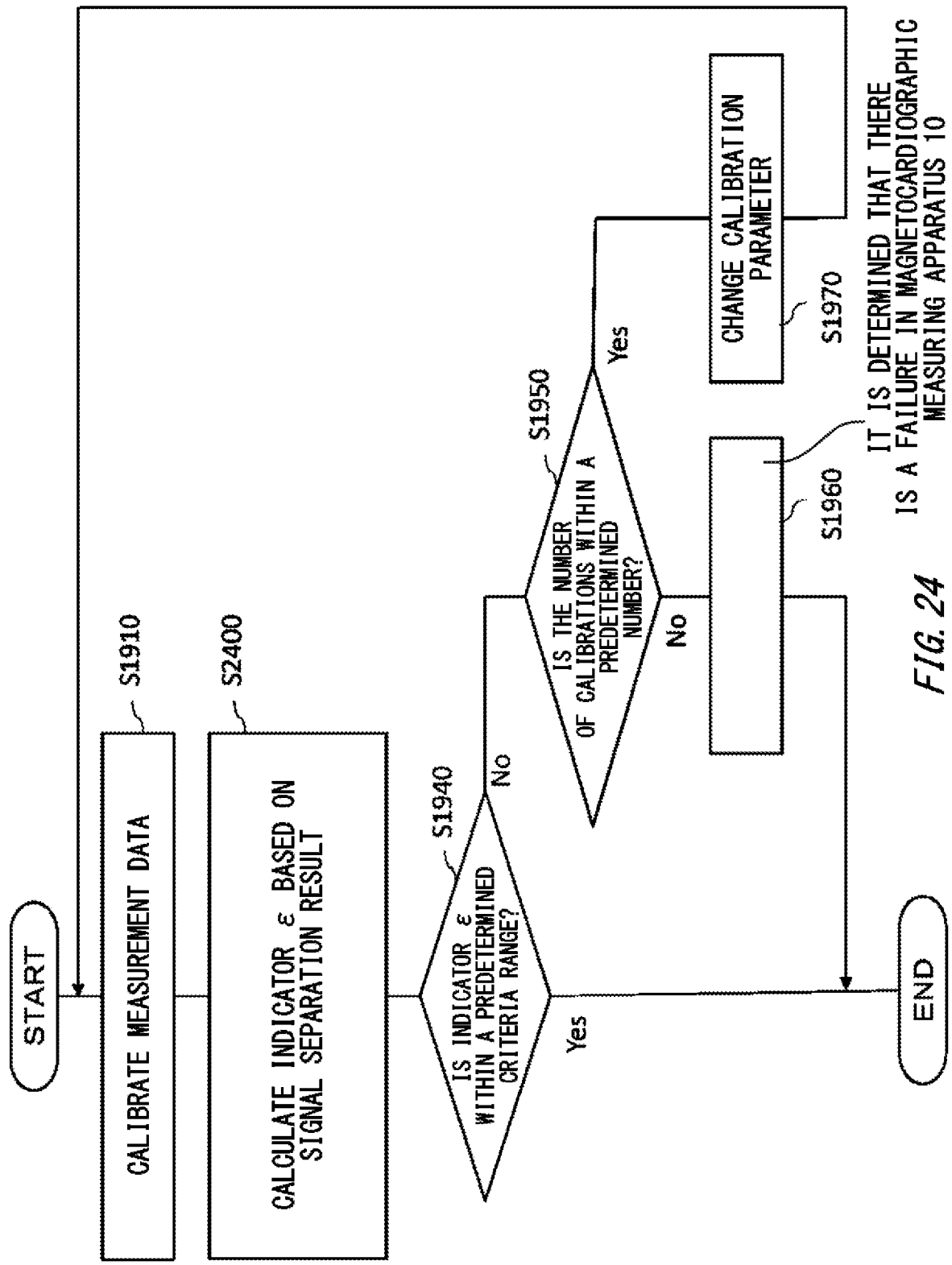
FIG. 24 illustrates a flow of the magnetocardiographic measuring apparatus 10 according to the present variation calculating the indicator ε and performing control based on the indicator ε.

FIG. 24 illustrates a flow of the magnetocardiographic measuring apparatus 10 according to the present variation calculating the indicator ε and performing control based on the indicator ε. In FIG. 24, members having the same function and configuration as in FIG. 21 are given the same reference numerals for the same step, and the following describes only differing points. In the present drawing, there is step 2400 instead of step 1920 and step 1930.

In step 2400, the indicator calculation section 1770 calculates the indicator e based on the statistics of the magnetic field measurement data in the plurality of magnetic sensor cells 220 generated from the measurement data, for example, the statistics of the magnetic field measurement data in the plurality of magnetic sensor cells 220 generated by the calibration calculation section 1730 calibrating the measurement data. For example, the indicator calculation section 1770 calculates the average value of the magnetic field measurement data in the plurality of magnetic sensor cells 220 using the following expression. In other words, the indicator calculation section 1770 calculates the average value of the magnetic field measurement data by dividing the sum of the respective magnetic field measurement data in the plurality of magnetic sensor cells 220 by the number of magnetic sensor cells 220.

$$\begin{pmatrix} \overline{Bx} \\ \overline{By} \\ \overline{Bz} \end{pmatrix} = \frac{1}{I \times J \times K} \sum_{[i,j,k]} \begin{pmatrix} B_x^{i,j,k} \\ B_y^{i,j,k} \\ B_z^{i,j,k} \end{pmatrix}$$ [Expression 26]

Then, the indicator calculation section 1770 calculates the indicator ε in each of the plurality of magnetic sensor cells 220 using the following expression. That is, the indicator calculation section 1770 calculates the indicator ε in each of the plurality of magnetic sensor cells 220 by subtracting the average value of the magnetic field measurement data calculated by Expression 26 from the magnetic field measurement data in each of the magnetic sensor cells 220.

$$\varepsilon = \begin{pmatrix} B_x^{i,j,k} \\ B_y^{i,j,k} \\ B_z^{i,j,k} \end{pmatrix} - \begin{pmatrix} \overline{Bx} \\ \overline{By} \\ \overline{Bz} \end{pmatrix}$$ [Expression 27]

Note that the above-mentioned description describes the case where the indicator ε is calculated based on the difference from the average value of the magnetic field measurement data, but it is not limited to this case. The indicator calculation section 1770 may, for example, calculate the indicator ε in each of the plurality of magnetic sensor cells 220 by subtracting the median value instead of the average value from the magnetic field measurement data in each of the magnetic sensor cells 220. Generally, an average value is easily affected by outliers. Therefore, the indicator calculation section 1770 may calculate the indicator ε with reduced influence of outliers by using the median value instead of the average value. In this way, the indicator calculation section 1770 may calculate the indicator ε based on various statistics of the magnetic field measurement data in the plurality of magnetic sensor cells 220.

In this way, the magnetocardiographic measuring apparatus 10 according to the present variation calculates the indicator ε based on the magnetic field measurement data, so that the indicator ε can be calculated without signal separation processing that requires complex operations such as the flow shown in FIG. 18.

Figure 25:
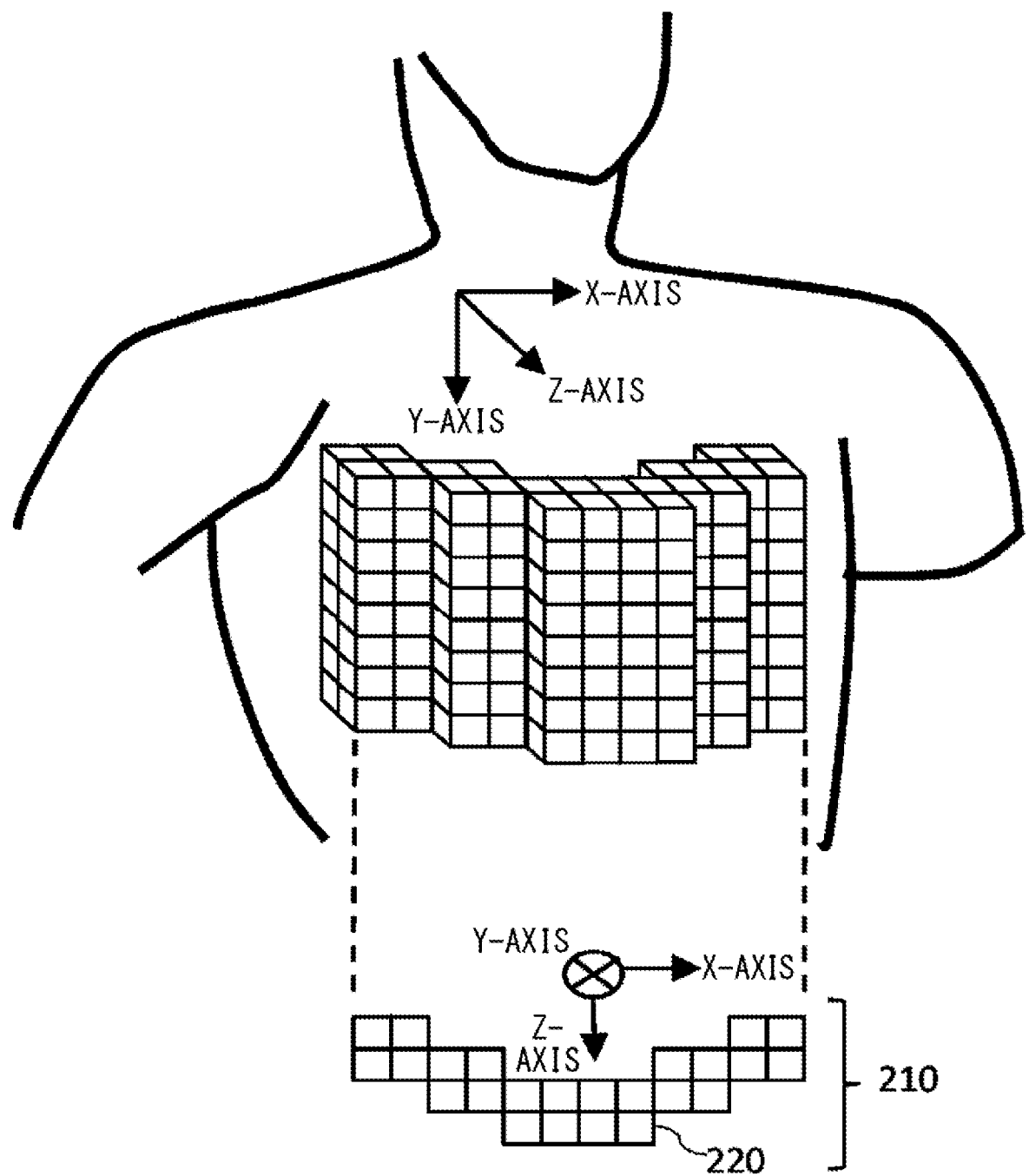
FIG. 25 illustrates an example of the magnetocardiographic measuring apparatus 10 according to a variation of the present embodiment measuring the cardiac magnetic field using the magnetic sensor array 210 arranged in a curved surface shape.

FIG. 25 illustrates an example of the magnetocardiographic measuring apparatus 10 according to a variation of the present embodiment measuring the cardiac magnetic field using the magnetic sensor array 210 arranged in a curved surface shape. In the present variation, the magnetic sensor array 210 has a plurality of magnetic sensor cells 220 arranged in each of the X direction, the Y direction, and the Z direction to have a curved surface shape (for example, a total of 192 magnetic sensor cells 220 with 12 cells arranged in the X direction, 8 cells arranged in the Y direction, and 2 cells arranged in the Z direction). Each magnetic sensor cells 220 are arranged at respective grid points included in the curved surface shape in a three-dimensional lattice space. Note that herein, the grid points are points respectively provided at predetermined regular intervals or the like along the X direction, the Y direction, and the Z direction to form a lattice form. As one example, each magnetic sensor cell 220 is arranged along a curved surface protruding in a direction orthogonal to any one direction of the X direction, the Y direction, and the Z direction, as viewed from one direction. The present drawing illustrates an example where each magnetic sensor cell 220 is arranged along a curved surface protruding in a positive direction of the Z-axis as viewed from the Y direction. The magnetic sensor array 210 is wrapped along the curved surface around the chest of the subject. In other words, the magnetic sensor array 210 is arranged in the form of a curved surface with a curvature substantially the same as the curvature around the chest of the subject. Therefore, the magnetic sensor array 210 becomes a curved surface such that the center of the front surface of the subject protrudes in the positive direction of the Z-axis, and herein, such a curved surface is presented as a protruding curved surface. In this case, for example, the magnetic sensor array 210 may form a curved surface shape protruding in the positive direction of the Z-axis, with the respective magnetic sensor cells 220 arranged at the respective grid points in the three-dimensional lattice space while having the respective vertices of the respective magnetic sensor cells 220 arranged in the negative direction of the Z-axis as much as possible without exceeding a range of a predetermined curved surface protruding in the positive direction of the Z-axis.

Then, in the present variation, the magnetocardiographic measuring apparatus 10 measures the cardiac magnetic field by arranging the magnetic sensor array 210 so that the chest of the subject is located at the center side of the curved surface, that is, the heart, which is the to-be-measured magnetic field source, is located at the center side of the curved surface. As a result, the magnetocardiographic measuring apparatus 10 can separate the to-be-measured magnetic field from the disturbance magnetic field with high accuracy by performing signal space separation using the magnetic field measurement data B measured at a position close to the heart, which is the to-be-measured magnetic field source. For the same reason, the magnetocardiographic measuring apparatus 10 can obtain the gradient distribution of the magnetic field with high accuracy. Note that in this case, the magnetic sensor array 210 preferably has the curvature of the curved surface substantially the same as the curvature around the chest of the subject, so that the magnetic field can be measured at a position closer to the heart that is the to-be-measured magnetic field source.

Figure 26:
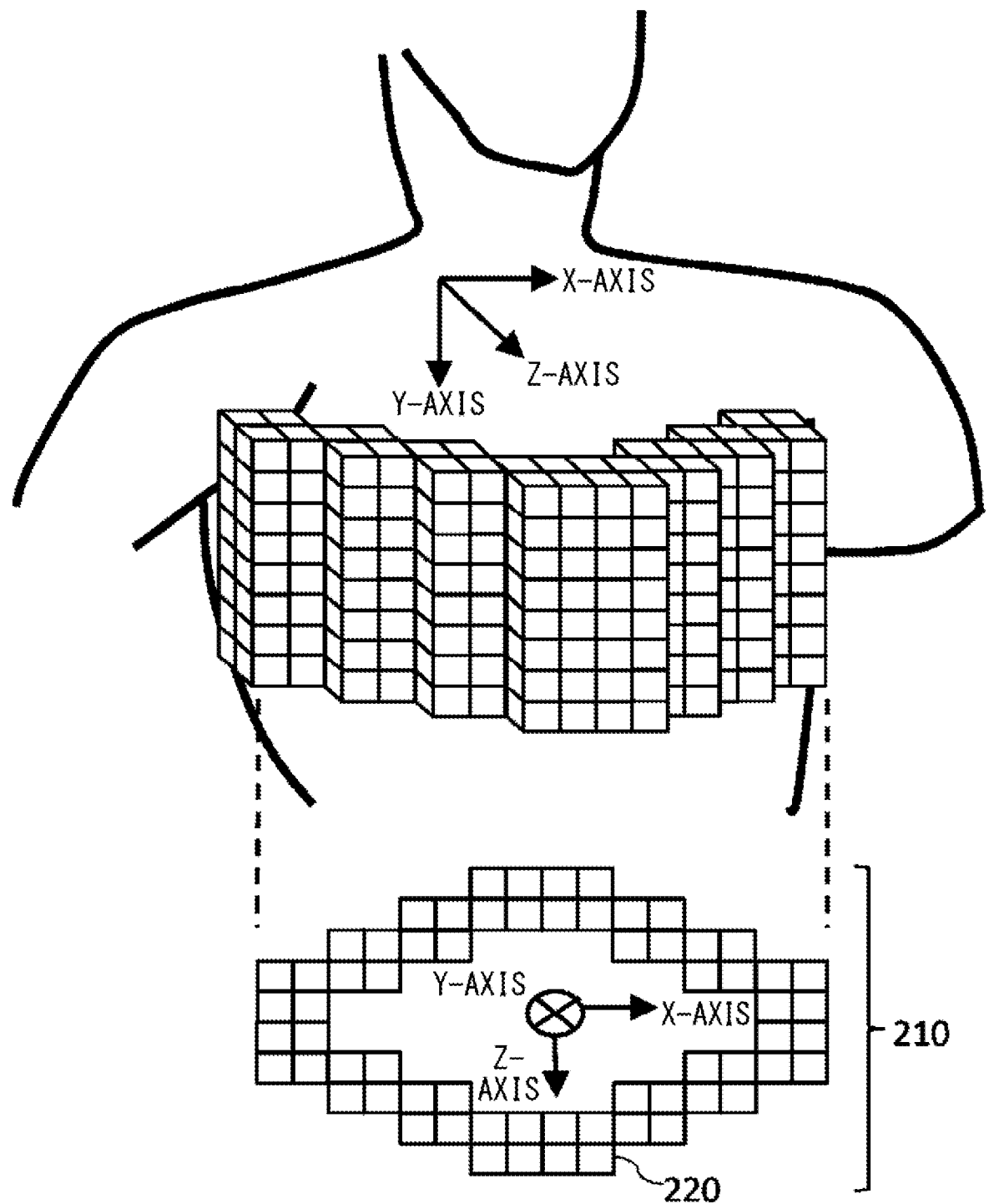
FIG. 26 illustrates an example of the magnetocardiographic measuring apparatus 10 according to a variation of the present embodiment measuring the cardiac magnetic field using the magnetic sensor array 210 arranged in a closed curved surface shape.

FIG. 26 illustrates an example of the magnetocardiographic measuring apparatus 10 according to a variation of the present embodiment measuring the cardiac magnetic field using the magnetic sensor array 210 arranged in a closed curved surface shape. In the present variation, the magnetic sensor array 210 has a plurality of plurality of magnetic sensor cells 220 arranged in each of the X direction, the Y direction, and the Z direction in a closed curved surface shape (for example, a total of 512 magnetic sensor cells 220 with 16 cells arranged in the X direction, 8 cells arranged in the Y direction, and 4 cells arranged in the Z direction). Respective magnetic sensor cells 220 are arranged at respective grid points included in the closed curved surface shape in a three-dimensional lattice space. Also in the present variation, the magnetic sensor array 210 includes the plurality of magnetic sensor cells 220 arranged along a curved surface protruding in a direction orthogonal to any one direction of the X direction, the Y direction, and the Z direction, as viewed from one direction, the same as in FIG. 25. In the present variation, the magnetic sensor array 210 further includes a plurality of magnetic sensor cells 220 arranged along a curved surface that is recessed in a direction orthogonal to the one direction. Then, the magnetic sensor array 210 forms the closed curved surface shape with the protruding curved surface shape and the recessed curved surface shape combined. As one example, the present drawing illustrates an example where the magnetic sensor array 210 includes a plurality of magnetic sensor cells 220 arranged along a curved surface protruding in the positive direction of the Z-axis as viewed from the Y direction and a plurality of magnetic sensor cells 220 arranged along a curved surface recessed in the positive direction of the Z-axis as viewed in the Y-direction, and forms the closed curved surface shape as a combination of the curved surface shapes respectively protruding and recessed in the positive direction in the Z-axis.

Then, in the present variation, the magnetocardiographic measuring apparatus 10 measures the magnetic field by arranging the magnetic sensor array 210 to enclose the chest of the subject with a closed curved surface, that is, to enclose the heart of the subject, which is the to-be-measured magnetic field source, with a closed curved surface. As a result, the magnetocardiographic measuring apparatus 10 can measure the cardiac magnetic field generated behind the subject in addition to the cardiac magnetic field generated in front of the subject by the electrical activity of the heart, and separate the to-be-measured magnetic field from the disturbance magnetic field with higher accuracy by performing the signal space separation using the magnetic field measurement data B measured in front and behind. For the same reason, the magnetocardiographic measuring apparatus 10 can obtain the gradient distribution of the magnetic field with high accuracy. Note that in the present variation, the same as FIG. 25, the magnetic sensor array 210 preferably has the curvature of the curved surface substantially the same as the curvature around the chest of the subject, so that the magnetic field can be measured at a position closer to the heart that is the to-be-measured magnetic field source.

The magnetocardiographic measuring apparatus 10 described so far can also estimate the signal source using the sensor output vector Φ output at each magnetic sensor cell 220 at certain timing. Generally, when an active current is generated in a volume conductor such as a living subject, the volume current that flows out of it or returns to it is widely distributed in the conductor. If the total current density at any position r1 of the heart is J(r1) and the magnetic permeability is μ, the magnetic flux density B(r) at the measurement position r can be expressed as shown in the following expression using Bio-Savart's law.

$$B(\vec{r}) = \frac{\mu}{4\pi} \int\int\int_{HEART} d\vec{r1} \frac{J(\vec{r1}) \times (\vec{r} - \vec{r1})}{|\vec{r} - \vec{r1}|^3}$$ [Expression 28]

Herein, based on Expression 28, the sensor output vector Φ can be expressed as the inner product of the coefficient matrix L and the current density vector J, as shown in the following expression.

$$\vec{\Phi} = L \cdot \vec{J}$$ [Expression 29]

Since the magnetocardiographic measuring apparatus 10 can acquire the value of the sensor output vector Φ and the position at which the value was measured, the current density vector J can be calculated by the inner product of the sensor output vector Φ and the inverse matrix of the coefficient matrix L, as shown in the following expression. In this way, with the magnetocardiographic measuring apparatus 10 according to the present embodiment, the current density vector J is calculated based on the sensor output vector Φ, thereby it is possible to estimate the signal source that has generated the magnetic field from the measured magnetic field, that is, the current generated by the electrical activity of the heart.

$$\vec{J} = L^{-1} \cdot \vec{\Phi}$$ [Expression 30]

Figure 27:
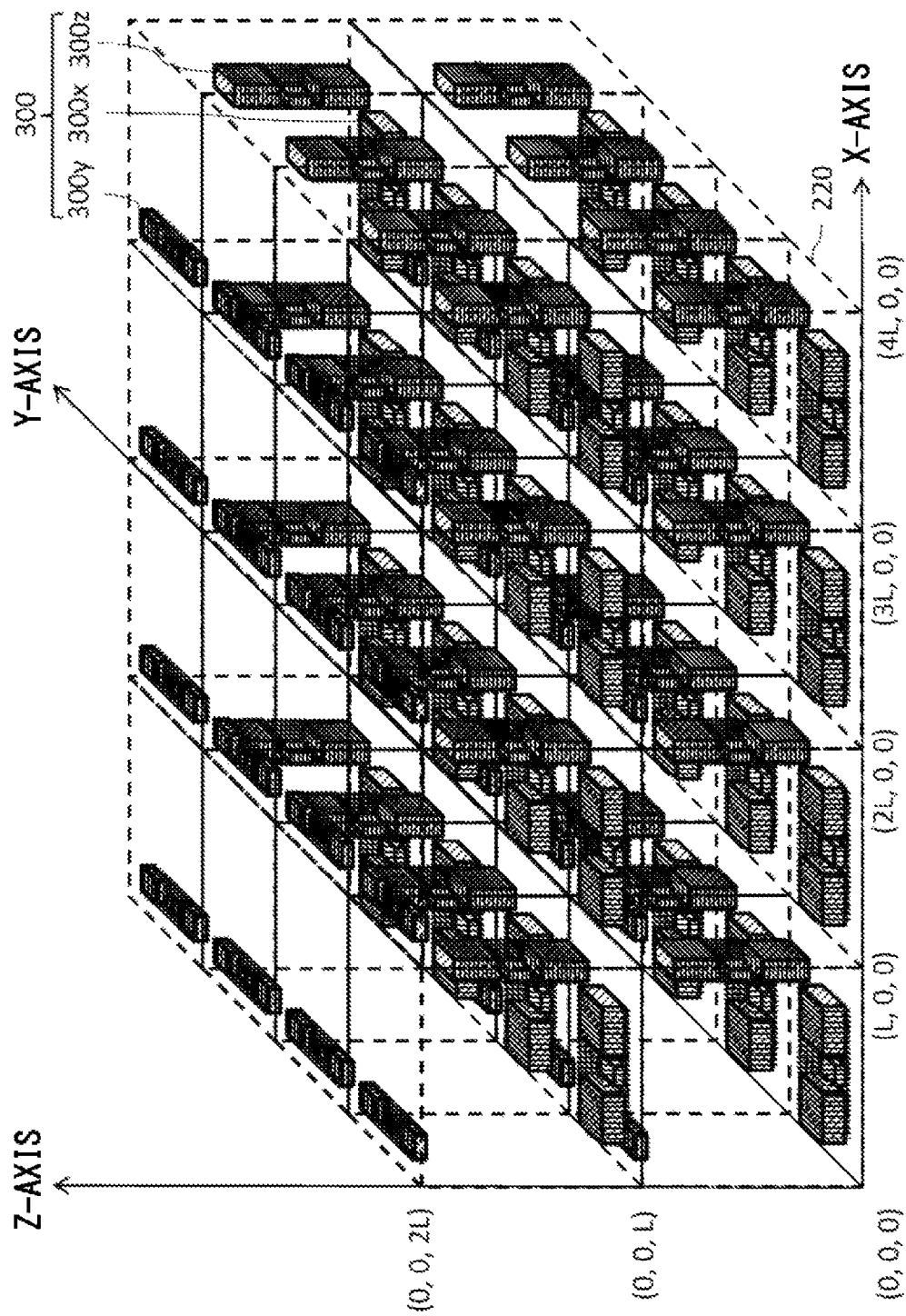
FIG. 27 illustrates a variation of the magnetic sensor array 210 according to the present embodiment.

FIG. 27 illustrates a variation of the magnetic sensor array 210 according to the present embodiment. In FIG. 27, members having the same function and configuration as in FIG. 16 are given the same reference numerals, and the following describes only differing points. In the present drawing, each of the plurality of magnetic sensor cells 220 of the magnetic sensor array 210 is provided with the sensor sections 300x, 300y, and 300z with no air space (gap) provided at a corner portion. In this way, even when the sensor sections 300 are thus arranged, the plurality of magnetic sensor cells 220 can each be arranged without the sensor sections 300x, 300y, and 300z overlapping each other as viewed in each of the three-dimensional direction on the X-axis, the Y-axis, and the Z-axis. With this arrangement, the plurality of sensor sections 300x, 300y, and 300z can be arranged in a dispersed manner in the magnetic sensor cell 220, whereby the plurality of sensor sections 300x, 300y, and 300z can be prevented from being arranged at a single corner portion in a concentrated manner. The magnetocardiographic measuring apparatus 10 according to the present embodiment may acquire measurement data using the magnetic sensor array 210 in which the sensor sections 300 are arranged in this manner.

A variety of embodiments of the present invention may be described with reference to flowcharts and block diagrams, where the blocks may represent: (1) steps of processes in which operations are performed; or (2) sections of devices responsible for performing the operations. Certain steps and sections may be implemented by dedicated circuitry, programmable circuitry supplied together with computer readable instructions stored on the computer readable medium, and/or a processor supplied together with computer readable instructions stored on the computer readable medium. Dedicated circuitry may include digital and/or analog hardware circuits and may include integrated circuits (IC) and/or discrete circuits. Programmable circuitry may include reconfigurable hardware circuits comprising, for example, logical AND, logical OR, logical XOR, logical NAND, logical NOR, and other logical operations, and memory elements such as flip-flops, registers, field-programmable gate arrays (FPGA), programmable logic arrays (PLA) or other.

Computer readable medium may include any tangible device that can store instructions for execution by a suitable device, such that the computer readable medium having instructions stored thereon comprises a product including instructions which can be executed to create means for performing operations specified in the flowcharts or block diagrams. Examples of the computer-readable medium may include an electronic storage medium, a magnetic storage medium, an optical storage medium, an electromagnetic storage medium, a semiconductor storage medium, or the like. More specific examples of computer readable medium may include a floppy (registered trademark) disk, a diskette, a hard disk, a random access memory (RAM), a read-only memory (ROM), an erasable programmable read-only memory (EPROM or Flash memory), an electrically erasable programmable read-only memory (EEPROM), a static random access memory (SRAM), a compact disc read-only memory (CD-ROM), a digital versatile disk (DVD), a Blu-ray (registered trademark) disc, a memory stick, an integrated circuit card, or other.

Computer readable instructions may include assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk (registered trademark), JAVA (registered trademark), C++, etc., and conventional procedural programming languages, such as the "C" programming language or similar programming languages.

Computer readable instructions may be provided to a processor of a general-purpose computer, an application specific computer, or other programmable data processing device, or to programmable circuitry, locally or via a local area network (LAN), wide area network (WAN) such as the Internet or other, to execute the computer readable instructions to create means for performing operations specified in the flowcharts or block diagrams. Examples of the processor include a computer processor, a processing unit, a microprocessor, a digital signal processor, a controller, a microcontroller, or the like.

Figure 28:
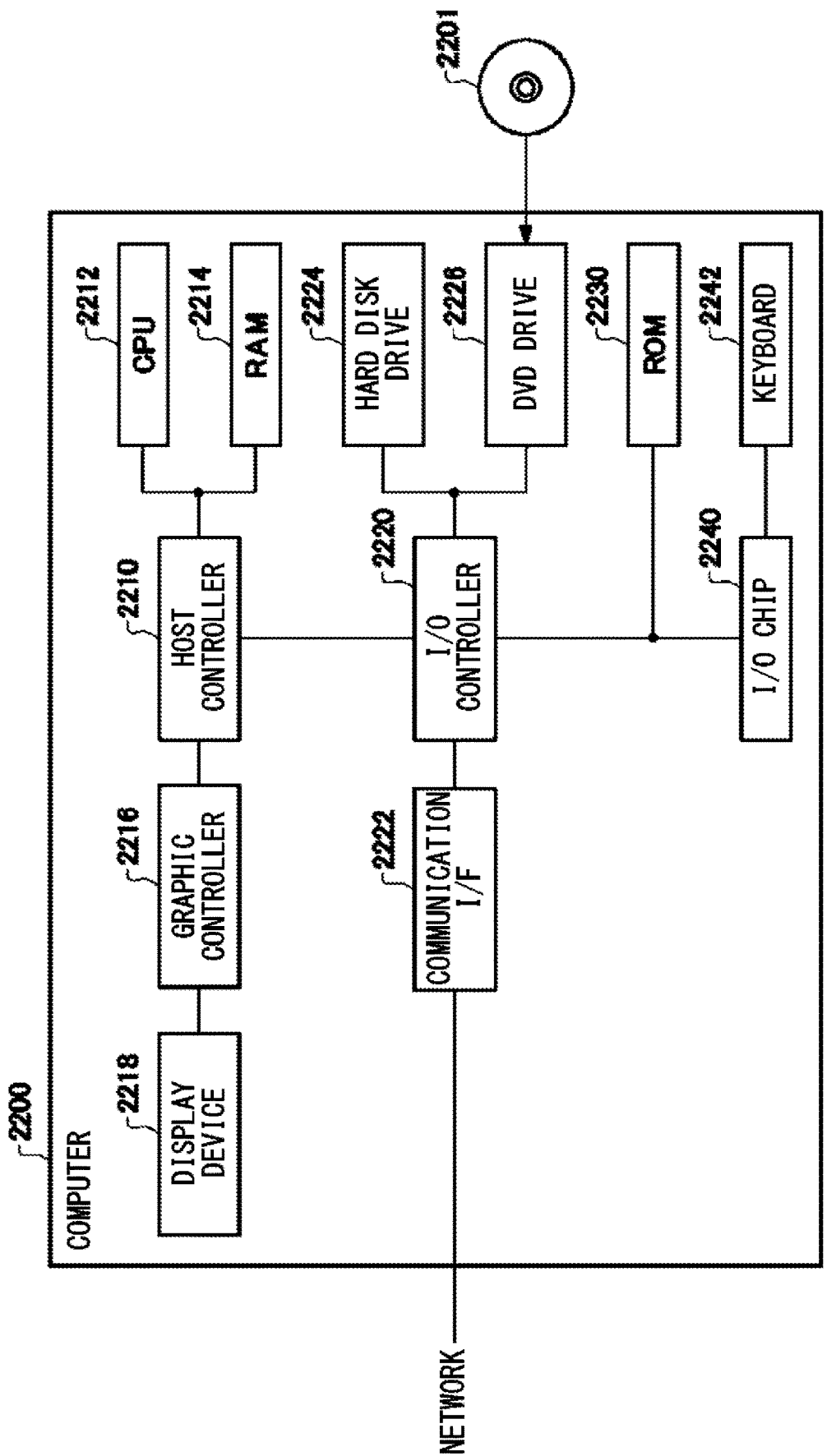
FIG. 28 illustrates an example of a computer 2200 through which a plurality of aspects of the present invention may be entirely or partially embodied.

FIG. 28 illustrates an example of a computer 2200 in which the plurality of aspects of the present invention may be wholly or partially embodied. A program that is installed in the computer 2200 can cause the computer 2200 to function as or perform operations associated with the device according to the embodiments of the present invention or one or more sections of said device, or perform said operations or said one or more sections, and/or cause the computer 2200 to perform the processes according to the embodiments of the present invention or steps of said processes. Such a program may be executed by the CPU 2212 to cause the computer 2200 to perform certain operations associated with some or all of the blocks of flowcharts and block diagrams described in the present specification.

The computer 2200 according to the present embodiment includes a CPU 2212, an RAM 2214, a graphic controller 2216, and a display device 2218, which are mutually connected by a host controller 2210. The computer 2200 also includes input/output units such as a communication interface 2222, a hard disk drive 2224, a DVD-ROM drive 2226 and an IC card drive, which are connected to the host controller 2210 via an input/output controller 2220. The computer also includes legacy input/output units such as an ROM 2230 and a keyboard 2242, which are connected to the input/output controller 2220 via an input/output chip 2240.

The CPU 2212 operates according to programs stored in the ROM 2230 and the RAM 2214, thereby controlling each unit. The graphic controller 2216 obtains image data generated by the CPU 2212 on a frame buffer or other provided in the RAM 2214 or in itself, and causes the image data to be displayed on the display device 2218.

The communication interface 2222 communicates with other electronic devices via the network. The hard disk drive 2224 stores programs and data used by the CPU 2212 in the computer 2200. The DVD-ROM drive 2226 reads the programs or the data from the DVD-ROM 2201, and provides the hard disk drive 2224 with the programs or the data via the RAM 2214. The IC card drive reads programs and data from an IC card, and/or writes programs and data into the IC card.

The ROM 2230 stores therein a boot program or other to be executed by the computer 2200 when activated, and/or a program which depends on the hardware of the computer 2200. The input/output chip 2240 may also connect a variety of input/output units to the input/output controller 2220, via a parallel port, a serial port, a keyboard port, a mouse port, or other.

A program is provided by computer readable medium such as the DVD-ROM 2201 or an IC card. The program is read from the computer readable medium, installed into the hard disk drive 2224, RAM 2214, or ROM 2230, which are also examples of computer readable media, and executed by the CPU 2212. The information processing described in these programs is read into the computer 2200, which results in cooperation between a program and a variety of types of hardware resources mentioned above. The device or the method may be configured by realizing the operation or processing of information in accordance with the use of the computer 2200.

For example, when communication is executed between the computer 2200 and an external device, the CPU 2212 may execute a communication program loaded onto the RAM 2214 and instruct the communication interface 2222 to perform communication processing based on the processing described in the communication program. Under the control of the CPU 2212, the communication interface 2222 reads transmission data stored in a transmit buffer processing area provided in a recording medium such as the RAM 2214, the hard disk drive 2224, the DVD-ROM 2201, or the IC card, and then transmits the read transmission data to the network or writes reception data received from the network in a receive buffer processing area etc. provided in the recording medium.

In addition, the CPU 2212 may cause all or a necessary portion of a file or a database to be read into the RAM 2214, the file or the database having been stored in an external recording medium such as the hard disk drive 2224, the DVD-ROM drive 2226 (DVD-ROM 2201), the IC card or other, and perform a variety of types of processing on the data on the RAM 2214. The CPU 2212 may then write back the processed data to the external recording medium.

A variety of types of information, such as a variety of types of programs, data, tables, and databases, may be stored in the recording medium to undergo information processing. The CPU 2212 may perform a variety of types of processing on the data read from the RAM 2214, which includes a variety of types of operations, information processing, condition determination, conditional branch, unconditional branch, retrieval/replacement of information or other, as described anywhere throughout this disclosure and designated by an instruction sequence of programs, and writes the result back to the RAM 2214. In addition, the CPU 2212 may retrieve information in a file, a database or other, in a recording medium. For example, if a plurality of entries are stored in the recording medium, where each entry has an attribute value of a first attribute associated with an attribute value of a second attribute, the CPU 2212 may retrieve an entry which matches the condition having a designated attribute value of the first attribute, from among said plurality of entries, and read the attribute value of the second attribute stored in said entry, thereby obtaining the attribute value of the second attribute associated with the first attribute which meets the predetermined condition.

The program or software modules described above may be stored in the computer readable medium on the computer 2200 or in the vicinity of the computer 2200. In addition, a recording medium such as a hard disk or an RAM provided in a server system connected to a dedicated communication network or the Internet can be used as the computer readable medium, thereby providing the program to the computer 2200 via the network.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention. In addition, the invention is described as if the magnetic field measuring apparatus is a magnetocardiographic measuring apparatus as an embodiment of the present invention, but it is not limited to a magnetocardiographic measuring apparatus, but may be an apparatus that measures the magnetic field generated by the electrical activity of organs other than the human heart (for example, an apparatus used in tomography in medical diagnosis of the digestive system).

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

EXPLANATION OF REFERENCES

10: magnetocardiographic measuring apparatus; 100: main body; 110: magnetic sensor unit; 120: head; 125: driving section; 130: base portion; 140: pole portion; 150: information processing section; 210: magnetic sensor array; 220: magnetic sensor cell; 230: sensor data gathering section; 300: sensor section; 520: magnetic sensor; 530: the first magnetic field generation section; 532: the first amplification circuit; 534: the first coil; 540: output section; 710: magnetoresistive element; 720, 730: magnetic flux concentrator; 910: current DA converter; 920: the second magnetic field generation section; 922: the second amplification circuit; 924: the second coil; 1010: magnetization free layer; 1020: magnetization fixed layer; 1700: sensor data processing section; 1710: AD converter; 1712: clock generator; 1720: measurement data acquiring section; 1721: measurement data computing section; 1730: calibration calculation section; 1740: data output section; 1750: basis vector storage section; 1760: signal space separation section; 1770: indicator calculation section; 1771: basis vector calibration section; 1780: indicator output section; 1790: failure determination section; 2000: gradient magnetic field computing section; 2200: computer; 2201: DVD-ROM; 2210: host controller; 2212: CPU; 2214: RAM; 2216: graphics controller; 2218: display device; 2220: input/output controller; 2222: communication interface; 2224: hard disk drive; 2226: DVD-ROM drive; 2230: ROM; 2240: input/output chip; 2242: keyboards

What is claimed is:

1. A magnetic field measuring apparatus, comprising:
   one or more processors supplied with computer readable instructions stored on one or more non-transitory, computer-readable storage media such that execution of the computer-readable instructions by the one or more processors provides a measurement data acquiring section and a measurement data computing section; and
   a magnetic sensor array including a plurality of magnetic sensor cells, which is configured to detect an input magnetic field, which includes a to-be-measured magnetic field, in three axial directions at a plurality of locations in three-dimensional space, wherein each of the plurality of magnetic sensor cells comprises one or more magnetic sensors and one or more output sections each corresponding to a corresponding one of the one or more magnetic sensors, each of the one or more output sections being configured to output a corresponding output signal corresponding to the corresponding one of the one or more magnetic sensors, wherein the corresponding output signal of each of the one or more output sections is based on a corresponding input magnetic field including a corresponding to-be-measured magnetic field that correspond to the corresponding one of the one or more magnetic sensors,
   wherein the measurement data acquiring section for acquiring is configured to acquire measurement data based on the corresponding output signal from each of the one or more output sections, and
   wherein the measurement data computing section for calibrating is configured to calibrate the measurement data acquired by the measurement data acquiring section to provide calibrated measurement data that provide a measure of at least one of the input magnetic field and the to-be-measured magnetic field at the plurality of locations in three-dimensional space, and wherein
   the measurement data computing section comprises:
   an indicator calculation section for calculating an indicator illustrating calibration accuracy of the measurement data computing section; and
   a failure determination section for determining a failure based at least in part on the indicator calculated by the indicator calculation section; wherein the failure determination section generates an alert to alert a user if the failure determination section determines that a failure has occurred.

2. The magnetic field measuring apparatus according to claim 1, wherein:
   each of the plurality of magnetic sensor cells further includes one or more first magnetic field generation sections for each of the one or more magnetic sensors for generating a feedback magnetic field configured to reduce the corresponding input magnetic field detected by each of the one or more magnetic sensors by a magnitude corresponding to the corresponding output signal; and
   the corresponding one of the one or more output sections is configured to output the corresponding output signal, which corresponds to a feedback current flowing to generate the feedback magnetic field by the corresponding one of the one or more first magnetic field generation sections.

3. The magnetic field measuring apparatus according to claim 2, wherein each of the one or more magnetic sensors includes a magnetoresistive element and two magnetic flux concentrators arranged on both ends of the magnetoresistive element, wherein the magnetoresistive element is arranged at a position sandwiched between two of the magnetic flux concentrators.

4. The magnetic field measuring apparatus according to claim 3, wherein each of the one or more first magnetic field generation sections includes a first coil wrapped along an axial direction of a magnetic field which is a detection target of the corresponding one of the one or more magnetic sensors, so as to enclose the magnetoresistive element and two of the magnetic flux concentrators.

5. The magnetic field measuring apparatus according to claim 3, wherein:
   each of the plurality of magnetic sensor cells further includes one or more second magnetic field generation sections for each of the one or more magnetic sensors for generating a cancellation magnetic field configured to reduce a corresponding environment magnetic field, which is included in the corresponding input magnetic field detected by the corresponding one of the one or more magnetic sensors; and each of the one or more second magnetic field generation sections includes a second coil wrapped along a axial direction of a magnetic field which is a detection target of the magnetic sensor, so as to enclose the magnetoresistive element and two of the magnetic flux concentrators.

6. The magnetic field measuring apparatus according to claim 4, wherein:

each of the plurality of magnetic sensor cells further includes one or more second magnetic field generation sections for each of the one or more magnetic sensors for generating a cancellation magnetic field configured to reduce a corresponding environment magnetic field, which is included in the corresponding input magnetic field detected by the corresponding one of the one or more magnetic sensors; and each of the one or more second magnetic field generation sections includes a second coil wrapped along a axial direction of the magnetic field which is a detection target of the magnetic sensor, so as to enclose the magnetoresistive element and two of the magnetic flux concentrators.

7. The magnetic field measuring apparatus according to claim 2, wherein each of the plurality of magnetic sensor cells includes three sensor sections, each of which includes the magnetic sensor, the first magnetic field generation section and the output section, and is capable of detecting a magnetic field in the three axial directions.

8. The magnetic field measuring apparatus according to claim 3, wherein each of the plurality of magnetic sensor cells includes three sensor sections, each of which includes the magnetic sensor, the first magnetic field generation section and the output section, and is capable of detecting a magnetic field in the three axial directions.

9. The magnetic field measuring apparatus according to claim 4, wherein each of the plurality of magnetic sensor cells includes three sensor sections, each of which includes the magnetic sensor, the first magnetic field generation section and the output section, and is capable of detecting a magnetic field in the three axial directions.

10. The magnetic field measuring apparatus according to claim 5, wherein each of the plurality of magnetic sensor cells includes three sensor sections, each of which includes the magnetic sensor, the first magnetic field generation section and the output section, and is capable of detecting a magnetic field in the three axial directions.

11. The magnetic field measuring apparatus according to claim 1, wherein:

the measurement data computing section further includes a signal space separation section for performing signal separation on the input magnetic field spatial distribution indicated by magnetic field measurement data generated from the measurement data, using, as basis vectors, signal vectors output by each of the one or more magnetic sensors when the magnetic sensor array detects a magnetic field having a spatial distribution of orthonormal functions; and the indicator calculation section is configured to calculate the indicator based on a result of a signal separation performed by the signal space separation section.

12. The magnetic field measuring apparatus according to claim 7, wherein:

the measurement data computing section further includes a signal space separation section for performing signal separation on the input magnetic field spatial distribution indicated by magnetic field measurement data generated from the measurement data, using, as basis vectors, signal vectors output by each of the one or more magnetic sensors when the magnetic sensor array detects a magnetic field having a spatial distribution of an orthonormal functions; and the indicator calculation section is configured to calculate the indicator based on a result of a signal separation performed by the signal space separation section.

13. The magnetic field measuring apparatus according to claim 1, wherein the indicator calculation section is configured to calculate the indicator based on statistics of magnetic field measurement data in the plurality of magnetic sensor cells generated from the measurement data.

14. The magnetic field measuring apparatus according to claim 2, wherein the indicator calculation section is configured to calculate the indicator based on statistics of magnetic field measurement data in the plurality of magnetic sensor cells generated from the measurement data.

15. The magnetic field measuring apparatus according to claim 1, wherein the measurement data computing section further includes an indicator output section for outputting the indicator calculated by the indicator calculation section.

16. The magnetic field measuring apparatus according to claim 2, wherein the measurement data computing section further includes an indicator output section for outputting the indicator calculated by the indicator calculation section.

17. The magnetic field measuring apparatus according to claim 1, wherein the measurement data computing section is configured to recalibrate the measurement data based on the indicator calculated by the indicator calculation section.

18. The magnetic field measuring apparatus according to claim 2, wherein the measurement data computing section is configured to recalibrate the measurement data based on the indicator calculated by the indicator calculation section.

19. The magnetic field measuring apparatus according to claim 1, wherein the magnetic sensor array is arranged in a curved surface shape.

20. The magnetic field measuring apparatus according to claim 2, wherein the magnetic sensor array is arranged in a curved surface shape.

* * * * *